(12) United States Patent
Nettekoven et al.

(10) Patent No.: US 7,723,325 B2
(45) Date of Patent: May 25, 2010

(54) 5-AMIDO-INDOLE-2-CARBOXAMIDE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/493,516

(22) Filed: Jun. 29, 2009

(65) Prior Publication Data

US 2009/0264418 A1 Oct. 22, 2009

Related U.S. Application Data

(62) Division of application No. 11/784,041, filed on Apr. 5, 2007, now Pat. No. 7,601,711.

(30) Foreign Application Priority Data

Apr. 12, 2006 (EP) .................................. 06112562

(51) Int. Cl.
| | |
|---|---|
| A61K 31/4439 | (2006.01) |
| A61K 31/5355 | (2006.01) |
| A61K 31/541 | (2006.01) |
| C07D 295/192 | (2006.01) |
| C07D 401/14 | (2006.01) |
| C07D 413/14 | (2006.01) |

(52) U.S. Cl. ................. 514/228.2; 514/235.2; 514/316; 514/323; 544/58.2; 544/130; 546/187; 546/201

(58) Field of Classification Search ....................... None
See application file for complete search history.

(56) References Cited

U.S. PATENT DOCUMENTS

2006/0069087 A1   3/2006 Wager

FOREIGN PATENT DOCUMENTS

| WO | WO 2005/123716 | 12/2005 | |
|---|---|---|---|
| WO | WO 2006/077024 | * | 7/2006 |

* cited by examiner

*Primary Examiner*—Golam M. M. Shameem
*Assistant Examiner*—Alicia L Fierro
(74) *Attorney, Agent, or Firm*—George W. Johnston; Dennis P. Tramaloni; Samuel H. Megerditchian

(57) ABSTRACT

The present invention relates to compounds of formula I

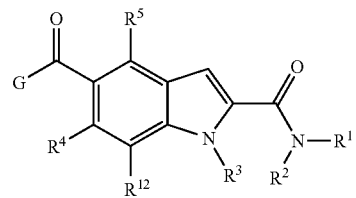

wherein G and $R^1$ to $R^5$ and $R^{12}$ are as defined in the description and claims, and pharmaceutically acceptable salts thereof. The compounds are useful for the treatment and/or prevention of diseases which are associated with the modulation of H3 receptors.

17 Claims, No Drawings

5-AMIDO-INDOLE-2-CARBOXAMIDE DERIVATIVES

PRIORITY TO RELATED APPLICATION

This application is a division of U.S. application Ser. No. 11/784,041, filed Apr. 5, 2007 which claims the benefit of European Patent Application No. 06112562.1, filed Apr. 12, 2006, which is hereby incorporated by reference in its entirety.

FIELD OF THE INVENTION

The present invention is concerned with novel 5-amido-2-carboxamide indole derivatives, their manufacture, pharmaceutical compositions containing them and their use as medicaments. The active compounds of the present invention are useful in treating obesity and other disorders.

In a preferred embodiment, the present invention relates to compounds of the general formula

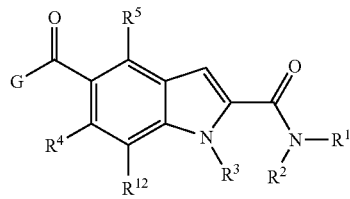

I and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine(2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

SUMMARY OF THE INVENTION

In an embodiment of the present invention, provided is a compound of formula I:

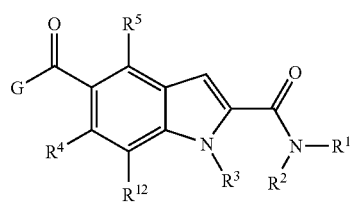

I wherein:

$R^1$ is selected from the group consisting of
  lower alkyl, lower alkenyl, lower alkanet,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one to three groups independently selected from lower alkyl, halogen, lower halogenalkoxy and lower hydroxyalkyl, lower phenylalkyl wherein the phenyl ring may be unsubstituted or substituted with one to three groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclylalkyl wherein the heterocyclyl ring may be unsubstituted or substituted with one or two groups selected from lower alkyl and halogen, and 7-oxa-bicyclo[2.2.1]heptyl;

$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one to three groups independently selected from lower alkyl, halogen, lower halogenalkoxy and lower hydroxyalkyl, lower phenylalkyl wherein the phenyl ring may be unsubstituted or substituted with one to three groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, and lower heterocyclylalkyl wherein the heterocycly ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or $R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one;

$R^3$ is selected from the group consisting of hydrogen, lower alkyl, cycloalkyl, lower hydroxyalkyl, lower alkoxyalkyl, lower halogenalkyl, lower cycloalkylalkyl, lower alkanoyl, lower cyanoalkyl, lower alkylsulfonyl, phenylsulfonyl wherein the phenyl ring may be unsubstituted or substituted with one to three groups independently selected from lower alkyl, halogen, lower alkoxy, lower halogenalkoxy and lower hydroxyalkyl, phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl, lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and heteroaryl unsubstituted or substituted with one or two groups independently selected from lower alkyl, lower alkoxy, cyano, morpholinyl and halogen;

$R^4$, $R^{12}$ and $R^5$ are hydrogen, or one of $R^4$, $R^{12}$ and $R^5$ is halogen and the other ones are hydrogen;

G is a group selected from

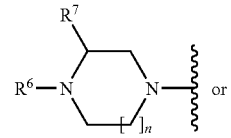

G1

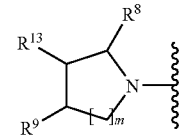

G2 wherein $R^6$ is selected from the group consisting of lower alkyl, cycloalkyl, lower cycloalkylalkyl and a heterocyclic ring containing oxygen;

$R^7$ is hydrogen; or $R^6$ and $R^7$ together are $—(CH_2)_p—$, wherein p is 3 or 4, and are bonded to each other to form a ring together with the carbon or nitrogen atom to which they are attached;

n is 1 or 2;

m is 1 or 2;

$R^8$ is hydrogen or lower heterocyclylalkyl;

$R^9$ is hydrogen or $—NR^{10}R^{11}$;

$R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur;

$R^{13}$ is hydrogen or $—NR^{10}R^{11}$;

and pharmaceutically acceptable salts thereof.

In another embodiment of the present invention, provided is a process for the manufacture of a compound according to formula I, comprising the steps of:

reacting a compound of formula II

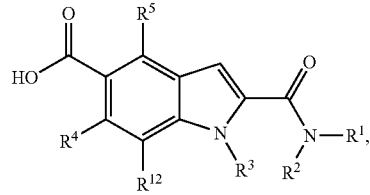

II wherein $R^1$, $R^2$, $R^4$, $R^{12}$ and $R^5$ are as defined herein before and $R^3$ is hydrogen, with an amine of the formula IIIA or IIIB

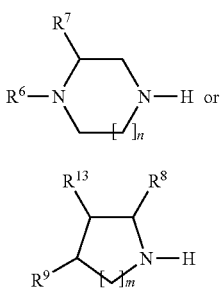

IIIA

IIIB wherein $R^6$, $R^7$, $R^8$, $R^9$, $R^{13}$, m and n are as defined herein before, in the presence of a coupling reagent under basic conditions to obtain a compound of the formula IA

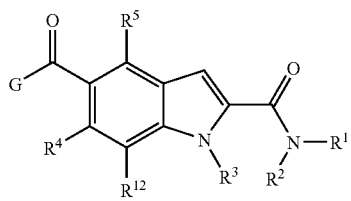

IA wherein $R^1$, $R^2$, $R^4$, $R^{12}$, $R^5$ and G are as defined herein before and $R^3$ is hydrogen, and optionally transferring into a compound of formula IB

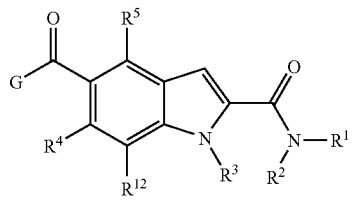

IB wherein $R^3$ is a group as defined herein before other than hydrogen, and if desired, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically active amount of a compound according to formula I to a human being or animal in need thereof.

In a still further embodiment of the present invention, provided is a method for the treatment or prevention of obesity in a human being or animal, comprising the step of administering a therapeutically effective amount of a compound of formula I in combination or association with a therapeutically effective amount of a compound selected from the group consisting of a lipase inhibitor, an anorectic agent, a selective serotonin reuptake inhibitor, and an agent that stimulates metabolism of body fat.

In a yet still another embodiment of the present invention, provided is a method of treatment or prevention of type II diabetes in a human being or animal, comprising the step of administering a therapeutically effective amount of a compound according to formula I in combination or association with a therapeutically effective amount of an anti-diabetic agent.

DETAILED DESCRIPTION

The present invention provides for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-8}$-alkinyl", alone or in combination, signifies a straight-chain or branched hydrocarbon residue comprising a triple bond and up to 8, preferably up to 6, particularly preferred up to 4 carbon atoms. Examples of alkinyl groups are ethinyl, 1-propinyl, or 2-propinyl. A preferred example is 2-propinyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl.

Especially preferred are cyclobutyl and cyclopentyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "alkoxy" or "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_1$-$C_8$-alkoxy-$C_1$-$C_8$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenalkyl" or "halogen-$C_1$-$C_8$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, fluoromethyl and chloromethyl, with trifluoromethyl or 2,2,2-trifluoro ethyl being especially preferred.

The term "lower halogenalkoxy" or "halogen-$C_1$-$C_8$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "dialkylamino" refers to the group —NR'R", wherein R' and R" are lower alkyl and the term "lower alkyl" has the previously given significance. A preferred dialkylamino group is dimethylamino.

The term "alkylsulfonylamino" or "lower alkylsulfonylamino" refers to the group R'—S(O)$_2$—NH—, wherein R' is lower alkyl and the term "lower alkyl" has the previously given significance.

Examples of alkylsulfonyl groups are e.g. methylsulfonylamino or ethylsulfonylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "carbamoyl" refers to the group —CO—NH$_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are pyridyl and pyrimidinyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxetanyl, dihydropyranyl, tetrahydropyranyl, and thiomorpholinyl. Preferred heterocyclyl groups are pyrrolidinyl and piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered heterocyclic ring optionally containing a further heteroatom selected from oxygen or sulfur" refers to a N-heterocyclic ring, which may optionally contain a further oxygen or sulfur atom, such as azetidinyl, pyrrolidinyl, oxazolidinyl, isoxazolidinyl, thiazolidinyl, isothiazolidinyl, piperidinyl, morpholinyl, thiomorpholinyl, or azepanyl. A "4-, 5-, 6- or 7-membered heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl. The heterocyclic ring may also be condensed with a phenyl ring, said phenyl ring being unsubstituted or substituted by one, two or three groups independently selected from lower alkyl, lower alkoxy and halogen. Examples for such condensed heterocyclic rings are 3,4-dihydro-1H-isoquinoline or 1,3-dihydroisoindole.

The term "heterocyclic ring containing oxygen" refers preferably to cyclic ether rings such as oxetane, tetrahydrofurane and tetrahydropyrane.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers". Stereoisomers that are not mirror images of one another are termed "diastereoisomers", and stereoisomers that are non-superimposable mirror images are termed "enantiomers", or sometimes optical isomers.

In detail, the present invention relates to compounds of the general formula

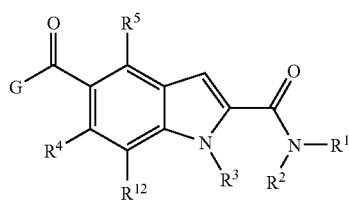

I wherein
$R^1$ is selected from the group consisting of
  lower alkyl, lower alkenyl, lower alkinyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one to three groups independently selected from lower alkyl, halogen, lower halogenalkoxy and lower hydroxyalkyl,
  lower phenylalkyl wherein the phenyl ring may be unsubstituted or substituted with one to three groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl,
  lower heterocyclylalkyl wherein the heterocyclyl ring may be unsubstituted or substituted with one or two groups selected from lower alkyl and halogen, and
  7-oxa-bicyclo[2.2.1]heptyl;
$R^2$ is selected from the group consisting of hydrogen,
  lower alkyl, lower alkenyl, lower alkinyl,
  cycloalkyl, lower cycloalkylalkyl,
  lower hydroxyalkyl, lower alkoxyalkyl,
  lower alkylsulfanylalkyl,
  lower dialkylaminoalkyl,
  lower dialkylcarbamoylalkyl,
  phenyl unsubstituted or substituted with one to three groups independently selected from lower alkyl, halogen, lower halogenalkoxy and lower hydroxyalkyl,
  lower phenylalkyl wherein the phenyl ring may be unsubstituted or substituted with one to three groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl, and
  lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring
  being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or
  being condensed with a phenyl ring, said phenyl ring being unsubstituted or substituted by one, two or three groups independently selected from lower alkyl, lower alkoxy and halogen, or
$R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one;
$R^3$ is selected from the group consisting of hydrogen, lower alkyl, cycloalkyl, lower hydroxyalkyl, lower alkoxyalkyl, lower halogenalkyl, lower cycloalkylalkyl, lower alkanoyl, lower cyanoalkyl, lower alkylsulfonyl,
  phenylsulfonyl wherein the phenyl ring may be unsubstituted or substituted with one to three groups independently selected from lower alkyl, halogen, lower alkoxy, lower halogenalkoxy and lower hydroxyalkyl,
  phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl, lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and heteroaryl unsubstituted or substituted with one or two groups independently selected from lower alkyl, lower alkoxy, cyano, morpholinyl and halogen;

$R^4$, $R^{12}$ and $R^5$ are hydrogen, or one of $R^4$, $R^{12}$ and $R^5$ is halogen and the other ones are hydrogen;

G is a group selected from

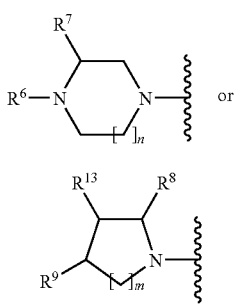

G1

G2 wherein $R^6$ is selected from the group consisting of lower alkyl, cycloalkyl, lower cycloalkylalkyl and a heterocyclic ring containing oxygen;

$R^7$ is hydrogen; or $R^6$ and $R^7$ together are —$(CH_2)_p$—, wherein p is 3 or 4, and are bonded to each other to form a ring together with the carbon or nitrogen atom to which they are attached;

n is 1 or 2;

m is 1 or 2;

$R^8$ is hydrogen or lower heterocyclylalkyl;

$R^9$ is hydrogen or —$NR^{10}R^{11}$;

$R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur;

$R^{13}$ is hydrogen or —$NR^{10}R^{11}$;

and pharmaceutically acceptable salts thereof.

Preferred are compounds of formula I according to the present invention, wherein $R^1$ is selected from the group consisting of lower alkyl, lower alkenyl, lower alkinyl, cycloalkyl, lower cycloalkylalkyl, lower hydroxyalkyl, lower alkoxyalkyl, lower alkylsulfanylalkyl, lower dialkylaminoalkyl, lower dialkylcarbamoylalkyl, phenyl unsubstituted or substituted with one to three groups independently selected from lower alkyl, halogen, lower halogenalkoxy and lower hydroxyalkyl, lower phenylalkyl wherein the phenyl ring may be unsubstituted or substituted with one to three groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl, lower heterocyclylalkyl wherein the heterocyclyl ring may be unsubstituted or substituted with one or two groups selected from lower alkyl and halogen, and 7-oxa-bicyclo[2.2.1]heptyl; and $R^2$ is hydrogen or lower alkyl.

More preferably, compounds of formula I according to the invention are those, wherein $R^1$ is selected from the group consisting of cycloalkyl, phenyl unsubstituted or substituted with one to three groups independently selected from lower alkyl, halogen, lower halogenalkoxy and lower hydroxyalkyl, lower phenylalkyl wherein the phenyl ring may be unsubstituted or substituted with one to three groups independently selected from lower alkyl, halogen, lower alkoxy and lower hydroxyalkyl, and lower heterocyclylalkyl wherein the heterocyclyl ring may be unsubstituted or substituted with one or two groups selected from lower alkyl and halogen; and $R^2$ is hydrogen or lower alkyl.

Further preferred compounds of formula I according the present invention are those, wherein $R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or wherein $R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one.

More preferably, the compounds of formula I according to the invention are those, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine, 1,1-dioxothiomorpholine and 3,6-dihydro-2H-pyridine, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or wherein $R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one.

Especially preferred are compounds of formula I according to the invention, wherein $R^1$ and $R^2$ together with the nitrogen atom to which they are attached form a heterocyclic ring selected from the group consisting of morpholine, thiomorpholine, 1,1-dioxothiomorpholine, pyrrolidine, piperidine and azepane, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or wherein $R^1$ and $R^2$ together with the nitrogen atom to which they are attached form a 1,4-dioxa-8-aza-spiro[4.5]decyl group.

Most preferably, compounds of formula I according to the invention are those, wherein $R^1$ and $R^2$ together with the nitrogen atom to which they are attached form a heterocyclic ring selected from the group consisting of morpholine, thiomorpholine, 1,1-dioxothio-morpholine, pyrrolidine, piperidine and 4,4-difluoropiperidinyl.

Preferred are furthermore compounds of formula I according to the present invention, wherein $R^3$ is selected from the group consisting of hydrogen, lower alkyl, cycloalkyl, lower hydroxyalkyl, lower alkoxyalkyl, lower halogenalkyl, lower cycloalkylalkyl, lower cyanoalkyl, lower alkylsulfonyl, phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl, lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and heteroaryl unsubstituted or substituted with one or two groups independently selected from lower alkyl, lower alkoxy, cyano, morpholinyl and halogen.

One group of preferred compounds of formula I of the invention are those, wherein $R^3$ is selected from the group consisting of hydrogen, lower alkyl, cycloalkyl, lower hydroxyalkyl, lower alkoxyalkyl, lower halogenalkyl, lower cycloalkylalkyl, lower cyanoalkyl and lower alkylsulfonyl, with those compounds, wherein $R^3$ is lower alkyl or lower halogenalkyl, being especially preferred. Compounds of formula I, wherein $R^3$ is hydrogen, are also preferred.

A further group of preferred compounds are compounds of formula I of the invention, wherein $R^3$ is phenyl unsubstituted or substituted with one to three groups independently selected from lower alkyl, halogen, cyano, morpholinyl, lower alkoxy, lower alkoxycarbonyl, lower halogenalkyl, lower haloge-nalkoxy, lower alkylsulfonyl and lower alkylsulfonylamino, benzodioxolyl, or lower phenylalkyl, wherein the phenyl ring may be unsubstituted or substituted with one to three groups independently selected from halogen, cyano or lower haloge-nalkyl, with those compounds of formula I, wherein $R^3$ is unsubstituted phenyl or phenyl substituted with one to three groups independently selected from halogen, cyano or lower halogenalkyl, being especially preferred.

Another group of preferred compounds of formula I are those, wherein $R^3$ is heteroaryl selected from pyridyl or pyrimidinyl, said heteroaryl being unsubstituted or substituted with one or two groups independently selected from lower alkyl, lower alkoxy, cyano, morpholinyl and halogen.

Compounds of formula I are preferred, wherein $R^{12}$ is hydrogen.

Furthermore, compounds of formula I according to the invention are preferred, wherein $R^4$, $R^{12}$ and $R^5$ are hydrogen.

Preferred compounds of formula I of the present invention are also those, wherein G signifies

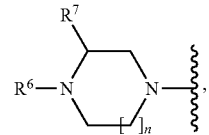

wherein $R^6$ is selected from the group consisting of lower alkyl, cycloalkyl, lower cycloalkylalkyl and a heterocyclic ring containing oxygen and $R^7$ is hydrogen;

or $R^6$ and $R^7$ together are —$(CH_2)_p$—, wherein p is 3 or 4, and are bonded to each other to form a ring together with the carbon or nitrogen atom to which they are attached;

and n is 1 or 2.

Especially preferred are compounds of formula I according to the invention, wherein $R^6$ is selected from the group consisting of lower alkyl, cycloalkyl and lower cycloalkylalkyl and $R^7$ is hydrogen, with those compounds of formula I, wherein $R^6$ is lower alkyl or cycloalkyl, being more preferred, and with compounds of formula I, wherein $R^6$ is selected from the group consisting of isopropyl, cyclobutyl and cyclopentyl.

Another group of preferred compounds of formula I according to the invention are those, wherein $R^6$ and $R^7$ together are —$(CH_2)_p$—, wherein p is 3 or 4, and are bonded to each other to form a ring together with the carbon or nitrogen atom to which they are attached, with those compounds of formula I, wherein p is 3, being especially preferred.

Furthermore, compounds of formula I, wherein n is 1, are preferred.

Also preferred are compounds of formula I of the present invention, wherein G signifies

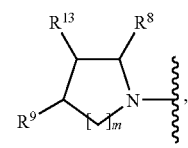

wherein m is 1 or 2, $R^8$ is hydrogen or lower heterocyclylalkyl, $R^9$ is hydrogen or —$NR^{10}R^{11}$, $R^{13}$ is hydrogen or —$NR^{10}R^{11}$, and $R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur.

More preferably, $R^{13}$ is hydrogen. Especially preferred are compounds of formula I, wherein $R^{12}$ and $R^{13}$ are hydrogen.

Especially preferred are also compounds of formula I according to the invention, wherein $R^8$ is hydrogen, $R^9$ is —$NR^{10}R^{11}$, $R^{13}$ is hydrogen and $R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur, with those compounds of formula I, wherein $R^{10}$ and $R^{11}$ independently from each other are lower alkyl, being more preferred. Most preferably, $R^{10}$ and $R^{11}$ are methyl.

One group of preferred compounds of formula I are those, wherein m is 1.

Compounds of formula I, wherein m is 2, are also preferred.

Also especially preferred are compounds of formula I according to the invention, wherein $R^8$ is lower heterocyclylalkyl and $R^9$ is hydrogen. More preferably, lower heterocyclylalkyl is lower pyrrolidinylalkyl, most preferably pyrrolidinylmethyl.

The present invention specifically relates to compounds of formula I having the general formula

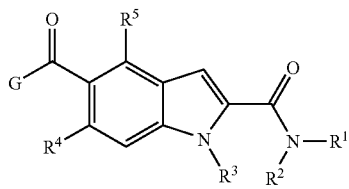

Ia wherein
$R^1$ is selected from the group consisting of
  lower alkyl, lower alkenyl, lower alkinyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
    phenyl unsubstituted or substituted with one to three groups independently selected from lower alkyl, halogen, lower halogenalkoxy and lower hydroxyalkyl,
    lower phenylalkyl wherein the phenyl ring may be unsubstituted or substituted with one to three groups independently selected from lower alkyl, halogen, lower alkoxy and lower hydroxyalkyl,
    lower heteroarylalkyl wherein the heteroaryl ring may be unsubstituted or substituted with one or two groups independently selected from lower alkyl, halogen, lower alkoxy and lower hydroxyalkyl,
    lower heterocyclylalkyl wherein the heterocyclyl ring may be unsubstituted or substituted with one or two groups selected from lower alkyl and halogen, and
  7-oxa-bicyclo[2.2.1]heptyl;
$R^2$ is selected from the group consisting of hydrogen,
  lower alkyl, lower alkenyl, lower alkinyl,
  cycloalkyl, lower cycloalkylalkyl,
  lower hydroxyalkyl, lower alkoxyalkyl,
  lower alkylsulfanylalkyl,
  lower dialkylaminoalkyl,
  lower dialkylcarbamoylalkyl,
    phenyl unsubstituted or substituted with one to three groups independently selected from lower alkyl, halogen, lower halogenalkoxy and lower hydroxyalkyl,
    lower phenylalkyl wherein the phenyl ring may be unsubstituted or substituted with one to three groups independently selected from lower alkyl, halogen, lower alkoxy and lower hydroxyalkyl,
    lower heteroarylalkyl wherein the heteroaryl ring may be unsubstituted or substituted with one or two groups independently selected from lower alkyl, halogen, lower alkoxy and lower hydroxyalkyl, and
    lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring
being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen, or
$R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one;
$R^3$ is selected from the group consisting of hydrogen, lower alkyl, cycloalkyl,
lower hydroxyalkyl, lower alkoxyalkyl, lower halogenalkyl, lower cycloalkylalkyl,
lower alkanoyl, lower cyanoalkyl, lower alkylsulfonyl,
  phenylsulfonyl wherein the phenyl ring may be unsubstituted or substituted with one to three groups independently selected from lower alkyl, halogen, lower alkoxy, lower halogenalkoxy and lower hydroxyalkyl,
  phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl,
  lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
  heteroaryl unsubstituted or substituted with one or two groups selected from lower alkyl, lower alkoxy, cyano, morpholinyl and halogen;
$R^4$ and $R^5$ are hydrogen, or
one of $R^4$ and $R^5$ is halogen and the other one is hydrogen;
G is a group selected from

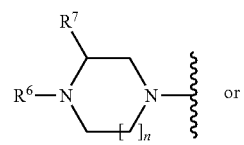

G1

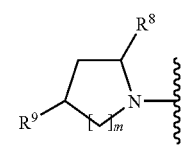

G2a wherein

R⁶ is selected from the group consisting of lower alkyl, cycloalkyl, lower cycloalkylalkyl and a heterocyclic ring containing oxygen;

R⁷ is hydrogen; or R⁶ and R⁷ together are —(CH$_2$)$_p$—, wherein p is 3 or 4, and are bonded to each other to form a ring together with the carbon or nitrogen atom to which they are attached;

n is 1 or 2;

m is 1 or 2;

R⁸ is hydrogen or lower heterocyclylalkyl;

R⁹ is hydrogen or —NR¹⁰R¹¹;

R¹⁰ and R¹¹ independently from each other are lower alkyl or together with the nitrogen atom to which they are attached form a 5- or 6-membered saturated heterocyclic ring optionally containing a further heteroatom selected from nitrogen, oxygen or sulfur;

and pharmaceutically acceptable salts thereof.

Preferred compounds of formula I of the present invention are the following:

[2-(1,1-dioxo-thiomorpholine-4-carbonyl)-1H-indol-5-yl]-(4-isopropyl-piperazin-1-yl)-methanone,

[5-(4-cyclopentyl-piperazine-1-carbonyl)-1H-indol-2-yl]-pyrrolidin-1-yl-methanone,

[5-(4-cyclopentyl-piperazine-1-carbonyl)-1H-indol-2-yl]-(2-methyl-pyrrolidin-1-yl)-methanone,

[5-(4-cyclopentyl-piperazine-1-carbonyl)-1H-indol-2-yl]-(2-isopropyl-pyrrolidin-1-yl)-methanone,

[5-(4-cyclopentyl-piperazine-1-carbonyl)-1H-indol-2-yl]-piperidin-1-yl-methanone,

[5-(4-cyclopentyl-piperazine-1-carbonyl)-1H-indol-2-yl]-(4-methyl-piperidin-1-yl)-methanone,

[5-(4-cyclopentyl-piperazine-1-carbonyl)-1H-indol-2-yl]-(4-methoxy-piperidin-1-yl)-methanone,

[5-(4-cyclopentyl-piperazine-1-carbonyl)-1H-indol-2-yl]-(4,4-difluoro-piperidin-1-yl)-methanone,

[5-(4-cyclopentyl-piperazine-1-carbonyl)-1H-indol-2-yl]-(4-hydroxy-piperidin-1-yl)-methanone,

[5-(4-cyclopentyl-piperazine-1-carbonyl)-1H-indol-2-yl]-morpholin-4-yl-methanone,

[5-(4-cyclopentyl-piperazine-1-carbonyl)-1H-indol-2-yl]-thiomorpholin-4-yl-methanone,

[5-(4-cyclopentyl-piperazine-1-carbonyl)-1H-indol-2-yl]-(3-fluoro-piperidin-1-yl)-methanone,

[5-(4-cyclopentyl-piperazine-1-carbonyl)-1H-indol-2-yl]-(4-trifluoromethyl-piperidin-1-yl)-methanone,

[5-(4-cyclopentyl-piperazine-1-carbonyl)-1H-indol-2-yl]-(3,4-dihydro-1H-isoquinolin-2-yl)-methanone, 5-(4-cyclopentyl-piperazine-1-carbonyl)-1H-indole-2-carboxylic acid benzyl-methyl-amide,

[5-(4-isopropyl-piperazine-1-carbonyl)-1H-indol-2-yl]-pyrrolidin-1-yl-methanone,

[5-(4-isopropyl-piperazine-1-carbonyl)-1H-indol-2-yl]-(2-methyl-pyrrolidin-1-yl)-methanone,

[5-(4-isopropyl-piperazine-1-carbonyl)-1H-indol-2-yl]-(2-isopropyl-pyrrolidin-1-yl)-methanone,

[5-(4-isopropyl-piperazine-1-carbonyl)-1H-indol-2-yl]-piperidin-1-yl-methanone,

[5-(4-isopropyl-piperazine-1-carbonyl)-1H-indol-2-yl]-(4-methyl-piperidin-1-yl)-methanone,

[5-(4-isopropyl-piperazine-1-carbonyl)-1H-indol-2-yl]-(4-methoxy-piperidin-1-yl)-methanone, (4-hydroxy-piperidin-1-yl)-[5-(4-isopropyl-piperazine-1-carbonyl)-1H-indol-2-yl]-methanone,

[5-(4-isopropyl-piperazine-1-carbonyl)-1H-indol-2-yl]-morpholin-4-yl-methanone,

[5-(4-isopropyl-piperazine-1-carbonyl)-1H-indol-2-yl]-thiomorpholin-4-yl-methanone, (3-fluoro-piperidin-1-yl)-[5-(4-isopropyl-piperazine-1-carbonyl)-1H-indol-2-yl]-methanone,

[5-(4-isopropyl-piperazine-1-carbonyl)-1H-indol-2-yl]-(4-trifluoromethyl-piperidin-1-yl)-methanone, 5-(4-isopropyl-piperazine-1-carbonyl)-1H-indole-2-carboxylic acid benzylamide, 5-(4-isopropyl-piperazine-1-carbonyl)-1H-indole-2-carboxylic acid benzyl-methyl-amide, 5-(4-isopropyl-piperazine-1-carbonyl)-1H-indole-2-carboxylic acid cyclopentylamide, azepan-1-yl-[5-(4-isopropyl-piperazine-1-carbonyl)-1H-indol-2-yl]-methanone, azepan-1-yl-[5-(4-cyclopentyl-piperazine-1-carbonyl)-1H-indol-2-yl]-methanone, (4,4-difluoro-piperidin-1-yl)-[5-(4-isopropyl-piperazine-1-carbonyl)-1H-indol-2-yl]-methanone, (3,4-dihydro-1H-isoquinolin-2-yl)-[5-(4-isopropyl-piperazine-1-carbonyl)-1H-indol-2-yl]-methanone,

[5-(4-cyclopentyl-piperazine-1-carbonyl)-1H-indol-2-yl]-(1,1-dioxo-thiomorpholin-4-yl)-methanone, 5-(4-cyclopentyl-piperazine-1-carbonyl)-1H-indole-2-carboxylic acid (4-fluoro-phenyl)-amide, 5-(4-cyclopentyl-piperazine-1-carbonyl)-1H-indole-2-carboxylic acid (4-fluoro-phenyl)-methyl-amide, 5-(4-cyclopentyl-piperazine-1-carbonyl)-1H-indole-2-carboxylic acid (2,6-dimethyl-phenyl)-amide, 5-(4-cyclopentyl-piperazine-1-carbonyl)-1H-indole-2-carboxylic acid (2,4,6-trimethyl-phenyl)-amide, 5-(4-cyclopentyl-piperazine-1-carbonyl)-1H-indole-2-carboxylic acid (2-fluoro-phenyl)-amide, (4-cyclopentyl-piperazin-1-yl)-[2-(2,3-dihydro-indole-1-carbonyl)-1H-indol-5-yl]-methanone,

[5-(4-cyclobutyl-piperazine-1-carbonyl)-1H-indol-2-yl]-(4,4-difluoro-piperidin-1-yl)-methanone, (4,4-difluoro-piperidin-1-yl)-[5-((S)-3-dimethylamino-pyrrolidine-1-carbonyl)-1H-indol-2-yl]-methanone, (4,4-difluoro-piperidin-1-yl)-[5-((R)-3-dimethylamino-pyrrolidine-1-carbonyl)-1H-indol-2-yl]-methanone,

[2-(4,4-difluoro-piperidine-1-carbonyl)-1H-indol-5-yl]-((S)-2-pyrrolidin-1-ylmethyl-pyrrolidin-1-yl)-methanone,

[2-(4,4-difluoro-piperidine-1-carbonyl)-1H-indol-5-yl]-((R)-2-pyrrolidin-1-ylmethyl-pyrrolidin-1-yl)-methanone,

[5-(4-isopropyl-piperazine-1-carbonyl)-1-(2,2,2-trifluoro-ethyl)-1H-indol-2-yl]-morpholin-4-yl-methanone,

[5-(hexahydro-pyrrolo[1,2-a]pyrazine-2-carbonyl)-1-(2,2,2-trifluoro-ethyl)-1H-indol-2-yl]-morpholin-4-yl-methanone,

[5-(4-cyclobutyl-piperazine-1-carbonyl)-1-(2,2,2-trifluoro-ethyl)-1H-indol-2-yl]-morpholin-4-yl-methanone,

[5-(4-cyclopentyl-piperazine-1-carbonyl)-1-(2,2,2-trifluoro-ethyl)-1H-indol-2-yl]-morpholin-4-yl-methanone,

[5-(4-cyclohexyl-piperazine-1-carbonyl)-1-(2,2,2-trifluoro-ethyl)-1H-indol-2-yl]-morpholin-4-yl-methanone,

[1-cyclopropylmethyl-5-(4-isopropyl-piperazine-1-carbonyl)-1H-indol-2-yl]-(4,4-difluoro-piperidin-1-yl)-methanone, (4,4-difluoro-piperidin-1-yl)-[5-(4-isopropyl-piperazine-1-carbonyl)-1-(2,2,2-trifluoro-ethyl)-1H-indol-2-yl]-methanone, (4,4-difluoro-piperidin-1-yl)-[1-isopropyl-5-(4-isopropyl-piperazine-1-carbonyl)-1H-indol-2-yl]-methanone,

[2-(4,4-difluoro-piperidine-1-carbonyl)-5-(4-isopropyl-piperazine-1-carbonyl)-indol-1-yl]-acetonitrile,

[5-(4-cyclopentyl-piperazine-1-carbonyl)-1-cyclopropylmethyl-1H-indol-2-yl]-(4,4-difluoro-piperidin-1-yl)-methanone,
[5-(4-cyclopentyl-piperazine-1-carbonyl)-1-(2,2,2-trifluoro-ethyl)-1H-indol-2-yl]-(4,4-difluoro-piperidin-1-yl)-methanone,
[5-(4-cyclopentyl-piperazine-1-carbonyl)-1-cyclopropylmethyl-1H-indol-2-yl]-morpholin-4-yl-methanone,
[5-(4-cyclopentyl-piperazine-1-carbonyl)-1-isopropyl-1H-indol-2-yl]-morpholin-4-yl-methanone,
[5-(4-cyclopentyl-piperazine-1-carbonyl)-1-isopropyl-1H-indol-2-yl]-(4,4-difluoro-piperidin-1-yl)-methanone,
(4,4-difluoro-piperidin-1-yl)-[5-(4-isopropyl-piperazine-1-carbonyl)-1-methanesulfonyl-1-indol-2-yl]-methanone,
[5-(4-cyclopentyl-piperazine-1-carbonyl)-2-(4,4-difluoro-piperidine-1-carbonyl)-indol-1-yl]-acetonitrile,
[5-(4-cyclopentyl-piperazine-1-carbonyl)-1-methanesulfonyl-1H-indol-2-yl]-(4,4-difluoro-piperidin-1-yl)-methanone,
[5-(4-cyclopentyl-piperazine-1-carbonyl)-2-(morpholine-4-carbonyl)-indol-1-yl]-acetonitrile,
(4-cyclopentyl-piperazin-1-yl)-[1-methanesulfonyl-2-(morpholine-4-carbonyl)-1H-indol-5-yl]-methanone,
[1-benzyl-5-(4-isopropyl-piperazine-1-carbonyl)-1H-indol-2-yl]-(4,4-difluoro-piperidin-1-yl)-methanone,
(4,4-difluoro-piperidin-1-yl)-[5-(4-isopropyl-piperazine-1-carbonyl)-1-p-tolyl-1H-indol-2-yl]-methanone,
(4,4-difluoro-piperidin-1-yl)-[5-(4-isopropyl-piperazine-1-carbonyl)-1-(4-methoxy-phenyl)-1H-indol-2-yl]-methanone,
(4,4-difluoro-piperidin-1-yl)-[1-(4-fluoro-phenyl)-5-(4-isopropyl-piperazine-1-carbonyl)-1H-indol-2-yl]-methanone,
[1-(4-chloro-phenyl)-5-(4-isopropyl-piperazine-1-carbonyl)-1H-indol-2-yl]-(4,4-difluoro-piperidin-1-yl)-methanone,
(4,4-difluoro-piperidin-1-yl)-[5-(4-isopropyl-piperazine-1-carbonyl)-1-(4-trifluoromethyl-phenyl)-1H-indol-2-yl]-methanone,
4-[2-(4,4-difluoro-piperidine-1-carbonyl)-5-(4-isopropyl-piperazine-1-carbonyl)-indol-1-yl]-benzonitrile
[1-(3-chloro-phenyl)-5-(4-isopropyl-piperazine-1-carbonyl)-1H-indol-2-yl]-(4,4-difluoro-piperidin-1-yl)-methanone
3-[2-(4,4-difluoro-piperidine-1-carbonyl)-5-(4-isopropyl-piperazine-1-carbonyl)-indol-1-yl]-benzonitrile,
[1-benzyl-5-(4-isopropyl-piperazine-1-carbonyl)-1H-indol-2-yl]-(1,1-dioxo-thiomorpholin-4-yl)-methanone,
[1-(4-chloro-phenyl)-5-(4-cyclopentyl-piperazine-1-carbonyl)-1H-indol-2-yl]-(4,4-difluoro-piperidin-1-yl)-methanone,
[1-(3-chloro-phenyl)-5-(4-cyclopentyl-piperazine-1-carbonyl)-1H-indol-2-yl]-(4,4-difluoro-piperidin-1-yl)-methanone,
[5-(4-cyclopentyl-piperazine-1-carbonyl)-1-(4-fluoro-phenyl)-1H-indol-2-yl]-(4,4-difluoro-piperidin-1-yl)-methanone,
[5-(4-cyclopentyl-piperazine-1-carbonyl)-1-(3-fluoro-phenyl)-1H-indol-2-yl]-(4,4-difluoro-piperidin-1-yl)-methanone,
[5-(4-cyclopentyl-piperazine-1-carbonyl)-1-(4-trifluoromethyl-phenyl)-1H-indol-2-yl]-(4,4-difluoro-piperidin-1-yl)-methanone,
[5-(4-cyclopentyl-piperazine-1-carbonyl)-1-(3-trifluoromethyl-phenyl)-1H-indol-2-yl]-(4,4-difluoro-piperidin-1-yl)-methanone,
[5-(4-cyclopentyl-piperazine-1-carbonyl)-1-p-tolyl-1H-indol-2-yl]-(4,4-difluoro-piperidin-1-yl)-methanone,
[5-(4-cyclopentyl-piperazine-1-carbonyl)-1-m-tolyl-1H-indol-2-yl]-(4,4-difluoro-piperidin-1-yl)-methanone,
[5-(4-cyclopentyl-piperazine-1-carbonyl)-1-(4-methoxy-phenyl)-1H-indol-2-yl]-(4,4-difluoro-piperidin-1-yl)-methanone,
[5-(4-cyclopentyl-piperazine-1-carbonyl)-1-(3-methoxy-phenyl)-1H-indol-2-yl]-(4,4-difluoro-piperidin-1-yl)-methanone,
4-[5-(4-cyclopentyl-piperazine-1-carbonyl)-2-(4,4-difluoro-piperidine-1-carbonyl)-indol-1-yl]-benzoic acid methyl ester,
3-[5-(4-cyclopentyl-piperazine-1-carbonyl)-2-(4,4-difluoro-piperidine-1-carbonyl)-indol-1-yl]-benzoic acid ethyl ester,
[5-(4-cyclopentyl-piperazine-1-carbonyl)-2-(1,1-dioxo-1,1-thiomorpholine-4-carbonyl)-indol-1-yl]-acetonitrile,
4-[5-(4-cyclopentyl-piperazine-1-carbonyl)-2-(4,4-difluoro-piperidine-1-carbonyl)-indol-1-yl]-benzonitrile,
3-[5-(4-cyclopentyl-piperazine-1-carbonyl)-2-(4,4-difluoro-piperidine-1-carbonyl)-indol-1-yl]-benzonitrile,
(4,4-difluoro-piperidin-1-yl)-[5-(4-isopropyl-piperazine-1-carbonyl)-1-m-tolyl-1H-indol-2-yl]-methanone,
(4,4-difluoro-piperidin-1-yl)-[5-(4-isopropyl-piperazine-1-carbonyl)-1-(3-trifluoromethyl-phenyl)-1H-indol-2-yl]-methanone,
3-[2-(4,4-difluoro-piperidine-1-carbonyl)-5-(4-isopropyl-piperazine-1-carbonyl)-indol-1-yl]-benzoic acid ethyl ester,
4-[2-(4,4-difluoro-piperidine-1-carbonyl)-5-(4-isopropyl-piperazine-1-carbonyl)-indol-1-yl]-benzoic acid methyl ester,
(4,4-difluoro-piperidin-1-yl)-[1-(4-fluoro-benzyl)-5-(4-isopropyl-piperazine-1-carbonyl)-1H-indol-2-yl]-methanone,
(4,4-difluoro-piperidin-1-yl)-[5-(4-isopropyl-piperazine-1-carbonyl)-1-(1-phenyl-ethyl)-1H-indol-2-yl]-methanone,
cyclopropylmethyl-5-(4-isopropyl-piperazine-1-carbonyl)-1H-indole-2-carboxylic acid (3-fluoro-oxetan-3-ylmethyl)-amide,
[1-(3-chloro-phenyl)-5-(4-isopropyl-piperazine-1-carbonyl)-1H-indol-2-yl]-(1,1-dioxo-thiomorpholin-4-yl)-methanone,
3-[2-(1,1-dioxo-thiomorpholine-4-carbonyl)-5-(4-isopropyl-piperazine-1-carbonyl)-indol-1-yl]-benzonitrile,
(1,1-dioxo-thiomorpholin-4-yl)-[5-(4-isopropyl-piperazine-1-carbonyl)-1-(3-trifluoromethyl-phenyl)-1H-indol-2-yl]-methanone,
[1-(4-chloro-phenyl)-5-(4-cyclopentyl-piperazine-1-carbonyl)-1H-indol-2-yl]-(1,1-dioxo-thiomorpholin-4-yl)-methanone,
[5-(4-cyclopentyl-piperazine-1-carbonyl)-1-isopropyl-1H-indol-2-yl]-(1,1-dioxo-thiomorpholin-4-yl)-methanone,
[1-(3-chloro-phenyl)-5-(4-cyclopentyl-piperazine-1-carbonyl)-1H-indol-2-yl]-(1,1-dioxo-thiomorpholin-4-yl)-methanone,
[5-(4-cyclopentyl-piperazine-1-carbonyl)-1-(4-fluoro-phenyl)-1H-indol-2-yl]-(1,1-dioxo-thiomorpholin-4-yl)-methanone,
[5-(4-cyclopentyl-piperazine-1-carbonyl)-1-(3-fluoro-phenyl)-1H-indol-2-yl]-(1,1-dioxo-thiomorpholin-4-yl)-methanone,
[5-(4-cyclopentyl-piperazine-1-carbonyl)-1-(4-trifluoromethyl-phenyl)-1H-indol-2-yl]-(1,1-dioxo-thiomorpholin-4-yl)-methanone,

[5-(4-cyclopentyl-piperazine-1-carbonyl)-1-(3-trifluoromethyl-phenyl)-1H-indol-2-yl]-(1,1-dioxo-thiomorpholin-4-yl)-methanone,
[5-(4-cyclopentyl-piperazine-1-carbonyl)-1-p-tolyl-1H-indol-2-yl]-(1,1-dioxo-thiomorpholin-4-yl)-methanone,
[5-(4-cyclopentyl-piperazine-1-carbonyl)-1-m-tolyl-1H-indol-2-yl]-(1,1-dioxo-thiomorpholin-4-yl)-methanone,
[5-(4-cyclopentyl-piperazine-1-carbonyl)-1-cyclopropylmethyl-1H-indol-2-yl]-(1,1-dioxo-thiomorpholin-4-yl)-methanone,
[5-(4-cyclopentyl-piperazine-1-carbonyl)-1-(2,2,2-trifluoro-ethyl)-1H-indol-2-yl]-(1,1-dioxo-thiomorpholin-4-yl)-methanone,
[1-(4-chloro-phenyl)-5-(4-isopropyl-piperazine-1-carbonyl)-1H-indol-2-yl]-(1,1-dioxo-thiomorpholin-4-yl)-methanone,
4-[2-(1,1-dioxo-thiomorpholine-4-carbonyl)-5-(4-isopropyl-piperazine-1-carbonyl)-indol-1-yl]-benzonitrile,
(1,1-dioxo-thiomorpholin-4-yl)-[5-(4-isopropyl-piperazine-1-carbonyl)-1-(4-trifluoromethyl-phenyl)-1H-indol-2-yl]-methanone,
[1-cyclopropylmethyl-5-(4-isopropyl-piperazine-1-carbonyl)-1H-indol-2-yl]-(1,1-dioxo-thiomorpholin-4-yl)-methanone,
(1,1-dioxo-thiomorpholin-4-yl)-[5-(4-isopropyl-piperazine-1-carbonyl)-1-(2,2,2-trifluoro-ethyl)-1H-indol-2-yl]-methanone,
[5-(4-isopropyl-piperazine-1-carbonyl)-1-(3-trifluoromethyl-phenyl)-1H-indol-2-yl]-morpholin-4-yl-methanone,
[5-(4-isopropyl-piperazine-1-carbonyl)-1-(4-trifluoromethyl-phenyl)-1H-indol-2-yl]-morpholin-4-yl-methanone,
4-[5-(4-isopropyl-piperazine-1-carbonyl)-2-(morpholine-4-carbonyl)-indol-1-yl]-benzonitrile,
(4,4-difluoro-piperidin-1-yl)-[1-(3-fluoro-phenyl)-5-(4-isopropyl-piperazine-1-carbonyl)-1H-indol-2-yl]-methanone,
(1,1-dioxo-1,l,6-thiomorpholin-4-yl)-[5-(4-isopropyl-piperazine-1-carbonyl)-1-(1-phenyl-ethyl)-1H-indol-2-yl]-methanone,
(4,4-difluoro-piperidin-1-yl)-[1-[1-(2-fluoro-phenyl)-ethyl]-5-(4-isopropyl-piperazine-1-carbonyl)-1H-indol-2-yl]-methanone,
[1-cyclobutylmethyl-5-(4-isopropyl-piperazine-1-carbonyl)-1H-indol-2-yl]-(4,4-difluoro-piperidin-1-yl)-methanone,
(4,4-difluoro-piperidin-1-yl)-[5-(4-isopropyl-piperazine-1-carbonyl)-1-((R)-1-phenyl-ethyl)-1H-indol-2-yl]-methanone,
(4,4-difluoro-piperidin-1-yl)-[5-(4-isopropyl-piperazine-1-carbonyl)-1-((S)-1-phenyl-ethyl)-1H-indol-2-yl]-methanone,
[1-(3-chloro-phenyl)-5-(4-cyclobutyl-piperazine-1-carbonyl)-1H-indol-2-yl]-(4,4-difluoro-piperidin-1-yl)-methanone,
3-[5-(4-cyclobutyl-piperazine-1-carbonyl)-2-(4,4-difluoro-piperidine-1-carbonyl)-indol-1-yl]-benzonitrile,
[5-(4-cyclobutyl-piperazine-1-carbonyl)-1-(3-trifluoromethyl-phenyl)-1H-indol-2-yl]-(4,4-difluoro-piperidin-1-yl)-methanone,
[1-(4-chloro-phenyl)-5-(4-cyclobutyl-piperazine-1-carbonyl)-1H-indol-2-yl]-(4,4-difluoro-piperidin-1-yl)-methanone,
4-[5-(4-cyclobutyl-piperazine-1-carbonyl)-2-(4,4-difluoro-piperidine-1-carbonyl)-indol-1-yl]-benzonitrile,
[5-(4-cyclobutyl-piperazine-1-carbonyl)-1-(4-trifluoromethyl-phenyl)-1H-indol-2-yl]-(4,4-difluoro-piperidin-1-yl)-methanone,
[5-(4-cyclobutyl-piperazine-1-carbonyl)-1-cyclopropylmethyl-1H-indol-2-yl]-(4,4-difluoro-piperidin-1-yl)-methanone,
[5-(4-cyclobutyl-piperazine-1-carbonyl)-1-(2,2,2-trifluoro-ethyl)-1H-indol-2-yl]-(4,4-difluoro-piperidin-1-yl)-methanone,
[5-(4-cyclobutyl-piperazine-1-carbonyl)-1-isopropyl-1H-indol-2-yl]-(4,4-difluoro-piperidin-1-yl)-methanone,
[1-cyclopropylmethyl-5-(3-dimethylamino-pyrrolidine-1-carbonyl)-1H-indol-2-yl]-(4,4-difluoro-piperidin-1-yl)-methanone,
(4,4-difluoro-piperidin-1-yl)-[5-(3-dimethylamino-pyrrolidine-1-carbonyl)-1-(2,2,2-trifluoro-ethyl)-1H-indol-2-yl]-methanone,
(4,4-difluoro-piperidin-1-yl)-[5-(3-dimethylamino-pyrrolidine-1-carbonyl)-1-isopropyl-1H-indol-2-yl]-methanone,
[1-(3-chloro-phenyl)-5-(3-dimethylamino-pyrrolidine-1-carbonyl)-1H-indol-2-yl]-(4,4-difluoro-piperidin-1-yl)-methanone,
3-[2-(4,4-difluoro-piperidine-1-carbonyl)-5-(3-dimethylamino-pyrrolidine-1-carbonyl)-indol-1-yl]-benzonitrile,
(4,4-difluoro-piperidin-1-yl)-[5-(3-dimethylamino-pyrrolidine-1-carbonyl)-1-(3-trifluoromethyl-phenyl)-1H-indol-2-yl]-methanone,
[1-(3-chloro-phenyl)-5-(4-dimethylamino-piperidine-1-carbonyl)-1H-indol-2-yl]-(4,4-difluoro-piperidin-1-yl)-methanone,
3-[2-(4,4-difluoro-piperidine-1-carbonyl)-5-(4-dimethylamino-piperidine-1-carbonyl)-indol-1-yl]-benzonitrile,
(4,4-difluoro-piperidin-1-yl)-[5-(4-dimethylamino-piperidine-1-carbonyl)-1-(3-trifluoromethyl-phenyl)-1H-indol-2-yl]-methanone,
[1-(4-chloro-phenyl)-5-(4-dimethylamino-piperidine-1-carbonyl)-1H-indol-2-yl]-(4,4-difluoro-piperidin-1-yl)-methanone,
4-[2-(4,4-difluoro-piperidine-1-carbonyl)-5-(4-dimethylamino-piperidine-1-carbonyl)-indol-1-yl]-benzonitrile,
(4,4-difluoro-piperidin-1-yl)-[5-(4-dimethylamino-piperidine-1-carbonyl)-1-(4-trifluoromethyl-phenyl)-1H-indol-2-yl]-methanone,
[1-cyclopropyl-5-(4-isopropyl-piperazine-1-carbonyl)-1H-indol-2-yl]-(4,4-difluoro-piperidin-1-yl)-methanone,
(4,4-difluoro-piperidin-1-yl)-[5-(4-isopropyl-piperazine-1-carbonyl)-1-(1-methyl-1-phenyl-ethyl)-1H-indol-2-yl]-methanone,
[1-cyclopropylmethyl-5-(4-dimethylamino-piperidine-1-carbonyl)-1H-indol-2-yl]-(4,4-difluoro-piperidin-1-yl)-methanone,
(4,4-difluoro-piperidin-1-yl)-[5-(4-dimethylamino-piperidine-1-carbonyl)-1-(2,2,2-trifluoro-ethyl)-1H-indol-2-yl]-methanone,
[1-cyclobutyl-2-(4,4-difluoro-piperidine-1-carbonyl)-1H-indol-5-yl]-(4-isopropyl-piperazin-1-yl)-methanone,
[5-(4-cyclobutyl-piperazine-1-carbonyl)-1-(4-methanesulfonyl-phenyl)-1H-indol-2-yl]-(4,4-difluoro-piperidin-1-yl)-methanone,
[5-(4-cyclobutyl-piperazine-1-carbonyl)-1-(3,5-difluoro-phenyl)-1H-indol-2-yl]-(4,4-difluoro-piperidin-1-yl)-methanone,
[1-(2-chloro-pyridin-4-yl)-5-(4-cyclobutyl-piperazine-1-carbonyl)-1H-indol-2-yl]-(4,4-difluoro-piperidin-1-yl)-methanone,
[1-(6-chloro-pyridin-3-yl)-5-(4-cyclobutyl-piperazine-1-carbonyl)-1H-indol-2-yl]-(4,4-difluoro-piperidin-1-yl)-methanone,

[1-benzo[1,3]dioxol-5-yl-5-(4-cyclobutyl-piperazine-1-carbonyl)-1H-indol-2-yl]-(4,4-difluoro-piperidin-1-yl)-methanone,
[5-(4-cyclobutyl-piperazine-1-carbonyl)-1-(4-morpholin-4-yl-phenyl)-1H-indol-2-yl]-(4,4-difluoro-piperidin-1-yl)-methanone,
[5-(4-cyclobutyl-piperazine-1-carbonyl)-1-(6-morpholin-4-yl-pyridin-3-yl)-1H-indol-2-yl]-(4,4-difluoro-piperidin-1-yl)-methanone,
[5-(4-cyclobutyl-piperazine-1-carbonyl)-1-(2-methoxy-pyrimidin-5-yl)-1H-indol-2-yl]-(4,4-difluoro-piperidin-1-yl)-methanone,
(4,4-difluoro-piperidin-1-yl)-[5-((S)-3-dimethylamino-pyrrolidine-1-carbonyl)-1-(2,2,2-trifluoro-ethyl)-1H-indol-2-yl]-methanone,
(4,4-difluoro-piperidin-1-yl)-[5-((R)-3-dimethylamino-pyrrolidine-1-carbonyl)-1-(2,2,2-trifluoro-ethyl)-1H-indol-2-yl]-methanone,
N-{4-[5-(4-cyclobutyl-piperazine-1-carbonyl)-2-(4,4-difluoro-piperidine-1-carbonyl)-indol-1-yl]-phenyl}-methanesulfonamide,
[1-cyclopropylmethyl-5-((S)-2-pyrrolidin-1-ylmethyl-pyrrolidine-1-carbonyl)-1H-indol-2-yl]-(4,4-difluoro-piperidin-1-yl)-methanone,
(4,4-difluoro-piperidin-1-yl)-[1-isopropyl-5-((S)-2-pyrrolidin-1-ylmethyl-pyrrolidine-1-carbonyl)-1H-indol-2-yl]-methanone,
(4,4-difluoro-piperidin-1-yl)-[5-((S)-2-pyrrolidin-1-ylmethyl-pyrrolidine-1-carbonyl)-1-(2,2,2-trifluoro-ethyl)-1H-indol-2-yl]-methanone,
(4,4-difluoro-piperidin-1-yl)-[1-(2-methoxy-ethyl)-5-((S)-2-pyrrolidin-1-ylmethyl-pyrrolidine-1-carbonyl)-1H-indol-2-yl]-methanone,
[1-cyclobutylmethyl-5-((S)-2-pyrrolidin-1-ylmethyl-pyrrolidine-1-carbonyl)-1H-indol-2-yl]-(4,4-difluoro-piperidin-1-yl)-methanone,
(4,4-difluoro-piperidin-1-yl)-[1-(2-hydroxy-ethyl)-5-((S)-2-pyrrolidin-1-ylmethyl-pyrrolidine-1-carbonyl)-1H-indol-2-yl]-methanone,
[5-([1,4']bipiperidinyl-1'-carbonyl)-1H-indol-2-yl]-(4,4-difluoro-piperidin-1-yl)-methanone,
(4,4-difluoro-piperidin-1-yl)-[5-(4-pyrrolidin-1-yl-piperidine-1-carbonyl)-1H-indol-2-yl]-methanone,
[2-(4,4-difluoro-piperidine-1-carbonyl)-1H-indol-5-yl]-(4-morpholin-4-yl-piperidin-1-yl)-methanone,
[5-([1,4']bipiperidinyl-1'-carbonyl)-1-cyclopropylmethyl-1H-indol-2-yl]-(4,4-difluoro-piperidin-1-yl)-methanone,
[5-([1,4']bipiperidinyl-1'-carbonyl)-1-(2,2,2-trifluoro-ethyl)-1H-indol-2-yl]-(4,4-difluoro-piperidin-1-yl)-methanone,
[5-([1,4']bipiperidinyl-1'-carbonyl)-1-isopropyl-1H-indol-2-yl]-(4,4-difluoro-piperidin-1-yl)-methanone,
[5-([1,4']bipiperidinyl-1'-carbonyl)-1-(2-chloro-pyridin-4-yl)-1H-indol-2-yl]-(4,4-difluoro-piperidin-1-yl)-methanone,
[5-([1,4']bipiperidinyl-1'-carbonyl)-1-(3-chloro-phenyl)-1H-indol-2-yl]-(4,4-difluoro-piperidin-1-yl)-methanone,
[5-([1,4']bipiperidinyl-1'-carbonyl)-1-(3-trifluoromethyl-phenyl)-1H-indol-2-yl]-(4,4-difluoro-piperidin-1-yl)-methanone,
[5-([1,4']bipiperidinyl-1'-carbonyl)-1-(6-chloro-pyridin-3-yl)-1H-indol-2-yl]-(4,4-difluoro-piperidin-1-yl)-methanone,
[1-cyclopropylmethyl-5-(4-pyrrolidin-1-yl-piperidine-1-carbonyl)-1H-indol-2-yl]-(4,4-difluoro-piperidin-1-yl)-methanone,
(4,4-difluoro-piperidin-1-yl)-[5-(4-pyrrolidin-1-yl-piperidine-1-carbonyl)-1-(2,2,2-trifluoro-ethyl)-1H-indol-2-yl]-methanone,
(4,4-difluoro-piperidin-1-yl)-[1-isopropyl-5-(4-pyrrolidin-1-yl-piperidine-1-carbonyl)-1H-indol-2-yl]-methanone,
[1-(2-chloro-pyridin-4-yl)-5-(4-pyrrolidin-1-yl-piperidine-1-carbonyl)-1H-indol-2-yl]-(4,4-difluoro-piperidin-1-yl)-methanone,
[1-(3-chloro-phenyl)-5-(4-pyrrolidin-1-yl-piperidine-1-carbonyl)-1H-indol-2-yl]-(4,4-difluoro-piperidin-1-yl)-methanone,
(4,4-difluoro-piperidin-1-yl)-[5-(4-pyrrolidin-1-yl-piperidine-1-carbonyl)-1-(3-trifluoromethyl-phenyl)-1H-indol-2-yl]-methanone,
[1-(6-chloro-pyridin-3-yl)-5-(4-pyrrolidin-1-yl-piperidine-1-carbonyl)-1H-indol-2-yl]-(4,4-difluoro-piperidin-1-yl)-methanone,
[1-cyclopropylmethyl-5-(4-morpholin-4-yl-piperidine-1-carbonyl)-1H-indol-2-yl]-(4,4-difluoro-piperidin-1-yl)-methanone,
(4,4-difluoro-piperidin-1-yl)-[5-(4-morpholin-4-yl-piperidine-1-carbonyl)-1-(2,2,2-trifluoro-ethyl)-1H-indol-2-yl]-methanone,
(4,4-difluoro-piperidin-1-yl)-[1-isopropyl-5-(4-morpholin-4-yl-piperidine-1-carbonyl)-1H-indol-2-yl]-methanone,
[1-(3-chloro-phenyl)-5-(4-morpholin-4-yl-piperidine-1-carbonyl)-1H-indol-2-yl]-(4,4-difluoro-piperidin-1-yl)-methanone,
(4,4-difluoro-piperidin-1-yl)-[5-(4-morpholin-4-yl-piperidine-1-carbonyl)-1-(3-trifluoromethyl-phenyl)-1H-indol-2-yl]-methanone,
[1-(6-chloro-pyridin-3-yl)-5-(4-morpholin-4-yl-piperidine-1-carbonyl)-1H-indol-2-yl]-(4,4-difluoro-piperidin-1-yl)-methanone,
[1-cyclopropylmethyl-5-(4-isopropyl-piperazine-1-carbonyl)-1H-indol-2-yl]-(4-methoxy-piperidin-1-yl)-methanone,
[5-(4-isopropyl-piperazine-1-carbonyl)-1-(2,2,2-trifluoro-ethyl)-1H-indol-2-yl]-(4-methoxy-piperidin-1-yl)-methanone,
[1-(3-chloro-phenyl)-5-(4-isopropyl-piperazine-1-carbonyl)-1H-indol-2-yl]-(4-methoxy-piperidin-1-yl)-methanone,
[5-(4-isopropyl-piperazine-1-carbonyl)-1-(3-trifluoromethyl-phenyl)-1H-indol-2-yl]-(4-methoxy-piperidin-1-yl)-methanone,
[1-(2-chloro-pyridin-4-yl)-5-(4-isopropyl-piperazine-1-carbonyl)-1H-indol-2-yl]-(4-methoxy-piperidin-1-yl)-methanone,
(1,4-dioxa-8-aza-spiro[4.5]dec-8-yl)-[5-(4-isopropyl-piperazine-1-carbonyl)-1H-indol-2-yl]-methanone,
[1-cyclopropylmethyl-5-(4-isopropyl-piperazine-1-carbonyl)-1H-indol-2-yl]-(1,4-dioxa-8-aza-spiro[4.5]dec-8-yl)-methanone,
(1,4-dioxa-8-aza-spiro[4.5]dec-8-yl)-[5-(4-isopropyl-piperazine-1-carbonyl)-1-(2,2,2-trifluoro-ethyl)-1H-indol-2-yl]-methanone,
[1-(3-chloro-phenyl)-5-(4-isopropyl-piperazine-1-carbonyl)-1H-indol-2-yl]-(1,4-dioxa-8-aza-spiro[4.5]dec-8-yl)-methanone,
(1,4-dioxa-8-aza-spiro[4.5]dec-8-yl)-[5-(4-isopropyl-piperazine-1-carbonyl)-1-(3-trifluoromethyl-phenyl)-1H-indol-2-yl]-methanone,
[1-(2-chloro-pyridin-4-yl)-5-(4-isopropyl-piperazine-1-carbonyl)-1H-indol-2-yl]-(1,4-dioxa-8-aza-spiro[4.5]dec-8-yl)-methanone,

[5-(4-cyclobutyl-piperazine-1-carbonyl)-1H-indol-2-yl]-(1,1-dioxothiomorpholin-4-yl)-methanone,
[5-(4-cyclobutyl-piperazine-1-carbonyl)-1-cyclopropylmethyl-1H-indol-2-yl]-(1,1-dioxothiomorpholin-4-yl)-methanone,
[5-(4-cyclobutyl-piperazine-1-carbonyl)-1-(2,2,2-trifluoro-ethyl)-1H-indol-2-yl]-(1,1-dioxothiomorpholin-4-yl)-methanone,
[5-(4-cyclobutyl-piperazine-1-carbonyl)-1-isopropyl-1H-indol-2-yl]-(1,1-dioxothiomorpholin-4-yl)-methanone,
[5-(4-cyclobutyl-piperazine-1-carbonyl)-2-(1,1-dioxothiomorpholine-4-carbonyl)-indol-1-yl]-acetonitrile,
[5-(4-cyclobutyl-piperazine-1-carbonyl)-1-(3-fluoro-phenyl)-1H-indol-2-yl]-(1,1-dioxothiomorpholin-4-yl)-methanone,
[5-(4-cyclobutyl-piperazine-1-carbonyl)-1-m-tolyl-1H-indol-2-yl]-(1,1-dioxothiomorpholin-4-yl)-methanone,
[1-(3-chloro-phenyl)-5-(4-cyclobutyl-piperazine-1-carbonyl)-1H-indol-2-yl]-(1,1-dioxothiomorpholin-4-yl)-methanone,
[5-(4-cyclobutyl-piperazine-1-carbonyl)-1-(3-trifluoromethyl-phenyl)-1H-indol-2-yl]-(1,1-dioxothiomorpholin-4-yl)-methanone,
3-[5-(4-cyclobutyl-piperazine-1-carbonyl)-2-(1,1-dioxothiomorpholine-4-carbonyl)-indol-1-yl]-benzonitrile,
[5-(4-cyclobutyl-piperazine-1-carbonyl)-1-(3-methanesulfonyl-phenyl)-1H-indol-2-yl]-(1,1-dioxothiomorpholin-4-yl)-methanone,
[5-(4-cyclobutyl-piperazine-1-carbonyl)-1-(3-trifluoromethoxy-phenyl)-1H-indol-2-yl]-(1,1-dioxothiomorpholin-4-yl)-methanone,
[1-(2-chloro-pyridin-4-yl)-5-(4-cyclobutyl-piperazine-1-carbonyl)-1H-indol-2-yl]-(1,1-dioxothiomorpholin-4-yl)-methanone,
[1-(6-chloro-pyridin-3-yl)-5-(4-cyclobutyl-piperazine-1-carbonyl)-1H-indol-2-yl]-(1,1-dioxothiomorpholin-4-yl)-methanone,
[5-(4-cyclobutyl-piperazine-1-carbonyl)-1-(4-methanesulfonyl-phenyl)-1H-indol-2-yl]-(1,1-dioxo-thiomorpholin-4-yl)-methanone,
(1,1-dioxothiomorpholin-4-yl)-[1-isopropyl-5-(4-isopropyl-piperazine-1-carbonyl)-1H-indol-2-yl]-methanone,
[2-(1,1-dioxothiomorpholine-4-carbonyl)-5-(4-isopropyl-piperazine-1-carbonyl)-indol-1-yl]-acetonitrile,
(1,1-dioxo-thiomorpholin-4-yl)-[5-(4-isopropyl-piperazine-1-carbonyl)-1-m-tolyl-1H-indol-2-yl]-methanone,
(1,1-dioxothiomorpholin-4-yl)-[1-(3-fluoro-phenyl)-5-(4-isopropyl-piperazine-1-carbonyl)-1H-indol-2-yl]-methanone,
(1,1-dioxothiomorpholin-4-yl)-[5-(4-isopropyl-piperazine-1-carbonyl)-1-(4-methanesulfonyl-phenyl)-1H-indol-2-yl]-methanone,
[1-(2-chloro-pyridin-4-yl)-5-(4-isopropyl-piperazine-1-carbonyl)-1H-indol-2-yl]-(1,1-dioxothiomorpholin-4-yl)-methanone
[1-(6-chloro-pyridin-3-yl)-5-(4-isopropyl-piperazine-1-carbonyl)-1H-indol-2-yl]-(1,1-dioxothiomorpholin-4-yl)-methanone,
(1,1-dioxothiomorpholin-4-yl)-[5-(4-isopropyl-piperazine-1-carbonyl)-1-(3-methanesulfonyl-phenyl)-1H-indol-2-yl]-methanone,
(1,1-dioxothiomorpholin-4-yl)-[5-(4-isopropyl-piperazine-1-carbonyl)-1-pyrimidin-5-yl-1H-indol-2-yl]-methanone,
[1-(2-chloro-pyridin-4-yl)-5-(4-isopropyl-piperazine-1-carbonyl)-1H-indol-2-yl]-(4,4-difluoro-piperidin-1-yl)-methanone,
[6-chloro-2-(4,4-difluoro-piperidine-1-carbonyl)-1H-indol-5-yl]-(4-isopropyl-piperazin-1-yl)-methanone,
[4-chloro-2-(4,4-difluoro-piperidine-1-carbonyl)-1H-indol-5-yl]-(4-isopropyl-piperazin-1-yl)-methanone,
[6-chloro-1-(2-chloro-pyridin-4-yl)-5-(4-isopropyl-piperazine-1-carbonyl)-1H-indol-2-yl]-(4,4-difluoro-piperidin-1-yl)-methanone,
[4-chloro-1-(2-chloro-pyridin-4-yl)-5-(4-isopropyl-piperazine-1-carbonyl)-1H-indol-2-yl]-(4,4-difluoro-piperidin-1-yl)-methanone,
[6-chloro-1-isopropyl-5-(4-isopropyl-piperazine-1-carbonyl)-1H-indol-2-yl]-(4,4-difluoro-piperidin-1-yl)-methanone,
[7-chloro-2-(4,4-difluoro-piperidine-1-carbonyl)-1H-indol-5-yl]-(4-isopropyl-piperazin-1-yl)-methanone,
[7-chloro-5-(4-isopropyl-piperazine-1-carbonyl)-1H-indol-2-yl]-(4-isopropyl-piperazin-1-yl)-methanone,
[7-chloro-1-isopropyl-5-(4-isopropyl-piperazine-1-carbonyl)-1H-indol-2-yl]-(4,4-difluoro-piperidin-1-yl)-methanone,
[5-(3-dimethylamino-piperidine-1-carbonyl)-1H-indol-2-yl]-morpholin-4-yl-methanone,
[5-(3-dimethylamino-piperidine-1-carbonyl)-1-isopropyl-1H-indol-2-yl]-morpholin-4-yl-methanone,
(4,4-difluoro-piperidin-1-yl)-[5-(3-dimethylamino-piperidine-1-carbonyl)-1-isopropyl-1H-indol-2-yl]-methanone,
[5-(3-dimethylamino-piperidine-1-carbonyl)-1-isopropyl-1H-indol-2-yl]-(1,1-dioxo-thiomorpholin-4-yl)-methanone,
[1-isopropyl-5-(4-isopropyl-[1,4]diazepane-1-carbonyl)-1H-indol-2-yl]-morpholin-4-yl-methanone,
(4,4-difluoro-piperidin-1-yl)-[1-isopropyl-5-(4-isopropyl-[1,4]diazepane-1-carbonyl)-1H-indol-2-yl]-methanone,
[5-(4-sec-butyl-[1,4]diazepane-1-carbonyl)-1H-indol-2-yl]-morpholin-4-yl-methanone,
(1,1-dioxo-thiomorpholin-4-yl)-[1-isopropyl-5-(4-isopropyl-[1,4]diazepane-1-carbonyl)-1H-indol-2-yl]-methanone,
[5-(4-isopropyl-[1,4]diazepane-1-carbonyl)-1H-indol-2-yl]-morpholin-4-yl-methanone,
(4,4-difluoro-piperidin-1-yl)-[5-(4-isopropyl-[1,4]diazepane-1-carbonyl)-1H-indol-2-yl]-methanone,
(1,1-dioxo-thiomorpholin-4-yl)-[5-(4-isopropyl-[1,4]diazepane-1-carbonyl)-1H-indol-2-yl]-methanone,
[5-(4-cyclopropyl-[1,4]diazepane-1-carbonyl)-1H-indol-2-yl]-(1,1-dioxo-thiomorpholin-4-yl)-methanone, and pharmaceutically acceptable salts thereof.

Especially preferred are the following compounds:
[5-(4-cyclopentyl-piperazine-1-carbonyl)-1H-indol-2-yl]-morpholin-4-yl-methanone,
[5-(4-isopropyl-piperazine-1-carbonyl)-1-(2,2,2-trifluoro-ethyl)-1H-indol-2-yl]-morpholin-4-yl-methanone,
[5-(4-cyclobutyl-piperazine-1-carbonyl)-1-(2,2,2-trifluoro-ethyl)-1H-indol-2-yl]-morpholin-4-yl-methanone,
[5-(4-cyclopentyl-piperazine-1-carbonyl)-1-(2,2,2-trifluoro-ethyl)-1H-indol-2-yl]-morpholin-4-yl-methanone,
(4,4-difluoro-piperidin-1-yl)-[5-(4-isopropyl-piperazine-1-carbonyl)-1-(3-trifluoromethyl-phenyl)-1H-indol-2-yl]-methanone,
[1-(3-chloro-phenyl)-5-(4-isopropyl-piperazine-1-carbonyl)-1H-indol-2-yl]-(1,1-dioxo-thiomorpholin-4-yl)-methanone,
(1,1-dioxo-thiomorpholin-4-yl)-[5-(4-isopropyl-piperazine-1-carbonyl)-1-(3-trifluoromethyl-phenyl)-1H-indol-2-yl]-methanone,

[5-(4-isopropyl-piperazine-1-carbonyl)-1-(3-trifluoromethyl-phenyl)-1H-indol-2-yl]-morpholin-4-yl-methanone,
(4,4-difluoro-piperidin-1-yl)-[1-(3-fluoro-phenyl)-5-(4-isopropyl-piperazine-1-carbonyl)-1H-indol-2-yl]-methanone,
3-[5-(4-cyclobutyl-piperazine-1-carbonyl)-2-(4,4-difluoro-piperidine-1-carbonyl)-indol-1-yl]-benzonitrile,
[5-(4-cyclobutyl-piperazine-1-carbonyl)-1-(3-trifluoromethyl-phenyl)-1H-indol-2-yl]-(4,4-difluoro-piperidin-1-yl)-methanone,
[5-(4-cyclobutyl-piperazine-1-carbonyl)-1-isopropyl-1H-indol-2-yl]-(4,4-difluoro-piperidin-1-yl)-methanone,
[1-(2-chloro-pyridin-4-yl)-5-(4-isopropyl-piperazine-1-carbonyl)-1H-indol-2-yl]-(4,4-difluoro-piperidin-1-yl)-methanone,
[1-isopropyl-5-(4-isopropyl-[1,4]diazepane-1-carbonyl)-1H-indol-2-yl]-morpholin-4-yl-methanone,
(4,4-difluoro-piperidin-1-yl)-[1-isopropyl-5-(4-isopropyl-[1,4]diazepane-1-carbonyl)-1H-indol-2-yl]-methanone,
(1,1-dioxo-thiomorpholin-4-yl)-[1-isopropyl-5-(4-isopropyl-[1,4]diazepane-1-carbonyl)-1H-indol-2-yl]-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of formula II

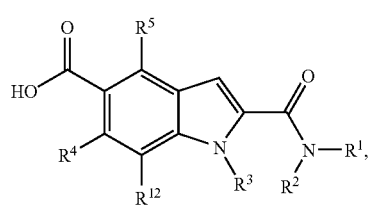

II wherein $R^1$, $R^2$, $R^4$, $R^{12}$ and $R^5$ are as defined herein before and $R^3$ is hydrogen, with an amine of the formula IIIA or IIIB

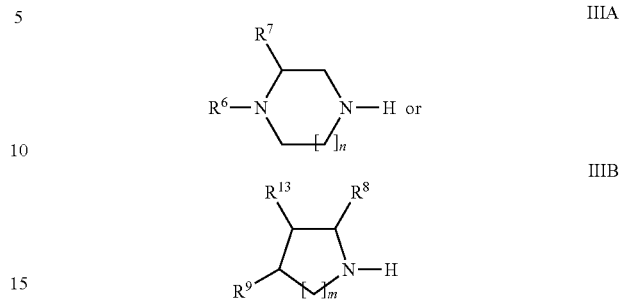

wherein $R^6$, $R^7$, $R^8$, $R^9$, $R^{13}$, m and n are as defined herein before, in the presence of a coupling reagent under basic conditions to obtain a compound of the formula IA

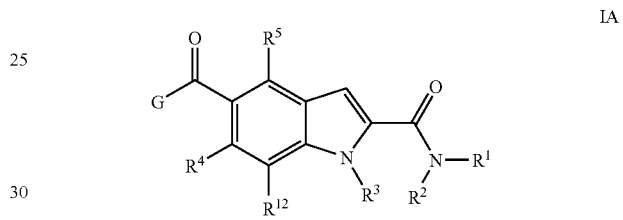

wherein $R^1$, $R^2$, $R^4$, $R^5$, $R^{12}$ and G are as defined herein before and $R^3$ is hydrogen, and optionally transferring into a compound of formula IB

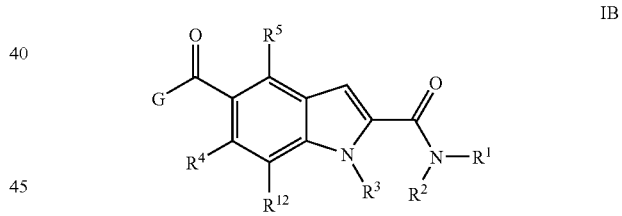

wherein $R^3$ is a group as defined herein before other than hydrogen, and if desired,
converting the compound obtained into a pharmaceutically acceptable acid addition salt.

Appropriate coupling reagents are for example N,N-carbonyldiimidazole (CDI) or 1-hydroxy-1,2,3-benzotriazole (HOBT). The reaction is carried out in a suitable solvent such as for example dimethylformamide (DMF) or dioxane in the presence of an appropriate base. Preferred is a base such as triethylamine or diisopropylethylamine.

Transferring into a compound of formula IB means treating the compound of formula IA with a suitable base in a suitable solvent under anhydrous conditions (e.g. sodium hydride in DMF) and reacting the intermediate anion with an alkylating or acylating agent $R^3$-X, wherein X signifies a leaving group such as e.g. iodide, bromide, methanesulfonate or chloride, to obtain a compound of formula IB wherein $R^3$ signifies lower alkyl, lower hydroxyalkyl, lower alkoxyalkyl, lower halogenalkyl, lower cycloalkylalkyl, lower alkanoyl, lower cyanoalkyl, lower alkylsulfonyl or phenylsulfonyl, or alternatively, transferring into a compound of formula IB means reacting a compound of formula IA with an optionally substituted phenylboronic acid using an appropriate catalyst (e.g. copper(II) acetate) and base (e.g. pyridine) in a suitable solvent like, e.g. dichloromethane, to obtain a compounds of formula IB where $R^3$ signifies a phenyl or a substituted phenyl group.

In more detail, the compounds of formula I can be manufactured by the methods given below, by the methods given in the examples or by analogous methods. The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

Starting materials are either commercially available or can be prepared by methods analogous to the methods given below, by methods described in references cited in the description or in the examples, or by methods known in the art.

Compounds of the general formula IA and IB can be prepared according to scheme 1 by a process where the 2-carbethoxyindole-5-carboxylic acid of formula A (prepared according to, e.g. Lindwall, H. G.; Mantell, G. J.; J. Org. Chem. 1953, 18, 345) is first reacted with an amine of formula III (either commercially available or accessible by methods described in references or by methods known in the art) to give intermediate B. The coupling of carboxylic acids with amines (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. dimethylformamide (DMF) or dioxane in the presence of an appropriate base (e.g. triethylamine or diisopropylethylamine). The ester functionality in intermediates B is cleaved under basic (e.g. with lithium hydroxide in polar solvents such as, e.g. methanol, water or THF or mixtures of said solvents) or under acidic conditions (e.g. using concentrated hydrochloric acid in THF) and subsequent transformation of the resulting either lithium or hydrochloride salt of intermediate C to compounds of the general formula IA applying the before-mentioned methods.

Scheme 1

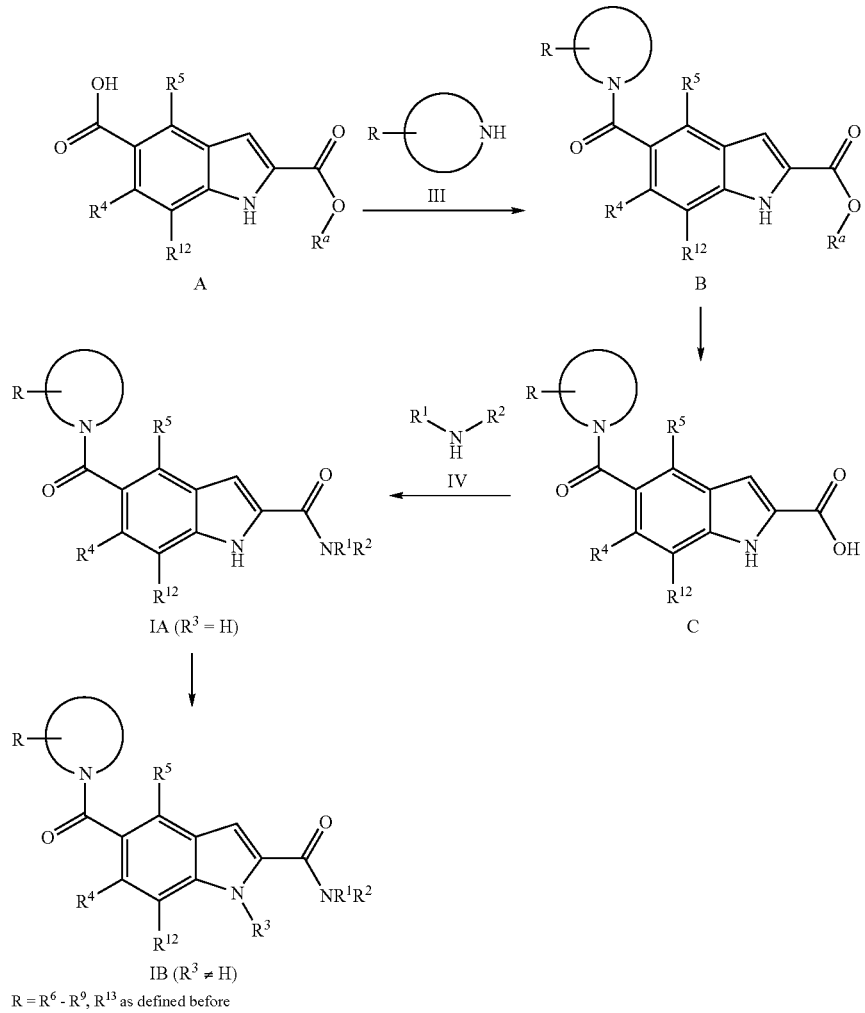

R = $R^6$ - $R^9$, $R^{13}$ as defined before

Intermediates of formula IB can be obtained for example through treatment of intermediates of formula IA with a suitable base in a suitable solvent under anhydrous conditions (e.g. sodium hydride in DMF) and reacting the intermediate anion with an alkylating or acylating agent $R^3$-X such as, e.g. methyl iodide, 2-bromopropane, 2,2,2-trifluoroethyl-methanesulfonate, methanesulfonyl- or phenylsulfonylchloride. In those cases $R^3$ signifies a methyl, trifluoromethyl, isopropyl or an alkyl- or arylsulfonyl group and X signifies a leaving group such as, e.g. iodide, bromide, methanesulfonate or chloride. Compounds of formula IB where $R^3$ signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula IA are reacted with an optionally substituted phenylboronic acid using an appropriate catalyst (e.g. copper(II) acetate) and base (e.g. pyridine) in a suitable solvent like, e.g. dichloromethane. $R^a$ in Scheme 1 is an alkyl group, preferably a lower alkyl group, preferably methyl or ethyl.

employing the usage of coupling reagents (e.g. N,N-carbonyldiimidazole).

Intermediates of formula F can be obtained for example through treatment of intermediates of formula E with a suitable base in a suitable solvent under anhydrous conditions (e.g. sodium hydride in tetrahydrofuran) and reacting the intermediate anion with an alkylating or acylating agent $R^3$-X such as, e.g. methyl iodide, 2-bromopropane, 2,2,2-trifluoroethyl-methanesulfonate, methanesulfonyl- or phenylsulfonylchloride. In those cases $R^3$ signifies a methyl, trifluoromethyl, isopropyl or an alkyl- or arylsulfonyl group and X signifies a leaving group such as, e.g. iodide, bromide, methanesulfonate or chloride. Compounds of formula F where $R^3$ signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula E are reacted with an optionally substituted phenyl-

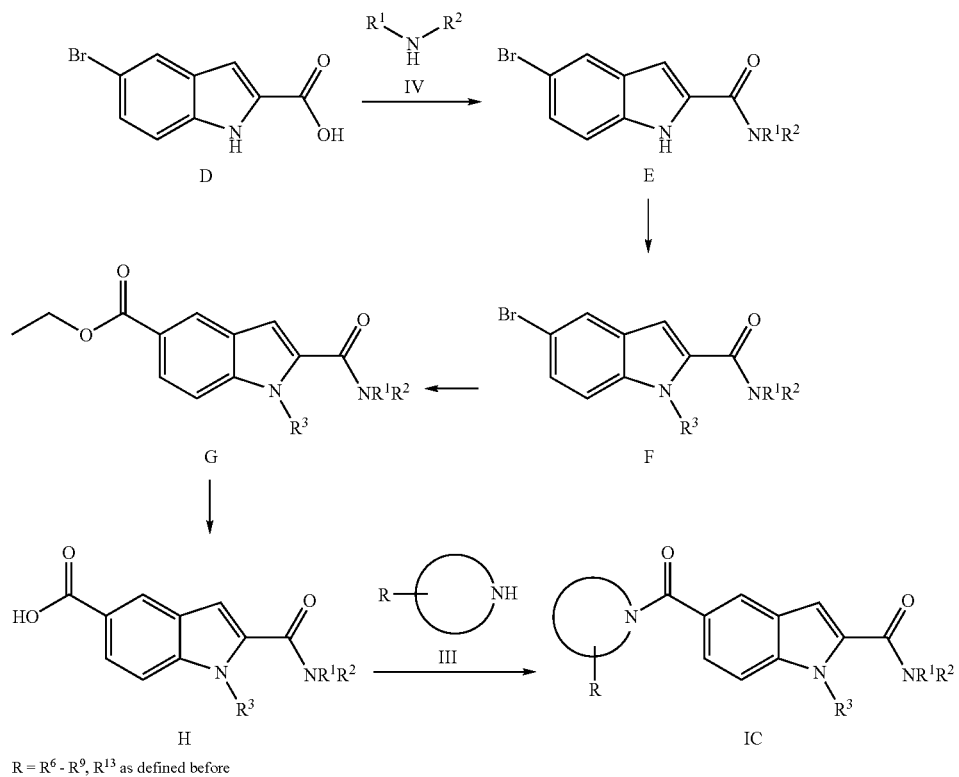

Scheme 2

R = $R^6$ - $R^9$, $R^{13}$ as defined before

Compounds of general formula IC can be prepared according to Scheme 2 by a process involving the reaction of 5-bromoindole-2-carboxylic acid with an amine of formula IV (either commercially available or accessible by methods described in references or by methods known in the art) to give intermediate E. The coupling of carboxylic acids with amines is widely described in literature (e.g. Comprehensive Organic Transformations: A Guide to Functional Group Preparations, 2nd Edition, Richard C. Larock. John Wiley & Sons, New York, N.Y. 1999) and can be accomplished by boronic acid using an appropriate catalyst (e.g. copper(II) acetate) and base (e.g. pyridine) in a suitable solvent (e.g. dichloromethane).

Intermediates of formula G can be obtained for example through treatment of intermediates of formula F with a palladium source (e.g. palladium acetate) and suitable ligand (e.g. 1,3-(diphenylphosphino)ferrocene) in a suitable solvent or solvent mixture (e.g. 1:1 v:v dimethylsulfoxide/ethanol) under carbon monoxide atmosphere (at, e.g. 1 Atmosphere) by processes known to those skilled in the art and described in literature (e.g. Kumar, K. Org. Letters 2004, 6, 4).

The ester functionality in intermediates G is cleaved under basic (e.g. with lithium hydroxide in polar solvents such as, e.g. methanol, water or THF or mixtures of said solvents) or under acidic conditions (e.g. using concentrated hydrochloric acid in THF) and subsequent transformation of the resulting either lithium salt or salt-free intermediate H to compounds of the general formula IC applying the before-mentioned methods.

Scheme 3

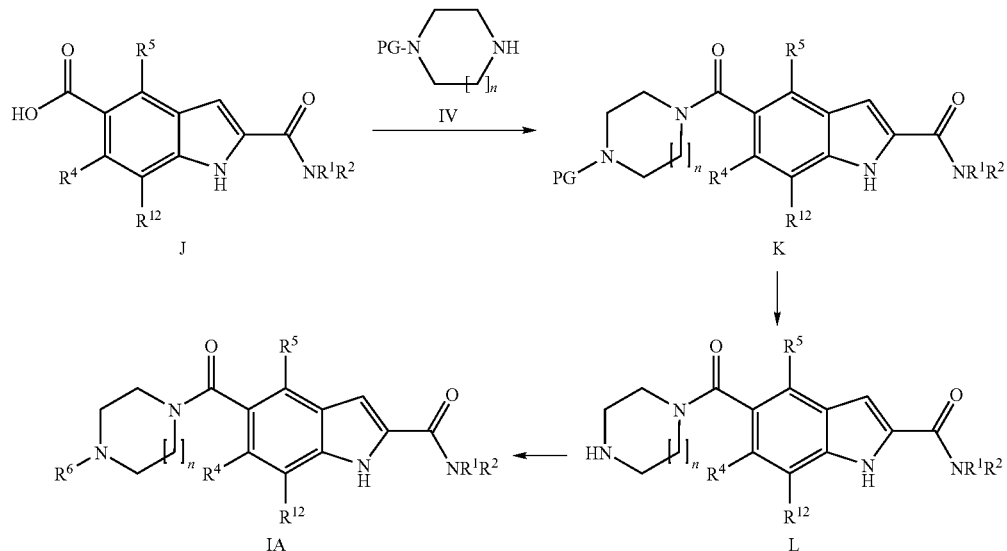

In cases of substituents G1 where the substituent $R^6$ is not already present in the corresponding piperidine or homopiperidine substituent IV, $R^6$ can be introduced as exemplified in Scheme 3. Amide coupling of intermediates J with protected (e.g. with a tert-butoxycarbonyl protective group) and optionally substituted piperidines or homopiperidines leads to intermediates K, which in turn can be deprotected (e.g. a tert-butoxycarbonyl group by using, e.g. trifluoroacetic acid in dichloromethane) to give intermediates L. Alkylation of the free amine functionality in intermediates K by employing methods described in references or by methods known in the art such as, e.g. reductive amination (e.g. F. Zaragoza, et. al, J. Med. Chem. 2004, 47, 2833) gives compounds of the general formula IA.

The compounds of formula I can contain several asymmetric centers and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbents or eluant).

Scheme 4

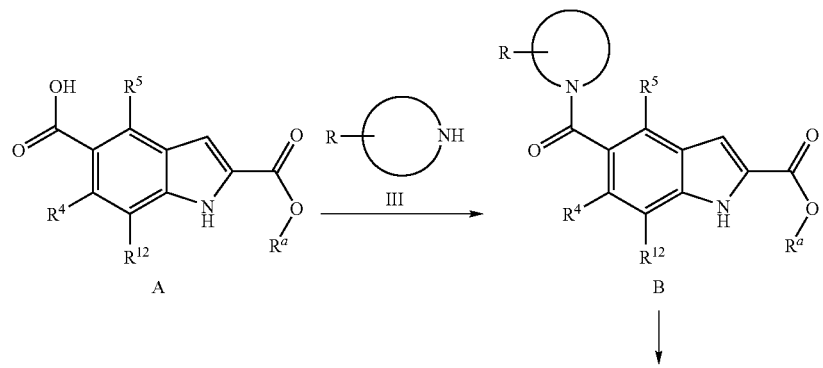

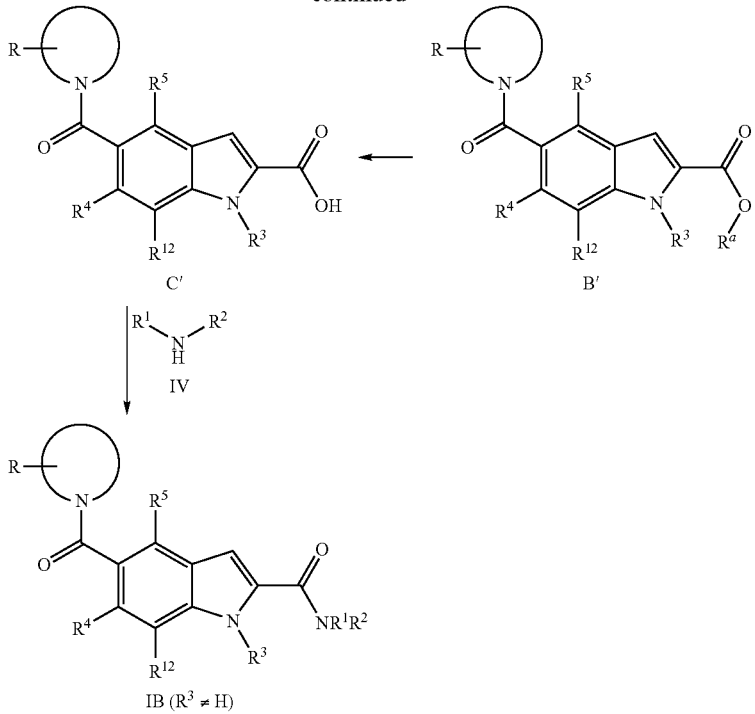

Alternatively, compounds of general structure IB may be prepared according to scheme 4. Intermediates of formula B' can be obtained for example through treatment of intermediates of formula B with a suitable base in a suitable solvent under anhydrous conditions (e.g. sodium hydride in DMF or caesium carbonate in acetonitrile) and reacting the intermediate anion with an alkylating or acylating agent $R^3$-X such as, e.g. methyl iodide, 2-bromopropane, isopropylmethanesulfonate, 2,2,2-trifluoroethyl-methanesulfonate, methanesulfonyl- or phenylsulfonylchloride. In those cases $R^3$ signifies a methyl, trifluoromethyl, isopropyl or an alkyl- or arylsulfonyl group and X signifies a leaving group such as, e.g. iodide, bromide, methanesulfonate or chloride. Compounds of formula B' where $R^3$ signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula B are reacted with an optionally substituted phenylboronic acid using an appropriate catalyst (e.g. copper(II) acetate) and base (e.g. pyridine) in a suitable solvent like, e.g. dichloromethane. $R^a$ in Scheme 4 is an alkyl group, preferably a lower alkyl group, preferably methyl or ethyl.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-Methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R)α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM MgCl$_2$x6H$_2$O pH 7.4. Washing Buffer: 50 mM Tris-HCl pH 7.4 and 5 mM MgCl$_2$x6H$_2$O and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-

RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 5 | 28.7 |
| Example 84 | 35.6 |
| Example 97 | 13.4 |
| Example 150 | 25.2 |
| Example 221 | 22.6 |
| Example 245 | 41.0 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Example 1

[2-(1,1-Dioxo-thiomorpholine-4-carbonyl)-1H-indol-5-yl]-(4-isopropyl-piperazin-1-yl)-methanone To the solution of 0.20 g (0.57 mmol) 5-(4-isopropyl-piperazine-1-carbonyl)-1H-indole-2-carboxylic acid 1:1 hydrochloride in 2 mL N,N-dimethylformamide, 0.19 g (0.60 mmol) O-(benzotriazol-1-yl)-N,N,N',N'-tetramethyluronium tetrafluoroborate (commercially available), 82 mg (0.60 mmol) thiomorpholine 1,1-dioxide (commercially available) and 0.58 mL (0.44 g, 3.4 mmol) N,N-diisopropylethylamine were added. After 1 h the solution was poured on saturated aqueous sodium bicarbonate solution, the phases were separated and the aqueous phase was extracted three times with ethyl acetate. The combined organic layers were washed three times with water followed by brine, dried over magnesium sulfate, filtered and evaporated. The residue was flash-chromatographed twice on silica gel with dichloromethane:

methanol:ammonia (12:1:0.1 v/v) as eluant to give 0.13 g (64%) of the desired compound as a light brown solid.

MS (ISP): 433.3 (M+H$^+$)

Intermediate 1

5-(4-Isopropyl-piperazine-1-carbonyl)-1H-indole-2-carboxylic acid ethyl ester

To the solution of 5.0 g (21.4 mmol) 1H-indole-2,5-dicarboxylic acid 2-ethyl ester (prepared according to J. Org. Chem. 1953, 18, 345-57) in 50 mL N,N-dimethylformamide, 8.6 g (26.8 mmol) O-(benzotriazol-1-yl)-N,N,N',N'-tetramethyluronium tetrafluoroborate (commercially available) were added. After 10 min., 3.44 g (26.8 mmol) 1-isopropylpiperazine (commercially available) and 18.3 mL (13.9 g, 107.4 mmol) N,N-diisopropylethylamine were added. After 45 min. the reaction mixture was poured on saturated aqueous sodium bicarbonate solution and was extracted three times with ethyl acetate. The combined organic layers were washed three times with water followed by brine, dried over magnesium sulfate, filtered and evaporated. The residue was flash-chromatographed on silica gel with dichloromethane:methanol:ammonia (9:1:0.1 v/v) and ethyl acetate:methanol (9:1) as eluant to give 5.5 g (74%) of the desired compound as a light yellow solid.

MS (ISP): 344.3 (M+H$^+$)

5-(4-Isopropyl-piperazine-1-carbonyl)-1H-indole-2-carboxylic acid 1:1 hydrochloride The solution of 2.8 g (8.1 mmol) 5-(4-isopropyl-piperazine-1-carbonyl)-1H-indole-2-carboxylic acid ethyl ester in 110 mL tetrahydrofuran, 0.24 g (10.1 mmol) lithium hydroxide was added followed by 55 mL of water. The resulting yellow solution was stirred under reflux for 1.75 hours. The organic solvent was evaporated and the remaining turbid aqueous residue was treated with 4 M hydrochloric acid until a pH of 2 was reached. The volatile components were to dryness to give 3 g of the desired compound as the hydrochloride salt containing lithium chloride. This material was pure enough for the next step without further purification.

MS (ISP): 316.1 (M+H$^+$)

Intermediate 2

5-(4-Cyclopentyl-piperazine-1-carbonyl)-1H-indole-2-carboxylic acid ethyl ester

The title compound was synthesized in analogy to example 1, intermediate 1 a), from 1H-indole-2,5-dicarboxylic acid 2-ethyl ester, O-(benzotriazol-1-yl)-N,N,N',N'-tetramethyluronium tetrafluoroborate (commercially available), 1-cyclopentylpiperazine (commercially available) and N,N-diisopropylethylamine in N,N-dimethylformamide, to give the desired product as a light brown solid (74%).

MS (ISP): 344.3 (M+H$^+$)

5-(4-Cyclopentyl-piperazine-1-carbonyl)-1H-indole-2-carboxylic acid 1:1 hydrochloride The title compound was synthesized in analogy to example 1, intermediate 1 b), from 5-(4-cyclopentyl-piperazine-1-carbonyl)-1H-indole-2-carboxylic acid ethyl ester, to give the desired product as a light brown solid (60%).

MS (ISP): 342.3 (M+H$^+$)

Example 2

[5-(4-Cyclopentyl-piperazine-1-carbonyl)-1H-indol-2-yl]-pyrrolidin-1-yl-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), pyrrolidine (commercially available) and N,N-diisopropylethylamine in N,N-dimethyl-formamide to give the desired product.

MS (TIC): 395.1 (M+H$^+$)

Example 3

[5-(4-Cyclopentyl-piperazine-1-carbonyl)-1H-indol-2-yl]-(2-methyl-pyrrolidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 2-methyl-pyrrolidine (commercially available) and N,N-diisopropylethylamine in N,N-dimethyl-formamide to give the desired product after purification by preparative HPLC on reversed phase eluting with a gradient formed from acetonitrile/water/formic acid.

MS (TIC): 409.3 (M+H$^+$)

Example 4

[5-(4-Cyclopentyl-piperazine-1-carbonyl)-1H-indol-2-yl]-(2-isopropyl-pyrrolidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 2-isopropylpyrrolidine (commercially available) and N,N-diisopropylethylamine in N,N-dimethyl-formamide to give the desired product after purification by preparative HPLC on reversed phase eluting with a gradient formed from acetonitrile/water/formic acid.

MS (TIC): 437.2 (M+H$^+$)

Example 5

[5-(4-Cyclopentyl-piperazine-1-carbonyl)-1H-indol-2-yl]-piperidin-1-yl-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 409.3 (M+H$^+$)

Example 6

[5-(4-Cyclopentyl-piperazine-1-carbonyl)-1H-indol-2-yl]-(4-methyl-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-methyl piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 423.2 $(M+H^+)$

Example 7

[5-(4-Cyclopentyl-piperazine-1-carbonyl)-1H-indol-2-yl]-(4-methoxy-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-methoxy piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 439.3 $(M+H^+)$

Example 8

[5-(4-Cyclopentyl-piperazine-1-carbonyl)-1H-indol-2-yl]-(4,4-difluoro-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 2,4-difluoro piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 445.3 $(M+H^+)$

Example 9

[5-(4-Cyclopentyl-piperazine-1-carbonyl)-1H-indol-2-yl]-(4-hydroxy-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 2,4-difluoro piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 425.1 $(M+H^+)$

Example 10

[5-(4-Cyclopentyl-piperazine-1-carbonyl)-1H-indol-2-yl]-morpholin-4-yl-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), morpholine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 411.2 $(M+H^+)$

Example 11

[5-(4-Cyclopentyl-piperazine-1-carbonyl)-1H-indol-2-yl]-thiomorpholin-4-yl-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), thiomorpholine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 427.1 $(M+H^+)$

Example 12

[5-(4-Cyclopentyl-piperazine-1-carbonyl)-1H-indol-2-yl]-(3-fluoro-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 3-fluoropiperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 427.2 $(M+H^+)$

Example 13

[5-(4-Cyclopentyl-piperazine-1-carbonyl)-1H-indol-2-yl]-(4-trifluoromethyl-piperidin-1-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-trifluoromethylpiperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 477.1 $(M+H^+)$

Example 14

[5-(4-Cyclopentyl-piperazine-1-carbonyl)-1H-indol-2-yl]-(3,4-dihydro-1H-isoquinolin-2-yl) - methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 3,4-dihydro-1H-isoquinoline (commercially available) and N,N-diisopropylethylamine in N,N-dimethylformamide to give the desired product after purification by preparative HPLC on reversed phase eluting with a gradient formed from acetonitrile/water/formic acid.

MS (TIC): 457.3 (M+H$^+$)

Example 15

5-(4-Cyclopentyl-piperazine-1-carbonyl)-1H-indole-2-carboxylic acid benzyl-methyl-amide The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), methylbenzylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 445.3 (M+H$^+$)

Example 16

[5-(4-Isopropyl-piperazine-1-carbonyl)-1H-indol-2-yl]-pyrrolidin-1-yl-methanone

The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), methylbenzylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 369.1 (M+H$^+$)

Example 17

[5-(4-Isopropyl-piperazine-1-carbonyl)-1H-indol-2-yl]-(2-methyl-pyrrolidin-1-yl)-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), methylbenzylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 383.2 (M+H$^+$)

Example 18

[5-(4-Isopropyl-piperazine-1-carbonyl)-1H-indol-2-yl]-(2-isopropyl-pyrrolidin-1-yl) -methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N',N'-tetramethyluronium tetrafluoroborate (commercially available), 2-isopropylpyrrolidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 411.2 (M+H$^+$)

Example 19

[5-(4-Isopropyl-piperazine-1-carbonyl)-1H-indol-2-yl]-piperidin-1-yl-methanone

The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 383.2 (M+H$^+$)

Example 20

[5-(4-Isopropyl-piperazine-1-carbonyl)-1H-indol-2-yl]-(4-methyl-piperidin-1-yl)-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-methyl piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 397.2 (M+H$^+$)

Example 21

[5-(4-Isopropyl-piperazine-1-carbonyl)-1H-indol-2-yl]-(4-methoxy-piperidin-1-yl)-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-methoxy piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 397.2 (M+H$^+$)

Example 22

(4-Hydroxy-piperidin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-hydroxy piperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 399.1 (M+H$^+$)

Example 23

[5-(4-Isopropyl-piperazine-1-carbonyl)-1H-indol-2-yl]-morpholin-4-yl-methanone

The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), morpholine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 385.1 (M+H$^+$)

Example 24

[5-(4-Isopropyl-piperazine-1-carbonyl)-1H-indol-2-yl]-thiomorpholin-4-yl-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), thiomorpholine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 401.2 (M+H$^+$)

Example 25

(3-Fluoro-piperidin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 3-fluoropiperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 401.2 (M+H$^+$)

Example 26

[5-(4-Isopropyl-piperazine-1-carbonyl)-1H-indol-2-yl]-(4-trifluoromethyl-piperidin-1-yl)-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4-trifluoromethylpiperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 451.2 (M+H$^+$)

Example 27

5-(4-Isopropyl-piperazine-1-carbonyl)-1H-indole-2-carboxylic acid benzylamide

The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), benzylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 405.3 (M+H$^+$)

Example 28

5-(4-Isopropyl-piperazine-1-carbonyl)-1H-indole-2-carboxylic acid benzyl-methyl-amide The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), methylbenzylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 419.2 (M+H$^+$)

Example 29

5-(4-Isopropyl-piperazine-1-carbonyl)-1H-indole-2-carboxylic acid cyclopentylamide The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), cyclopentylamine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 383.2 (M+H$^+$)

Example 30

Azepan-1-yl-[5-(4-isopropyl-piperazine-1-carbonyl)-1H-indol-2-yl]-methanone

The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), azepane (commercially available) and N,N-diisopropylethylamine in N,N-dimethylformamide to give the desired product after purification by preparative HPLC on reversed phase eluting with a gradient formed from acetonitrile/water/formic acid.

MS (TIC): 397.2 (M+H$^+$)

Example 31

Azepan-1-yl-[5-(4-cyclopentyl-piperazine-1-carbonyl)-1H-indol-2-yl]-methanone

The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), azepane (commercially available) and N,N-diisopropylethylamine in N,N-dimethylformamide to give the desired product after purification by preparative HPLC on reversed phase eluting with a gradient formed from acetonitrile/water/formic acid.

MS (TIC): 423.2 (M+H$^+$)

Example 32

(4,4-Difluoro-piperidin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide to give the desired product after purification by preparative HPLC on reversed phase eluting with a gradient formed from acetonitrile/water/formic acid.

MS (TIC): 419.2 (M+H$^+$)

Example 33

(3,4-Dihydro-1H-isoquinolin-2-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), 3,4-Dihydro-1H-isoquinoline (commercially available) and N,N-diisopropylethylamine in N,N-dimethylformamide to give the desired product after purification by preparative HPLC on reversed phase eluting with a gradient formed from acetonitrile/water/formic acid.

MS (TIC): 431.3 (M+H$^+$)

Example 34

[5-(4-Cyclopentyl-piperazine-1-carbonyl)-1H-indol-2-yl]-(1,1-dioxo-thiomorpholin-4-yl)-methanone The title compound was synthesized in analogy to example 1, from 5-(4-cyclopentyl-piperazine-1-carbonyl)-1H-indole-2-carboxylic acid 1:1 hydrochloride, O-(benzotriazol-1-yl)-N,N,N',N'-tetramethyluronium tetrafluoroborate (commercially available), thiomorpholine 1,1-dioxide (commercially available) and N,N-diisopropylethylamine in N,N-dimethylformamide to give the desired product as a light yellow solid (58%).

MS (TIC): 459.3 (M+H$^+$)

Example 35

5-(4-Cyclopentyl-piperazine-1-carbonyl)-1H-indole-2-carboxylic acid (4-fluoro-phenyl)-amide The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), 4-fluoroaniline (commercially available) and N,N-diisopropylethylamine in N,N-dimethylformamide, to give the desired product as a yellow solid (43%).

MS (TIC): 435.2 (M+H$^+$)

Example 36

5-(4-Cyclopentyl-piperazine-1-carbonyl)-1H-indole-2-carboxylic acid (4-fluoro-phenyl)-methyl-amide The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), 4-fluoro-N-methylaniline (commercially available) and N,N-diisopropylethylamine in N,N-dimethylformamide, to give the desired product as a yellow solid (44%).

MS (TIC): 449.2 (M+H$^+$)

Example 37

5-(4-Cyclopentyl-piperazine-1-carbonyl)-1H-indole-2-carboxylic acid (2,6-dimethyl-phenyl)-amide The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), 2,6-dimethylaniline (commercially available) and N,N-diisopropylethylamine in N,N-dimethylformamide, to give the desired product as a yellow solid (22%).

MS (TIC): 445.2 (M+H$^+$)

Example 38

5-(4-Cyclopentyl-piperazine-1-carbonyl)-1H-indole-2-carboxylic acid (2,4,6-trimethyl-phenyl)-amide The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), 2,4,6-trimethylaniline (commercially available) and N,N-diisopropylethylamine in N,N-dimethylformamide, to give the desired product as a light yellow solid (7%).
MS (TIC): 459.3 (M+H$^+$)

Example 39

5-(4-Cyclopentyl-piperazine-1-carbonyl)-1H-indole-2-carboxylic acid (2-fluoro-phenyl)-amide The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), 2-fluoroaniline (commercially available) and N,N-diisopropylethylamine in N,N-dimethylformamide, to give the desired product as a light yellow solid (6%).
MS (TIC): 435.2 (M+H$^+$)

Example 40

(4-Cyclopentyl-piperazin-1-yl)-[2-(2,3-dihydro-indole-1-carbonyl)-1H-indol-5-yl]-methanone The title compound was synthesized in analogy to example 1, from 5-(4-cyclopentyl-piperazine-1-carbonyl)-1H-indole-2-carboxylic acid 1:1 hydrochloride (example 34, intermediate b), O-(benzotriazol-1-yl)-N,N,N',N'-tetramethyluronium tetrafluoroborate (commercially available), indoline (commercially available) and N,N-diisopropyl-ethylamine in N,N-dimethylformamide, to give the desired product as a light yellow solid (49%).
MS (TIC): 443.1 (M+H$^+$)

Example 41

[5-(4-Cyclobutyl-piperazine-1-carbonyl)-1H-indol-2-yl]-(4,4-difluoro-piperidin-1-yl)-methanone The title compound was synthesized in analogy to example 1, from 5-(4-cyclobutyl-piperazine-1-carbonyl)-1H-indole-2-carboxylic acid hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, to give the desired product as a light brown solid (83%).
MS (TIC): 431.2 (M+H$^+$)

Intermediates 5-(4-Cyclobutyl-piperazine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 1-cyclobutylpiperazine (commercially available) and N,N-diisopropylethylamine in N,N-dimethylformamide, to give the desired product as a light brown solid (62%).
MS (TIC): 356.1 (M+H$^+$)

5-(4-Cyclobutyl-piperazine-1-carbonyl)-1H-indole-2-carboxylic acid; hydrochloride The title compound was synthesized in analogy to example 1, intermediate b), from 5-(4-cyclobutyl-piperazine-1-carbonyl)-1H-indole-2-carboxylic acid ethyl ester, to give the desired product as a brown solid (99%).
MS (TIC): 328.1 (M+H$^+$)

Examples 42 and 43

(4,4-Difluoro-piperidin-1-yl)-[5-((S)-3-dimethylamino-pyrrolidine-1-carbonyl)-1H-indol-2-yl]-methanone and (4,4-Difluoro-piperidin-1-yl)-[5-((R)-3-dimethylamino-pyrrolidine-1-carbonyl)-1H-indol-2-yl]-methanone The title compounds were obtained through separation of the enantiomers of (RS)-(4,4-difluoro-piperidin-1-yl)-[5-(3-dimethylamino-pyrrolidine-1-carbonyl)-1H-indol-2-yl]-methanone (intermediate a) by chiral HPLC chromatography (Chiralpak AD column; Daicel; flow: 35 mL/min; column size: 5×55 cm; mobile phase: ethanol: 2-propanol (1:4 v/v); UV detection at 220 nM). The first-eluting enantiomer was obtained as a light brown foam (29%) and the second enantiomer was obtained as a colorless solid (42%).
MS (TIC): 405.4 (M+H$^+$)—enantiomer 1
MS (TIC): 405.4 (M+H$^+$)—enantiomer 2

Intermediates (RS)-(4,4-Difluoro-piperidin-1-yl)-[5-(3-dimethylamino-pyrrolidine-1-carbonyl)-1H-indol-2-yl]-methanone The title compound was synthesized in analogy to example 1, from (RS)-5-(3-dimethylamino-pyrrolidine-1-carbonyl)-1H-indole-2-carboxylic acid hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, as a colorless solid (77%).
MS (TIC): 405.2 (M+H$^+$)

(RS)-5-(3-Dimethylamino-pyrrolidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 3-(dimethylamino)pyrrolidine (commercially available) and N,N-diisopropylethylamine in N,N-dimethylformamide, to give the desired product as a light brown solid (68%).
MS (TIC): 330.2 (M+H$^+$)

(RS)-5-(3-Dimethylamino-pyrrolidine-1-carbonyl)-
1H-indole-2-carboxylic acid; hydrochloride The title compound was synthesized in analogy to example 1, intermediate b), from (RS)-5-(3-dimethylamino-pyrrolidine-1-carbonyl)-1H-indole-2-carboxylic acid ethyl ester, to give the desired product as a light brown solid (90%).
MS (TS): 302.1 (M+H$^+$)

Example 44

[2-(4,4-Difluoro-piperidine-1-carbonyl)-1H-indol-5-yl]-((S)-2-pyrrolidin-1-ylmethyl-pyrrolidin-1-yl)-methanone The title compound was synthesized in analogy to example 1, from 5-((S)-2-pyrrolidin-1-ylmethyl-pyrrolidine-1-carbonyl)-1H-indole-2-carboxylic acid hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, to give the desired product as a light yellow solid (74%).
MS (TIC): 445.1 (M+H$^+$)

Intermediates 5-((S)-2-Pyrrolidin-1-ylmethyl-pyrrolidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), (S)-(+)-1-(2-pyrrolidinylmethyl)pyrrolidine (commercially available) and N,N-diisopropylethylamine in N,N-dimethylformamide, to give the desired product as a light yellow foam (90%).
MS (TIC): 370.0 (M+H$^+$)

5-((S)-2-Pyrrolidin-1-ylmethyl-pyrrolidine-1-carbonyl)-1H-indole-2-carboxylic acid; hydrochloride The title compound was synthesized in analogy to example 1, intermediate b), from 5-((S)-2-pyrrolidin-1-ylmethyl-pyrrolidine-1-carbonyl)-1H-indole-2-carboxylic acid ethyl ester, to give the desired product as a light brown foam. The so-obtained product was pure enough for the next step without further purification.
MS (TS): 342.0 (M+H$^+$)

Example 45

[2-(4,4-Difluoro-piperidine-1-carbonyl)-1H-indol-5-yl]-((R)-2-pyrrolidin-1-ylmethyl-pyrrolidin-1-yl)-methanone The title compound was synthesized in analogy to example 1, from 5-((R)-2-pyrrolidin-1-ylmethyl-pyrrolidine-1-carbonyl)-1H-indole-2-carboxylic acid hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, to give the desired product as a colorless solid (74%).
MS (TIC): 445.1 (M+H$^+$)

Intermediates 5-((R)-2-Pyrrolidin-1-ylmethyl-pyrrolidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), (R)-(+)-1-(2-pyrrolidinylmethyl)pyrrolidine (commercially available) and N,N-diisopropylethylamine in N,N-dimethylformamide, to give the desired product as a light brown foam (69%).
MS (TIC): 370.1 (M+H$^+$)

5-((R)-2-Pyrrolidin-1-ylmethyl-pyrrolidine-1-carbonyl)-1H-indole-2-carboxylic acid; hydrochloride The title compound was synthesized in analogy to example 1, intermediate b), from 5-((R)-2-pyrrolidin-1-ylmethyl-pyrrolidine-1-carbonyl)-1H-indole-2-carboxylic acid ethyl ester, to give the desired product as a light brown solid (93%). The so-obtained product was pure enough for the next step without further purification.
MS (ISP): 342.0 (M+H$^+$)

Example 46

[5-(4-Isopropyl-piperazine-1-carbonyl)-1-(2,2,2-trifluoro-ethyl)-1H-indol-2-yl]-morpholin-4-yl-methanone (5-Bromo-1H-indol-2-yl)-morpholin-4-yl-methanone A mixture of 5-bromoindole-2-carboxylic acid (5 g, 21 mmol), and 1,1'-carbonyldiimidazole (4.39 g, 27 mmol) in tetrahydrofuran (60 mL) was stirred at room temperature overnight. Morpholine (3.63 mL, 42 mmol) was added and the mixture was stirred for an additional 40 min. The reaction mixture was partitioned between ethyl acetate and an aqueous solution of sodium bicarbonate. The organic layer was washed with hydrochloric acid (1N) and brine, then dried over sodium sulfate, filtered and evaporated in vacuo, to give 6.74 g (99%) of the desired compound as a yellow solid which was used without further purification.
MS (TIC): 310.0 (M+H$^+$)

[5-Bromo-1-(2,2,2-trifluoro-ethyl)-1H-indol-2-yl]-morpholin-4-yl-methanone

To a mixture of (5-bromo-1H-indol-2-yl)-morpholin-4-yl-methanone (6.64 g, 20 mmol) in tetrahydrofuran (60 mL) was added sodium hydride (60% dispersion in oil, 979 mg, 24 mmol) in several portions. The mixture was stirred 15 min at room temperature then 2,2,2-trifluoroethyl trifluoromethanesulfonate (6.16 g, 27 mmol) was added and the reaction mixture was refluxed overnight. The reaction mixture was partitioned between ethyl acetate and an aqueous solution of sodium bicarbonate. The organic layer was washed with hydrochloric acid (1N) and brine, dried over sodium sulfate, filtered and evaporated in vacuo. The crude product was purified by flash chromatography on silica gel with dichloromethane:ethyl acetate (98:2 to 94:6 v/v) as eluant, to give 4.65 g (58%) of the desired compound as an off-white solid.
MS (TIC): 392.0 (M+H$^+$)

2-(Morpholine-4-carbonyl)-1-(2,2,2-trifluoro-ethyl)-1H-indole-5-carboxylic acid ethyl ester A mixture of [5-bromo-1-(2,2,2-trifluoro-ethyl)-1H-indol-2-yl]-morpholin-4-yl-methanone (1.49 g, 4 mmol), palladium acetate (171 mg, 0.76 mmol), 1,3-bis (diphenylphosphino)propane (346 mg, 0.84 mmol), triethylamine (0.58 mL, 4 mmol), ethanol (3 mL) and dimethylsulfoxide (3 mL) was flushed with carbon monoxide. The reaction mixture was stirred vigorously at 75° C. (oil bath), under carbon monoxide (1 Atm) for 19 h. The red mixture was diluted with ethyl acetate, filtered and partitioned between ethyl acetate and brine. The organic layer was washed with brine and dried in vacuo. The crude product was purified by flash chromatography on silica gel with dichloromethane:ethyl acetate (98:2 v/v) as eluant, to give 924 mg (63%) of the desired compound as an off-white solid.

MS (TIC): 385.5 (M+H$^+$)

2-(Morpholine-4-carbonyl)-1-(2,2,2-trifluoro-ethyl)-1H-indole-5-carboxylic acid A solution of 2-(morpholine-4-carbonyl)-1-(2,2,2-trifluoro-ethyl)-1H-indole-5-carboxylic acid ethyl ester (924 mg, 2.4 mmol) and lithium hydroxide monohydrate (200 mg, 4.8 mmol) in tetrahydrofuran (8 mL), methanol (2 mL) and water (4 mL) was refluxed for 3 h. The volatiles were removed in vacuo and the residue was dissolved in water and acidified with hydrochloric acid (1N). The precipitate was filtered, washed with water and dried in vacuo. The crude product was purified by flash chromatography on silica gel with dichloromethane: methanol (98:2 then 19:1 v/v) as eluant, to give 727 mg (85%) of the desired compound as an off-white solid.

MS (TIC): 355.5 (M–H$^+$)

[5-(4-Isopropyl-piperazine-1-carbonyl)-1-(2,2,2-trifluoro-ethyl)-1H-indol-2-yl]-morpholin-4-yl-methanone A mixture of 2-(morpholine-4-carbonyl)-1-(2,2,2-trifluoro-ethyl)-1H-indole-5-carboxylic acid (100 mg, 0.28 mmol) and 1,1'-carbonyl-diimidazole (59 mg, 0.37 mmol) in tetrahydrofuran was stirred at room temperature overnight. 1-Isopropylpiperazine (72 mg, 0.56 mmol) was then added and the mixture was stirred for an additional 40 min. The volatiles were removed in vacuo and the residue was purified by flash chromatography on silica gel with dichloromethane: methanol:ammonia (95:5:0.25 v/v) as eluant, to give 90 mg (68%) of the desired compound as an off-white solid.

MS (TIC): 467.5 (M+H$^+$)

Example 47

[5-(Hexahydro-pyrrolo[1,2-a]pyrazine-2-carbonyl)-1-(2,2,2-trifluoro-ethyl)-1H-indol-2-yl]-morpholin-4-yl-methanone The title compound was synthesized in analogy to example 46, intermediate e), from 2-(morpholine-4-carbonyl)-1-(2,2,2-trifluoro-ethyl)-1H-indole-5-carboxylic acid and 1,4-diazabicyclo[4.3.0]nonane (purchased at Matrix Ref 8078), to give the desired product as a white solid (65%).

MS (ISP): 465.5 (M+H$^+$)

Example 48

(4-Cyclobutyl-piperazin-1-yl)-[2-(morpholine-4-carbonyl)-1-(2,2,2-trifluoro-ethyl)-1H-indol-5-yl]-methanone The title compound was synthesized in analogy to example 46, intermediate e), from 2-(morpholine-4-carbonyl)-1-(2,2,2-trifluoro-ethyl)-1H-indole-5-carboxylic acid and 1-cyclobutylpiperazine (commercially available), to give the desired product as a white solid (50%).

MS (ISP): 479.5 (M+H$^+$)

Example 49

[5-(4-Cyclopentyl-piperazine-1-carbonyl)-1-(2,2,2-trifluoro-ethyl)-1H-indol-2-yl]-morpholin-4-yl-methanone The title compound was synthesized in analogy to example 46, intermediate e), from 2-(morpholine-4-carbonyl)-1-(2,2,2-trifluoro-ethyl)-1H-indole-5-carboxylic acid and 1-cyclopentylpiperazine (commercially available), to give the desired product as a white solid (49%).

MS (ISP): 493.5 (M+H$^+$)

Example 50

[5-(4-Cyclohexyl-piperazine-1-carbonyl)-1-(2,2,2-trifluoro-ethyl)-1H-indol-2-yl]-morpholin-4-yl-methanone The title compound was synthesized in analogy to example 46, intermediate e), from 2-(morpholine-4-carbonyl)-1-(2,2,2-trifluoro-ethyl)-1H-indole-5-carboxylic acid and 1-cyclohexylpiperazine (commercially available), to give the desired product as a white solid (65%).

MS (ISP): 507.5 (M+H$^+$)

Example 51

[1-Cyclopropylmethyl-5-(4-isopropyl-piperazine-1-carbonyl)-1H-indol-2-yl]-(4,4-difluoro-piperidin-1-yl)-methanone The suspension of 0.15 g (0.36 mmol) (4,4-difluoro-piperidin-1-yl)-[5-(4-isopropyl-piperazine-1-carbonyl)-1H-indol-2-yl]-methanone (example 32) and 17 mg (0.36 mmol; 55% dispersion in mineral oil) sodium hydride in 2 mL N,N-dimethylformamide was stirred for 30 min. at 70° C. Then, 42 μL (58 mg, 0.43 mmol) cyclopropylmethyl bromide were added and the solution was stirred another 45 min. at 70° C. After cooling to room temperature the reaction was poured on 10% aqueous ammonium chloride solution and the phases were separated. The aqueous phase was extracted three times with ethyl acetate. The combined organic layers were washed twice with water, followed by brine, dried over magnesium sulfate, filtered and evaporated. The crude product was purified by flash chromatography on silica gel with dichloromethane:methanol:ammonia (9:1:0.1 v/v) as eluant to give 0.16 g (97%) of the desired compound as a colorless foam.

MS (TIC): 437.1 (M+H$^+$)

Example 52

(4,4-Difluoro-piperidin-1-yl)-[5-(4-isopropyl-piperazine-1-carbonyl)-1-(2,2,2-trifluoro-ethyl)-1H-indol-2-yl]-methanone The title compound was synthesized in analogy to example 51, from (4,4-difluoro-piperidin-1-yl)-[5-(4-isopropyl-piperazine-1-carbonyl)-1H-indol-2-yl]-methanone (example 32), sodium hydride and 2,2,2-trifluoroethyl methanesulfonate in N,N-dimethylformamide, to give the desired product as a colorless oil (50%).
MS (TIC): 501.1 (M+H$^+$)

Example 53

(4,4-Difluoro-piperidin-1-yl)-[1-isopropyl-5-(4-isopropyl-piperazine-1-carbonyl)-1H-indol-2-yl]-methanone The title compound was synthesized in analogy to example 51, from (4,4-difluoro-piperidin-1-yl)-[5-(4-isopropyl-piperazine-1-carbonyl)-1H-indol-2-yl]-methanone (example 32), sodium hydride and 2-bromopropane in N,N-dimethylformamide, to give the desired product as a colorless oil (54%).
MS (TIC): 461.2 (M+H$^+$)

Example 54

[2-(4,4-Difluoro-piperidine-1-carbonyl)-5-(4-isopropyl-piperazine-1-carbonyl)-indol-1-yl]-acetonitrile The title compound was synthesized in analogy to example 51, from (4,4-difluoro-piperidin-1-yl)-[5-(4-isopropyl-piperazine-1-carbonyl)-1H-indol-2-yl]-methanone (example 32), sodium hydride and bromoacetonitrile in N,N-dimethylformamide, to give the desired product as a yellow oil (54%).
MS (TIC): 458.2 (M+H$^+$)

Example 55

[5-(4-Cyclopentyl-piperazine-1-carbonyl)-1-cyclopropylmethyl-1H-indol-2-yl]-(4,4-difluoro-piperidin-1-yl)-methanone The title compound was synthesized in analogy to example 51, from [5-(4-cyclopentyl-piperazine-1-carbonyl)-1H-indol-2-yl]-(4,4-difluoro-piperidin-1-yl)-methanone (example 8), sodium hydride and cyclopropylmethyl bromide in N,N-dimethylformamide give the desired product as a colorless foam (44%).
MS (TIC): 500.2 (M+H$^+$)

Example 56

[5-(4-Cyclopentyl-piperazine-1-carbonyl)-1-(2,2,2-trifluoro-ethyl)-1H-indol-2-yl]-(4,4-difluoro-piperidin-1-yl)-methanone The title compound was synthesized in analogy to example 51, from [5-(4-cyclopentyl-piperazine-1-carbonyl)-1H-indol-2-yl]-(4,4-difluoro-piperidin-1-yl)-methanone (example 8), sodium hydride and 2,2,2-trifluoroethyl methanesulfonate in N,N-dimethylformamide, to give the desired product as a colorless foam (31%).
MS (TIC): 527.1 (M+H$^+$)

Example 57

[5-(4-Cyclopentyl-piperazine-1-carbonyl)-1-cyclopropylmethyl-1H-indol-2-yl]-morpholin-4-yl-methanone The title compound was synthesized in analogy to example 51, from (4-cyclopentyl-piperazin-1-yl)-[2-(morpholine-4-carbonyl)-1H-indol-5-yl]-methanone (example 10), sodium hydride and cyclopropylmethyl bromide in N,N-dimethylformamide, to give the desired product as a colorless foam (38%).
MS (TIC): 465.2 (M+H$^+$)

Example 58

[5-(4-Cyclopentyl-piperazine-1-carbonyl)-1-isopropyl-1H-indol-2-yl]-morpholin-4-yl-methanone The title compound was synthesized in analogy to example 51, from (4-cyclopentyl-piperazin-1-yl)-[2-(morpholine-4-carbonyl)-1H-indol-5-yl]-methanone (example 10), sodium hydride and 2-bromopropane in N,N-dimethylformamide, to give the desired product as a colorless foam (31%).
MS (TIC): 453.3 (M+H$^+$)

Example 59

[5-(4-Cyclopentyl-piperazine-1-carbonyl)-1-isopropyl-1H-indol-2-yl]-(4,4-difluoro-piperidin-1-yl)-methanone The title compound was synthesized in analogy to example 51, from [5-(4-cyclopentyl-piperazine-1-carbonyl)-1H-indol-2-yl]-(4,4-difluoro-piperidin-1-yl)-methanone (example 8), sodium hydride and 2-bromopropane in N,N-dimethylformamide give the desired product as a colorless foam (27%).
MS (TIC): 487.2 (M+H$^+$)

Example 60

(4,4-Difluoro-piperidin-1-yl)-[5-(4-isopropyl-piperazine-1-carbonyl)-1-methanesulfonyl-1-indol-2-yl]-methanone The title compound was synthesized in analogy to example 51, from (4,4-difluoro-piperidin-1-yl)-[5-(4-isopropyl-piperazine-1-carbonyl)-1H-indol-2-yl]-methanone (example 32), sodium hydride and methanesulfonyl chloride in N,N-dimethylformamide, to give the desired product as a colorless foam (34%).
MS (TIC): 497.0 (M+H$^+$)

Example 61

[5-(4-Cyclopentyl-piperazine-1-carbonyl)-2-(4,4-difluoro-piperidine-1-carbonyl)-indol-1-yl]-acetonitrile The title compound was synthesized in analogy to example 51, from [5-(4-cyclopentyl-piperazine-1-carbonyl)-1H-indol-2-yl]-(4,4-difluoro-piperidin-1-yl)-methanone (example 8), sodium hydride and bromoacetonitrile in N,N-dimethylformamide, to give the desired product as a light brown foam (42%).
MS (TIC): 484.3 (M+H$^+$)

Example 62

[5-(4-Cyclopentyl-piperazine-1-carbonyl)-1-methanesulfonyl-1H-indol-2-yl]-(4,4-difluoro-piperidin-1-yl)-methanone The title compound was synthesized in analogy to example 51, from [5-(4-cyclopentyl-piperazine-1-carbonyl)-1H-indol-2-yl]-(4,4-difluoro-piperidin-1-yl)-methanone (example 8), sodium hydride and methanesulfonyl chloride in N,N-dimethylformamide, to give the desired product as a colorless foam (35%).
MS (TIC): 523.1 (M+H$^+$)

Example 63

(4-Cyclopentyl-piperazin-1-yl)-[1-methanesulfonyl-2-(morpholine-4-carbonyl)-1H-indol-5-yl]-methanone The title compound was synthesized in analogy to example 51, from (4-cyclopentyl-piperazin-1-yl)-[2-(morpholine-4-carbonyl)-1H-indol-5-yl]-methanone (example 10), sodium hydride and bromoacetonitrile in N,N-dimethylformamide, to give the desired product as a colorless foam (55%).
MS (TIC): 450.2 (M+H$^+$)

Example 64

(4-Cyclopentyl-piperazin-1-yl)-[1-methanesulfonyl-2-(morpholine-4-carbonyl)-1H-indol-5-yl]-methanone The title compound was synthesized in analogy to example 51, from (4-cyclopentyl-piperazin-1-yl)-[2-(morpholine-4-carbonyl)-1H-indol-5-yl]-methanone (example 10), sodium hydride and methanesulfonyl chloride in N,N-dimethylformamide, to give the desired product as a colorless foam (54%).
MS (TIC): 489.2 (M+H$^+$)

Example 65

[1-Benzyl-5-(4-isopropyl-piperazine-1-carbonyl)-1H-indol-2-yl]-(4,4-difluoro-piperidin-1-yl)-methanone The suspension of 0.15 g (0.36 mmol) (4,4-difluoro-piperidin-1-yl)-[5-(4-isopropyl-piperazine-1-carbonyl)-1H-indol-2-yl]-methanone (example 32), 72 µL (76 mg, 0.72 mmol) benzylalcohol and 173 mg (0.72 mmol) (triphenylphosphoranylidene)acetonitrile in 2 mL toluene was stirred for 3 hours under reflux. The volatile components were evaporated at a rotary evaporator and the residue was purified using flash chromatography on silica gel with dichloromethane:methanol (19:1 v/v) as eluant to give 0.11 g (63%) of the desired compound as a light brown foam.
MS (TIC): 509.5 (M+H$^+$)

Example 66

(4,4-Difluoro-piperidin-1-yl)-[5-(4-isopropyl-piperazine-1-carbonyl)-1-p-tolyl-1H-indol-2-yl]-methanone The suspension of 0.15 g (0.36 mmol) (4,4-difluoro-piperidin-1-yl)-[5-(4-isopropyl-piperazine-1-carbonyl)-1H-indol-2-yl]-methanone (example 32), 146 mg (1.1 mmol) 4-methylphenylboronic acid, 0.13 g (0.72 mmol) copper(II) acetate and 0.12 mL (0.11 g, 1.43 mmol) pyridine in 5 mL dichloromethane was stirred for 3 days at room temperature. The volatile components were evaporated at a rotary evaporator and the residue was purified using flash chromatography on silica gel with dichloromethane:methanol (19:1 v/v) as eluant to give 89 mg (49%) of the desired compound as a colorless foam.
MS (TIC): 509.4 (M+H$^+$)

Example 67

(4,4-Difluoro-piperidin-1-yl)-[5-(4-isopropyl-piperazine-1-carbonyl)-1-(4-methoxy-phenyl)-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 4-methoxyphenylboronic acid, copper(II) acetate and pyridine in dichloromethane, to give the desired product as a colorless foam (41%).
MS (TIC): 525.3 (M+H$^+$)

Example 68

(4,4-Difluoro-piperidin-1-yl)-[1-(4-fluoro-phenyl)-5-(4-isopropyl-piperazine-1-carbonyl)-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 4-fluorphenylboronic acid, copper(II) acetate and pyridine in dichloromethane, to give the desired product as a colorless foam (88%).
MS (TIC): 513.4 (M+H$^+$)

Example 69

[1-(4-Chloro-phenyl)-5-(4-isopropyl-piperazine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 4-chlorphenylboronic acid, copper(II) acetate and pyridine in dichloromethane, to give the desired product as a colorless foam (69%).
MS (TIC): 529.3 (M+H$^+$)

Example 70

(4,4-Difluoro-piperidin-1-yl)-[5-(4-isopropyl-piperazine-1-carbonyl)-1-(4-trifluoromethyl-phenyl)-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 4-(trifluoromethyl)phenylboronic acid, copper(II) acetate and pyridine in dichloromethane, to give the desired product as a colorless foam (47%).
MS (TIC): 563.4 (M+H$^+$)

Example 71

4-[2-(4,4-Difluoro-piperidine-1-carbonyl)-5-(4-isopropyl-piperazine-1-carbonyl)-indol-1-yl]-benzonitrile The title compound was synthesized in analogy to example 66, from (4,4-difluoro-piperidin-1-yl)-[5-(4-isopropyl-piperazine-1-carbonyl)-1H-indol-2-yl]-methanone (example 32), 4-cyanophenylboronic acid, copper(II) acetate and pyridine in dichloromethane, to give the desired product as a colorless foam (52%).

MS (TIC): 520.3 (M+H$^+$)

Example 72

[1-(3-Chloro-phenyl)-5-(4-isopropyl-piperazine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 3-chlorphenylboronic acid, copper(II) acetate and pyridine in dichloromethane, to give the desired product as a colorless foam (37%).

MS (TIC): 529.2 (M+H$^+$)

Example 73

3-[2-(4,4-Difluoro-piperidine-1-carbonyl)-5-(4-isopropyl-piperazine-1-carbonyl)-indol-1-yl]-benzonitrile The title compound was synthesized in analogy to example 66, from (4,4-difluoro-piperidin-1-yl)-[5-(4-isopropyl-piperazine-1-carbonyl)-1H-indol-2-yl]-methanone (example 32), 3-cyanophenylboronic acid, copper(II) acetate and pyridine in dichloromethane, to give the desired product as a colorless foam (77%).

MS (TIC): 520.3 (M+H$^+$)

Example 74

[1-Benzyl-5-(4-isopropyl-piperazine-1-carbonyl)-1H-indol-2-yl]-(1,1-dioxo-thiomorpholin-4-yl)-methanone To the suspension of 105 mg (0.70 mmol) (cyanomethyl)trimethylphosphonium chloride (prepared according to Tetrahedron Lett. 1996, 37 (14), 2459-62) in 1 mL toluene, 1.39 mL (0.70 mmol; 0.5M solution in toluene) potassium bis(trimethylsilyl)amide was added. After 10 min., 71 µL (74 mg, 0.70 mmol) benzylalcohol and 0.15 g (0.35 mmol) [2-(1,1-dioxo-thiomorpholine-4-carbonyl)-1H-indol-5-yl]-(4-isopropyl-piperazin-1-yl)-methanone (example 1) were added and the suspension was stirred for 1 h at reflux temperature. After cooling to room temperature the reaction mixture was evaporated to dryness, the residue was taken up in dichloromethane, filtered and the filtrate was evaporated. The crude product was purified by flash column chromatography on silica gel with dichloromethane:methanol:ammonia (19:1:0.1 v/v) as eluant to give 118 mg (65%) of the desired compound as a colorless foam.

MS (TIC): 523.2 (M+H$^+$)

Example 75

[1-(4-Chloro-phenyl)-5-(4-cyclopentyl-piperazine-1-carbonyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-chlorphenylboronic acid, copper(II) acetate and pyridine in dichloromethane, to give the desired product as a white solid (23%).

MS (TIC): 555.3 (M+H$^+$)

Example 76

[1-(3-Chloro-phenyl)-5-(4-cyclopentyl-piperazine-1-carbonyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-chlorphenylboronic acid, copper(II) acetate and pyridine in dichloromethane, to give the desired product as a white solid (76%).

MS (TIC): 555.2 (M+H$^+$)

Example 77

[5-(4-Cyclopentyl-piperazine-1-carbonyl)-1-(4-fluoro-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-fluorphenylboronic acid, copper(II) acetate and pyridine in dichloromethane, to give the desired product as a light yellow foam (82%).

MS (TIC): 539.4 (M+H$^+$)

Example 78

[5-(4-Cyclopentyl-piperazine-1-carbonyl)-1-(3-fluoro-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-fluorphenylboronic acid, copper(II) acetate and pyridine in dichloromethane, to give the desired product as a white foam (78%).

MS (TIC): 539.4 (M+H$^+$)

Example 79

[5-(4-Cyclopentyl-piperazine-1-carbonyl)-1-(4-trifluoromethyl-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-(trifluoromethyl)phenylboronic acid, copper(II) acetate and pyridine in dichloromethane, to give the desired product as a white foam (51%).

MS (TIC): 589.4 (M+H$^+$)

Example 80

[5-(4-Cyclopentyl-piperazine-1-carbonyl)-1-(3-trifluoromethyl-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-(trifluoromethyl)phenylboronic acid, copper(II) acetate and pyridine in dichloromethane, to give the desired product as a white foam (73%).

MS (TIC): 589.5 (M+H$^+$)

Example 81

[5-(4-Cyclopentyl-piperazine-1-carbonyl)-1-p-tolyl-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-methylphenylboronic acid, copper(II) acetate and pyridine in dichloromethane, to give the desired product as a white foam (89%).

MS (TIC): 535.4 (M+H$^+$)

Example 82

[5-(4-Cyclopentyl-piperazine-1-carbonyl)-1-m-tolyl-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-methylphenylboronic acid, copper(II) acetate and pyridine in dichloromethane, to give the desired product as a white foam (81%).

MS (TIC): 535.4 (M+H$^+$)

Example 83

[5-(4-Cyclopentyl-piperazine-1-carbonyl)-1-(4-methoxy-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-methoxyphenylboronic acid, copper(II) acetate and pyridine in dichloromethane, to give the desired product as a white foam (73%).

MS (TIC): 551.2 (M+H$^+$)

Example 84

[5-(4-Cyclopentyl-piperazine-1-carbonyl)-1-(3-methoxy-phenyl)-1H-indol-2-yl]-(4,4-difluoro-piperidin-1-yl)-methanone The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-methoxyphenylboronic acid, copper(II) acetate and pyridine in dichloromethane, to give the desired product as a white foam (73%).

MS (TIC): 551.2 (M+H$^+$)

Example 85

4-[5-(4-Cyclopentyl-piperazine-1-carbonyl)-2-(4,4-difluoro-piperidine-1-carbonyl)-indol-1-yl]-benzoic acid methyl ester The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-methoxycarbonylphenylboronic acid, copper(II) acetate and pyridine in dichloromethane, to give the desired product as a white foam (67%).

MS (TIC): 579.3 (M+H$^+$)

Example 86

3-[5-(4-Cyclopentyl-piperazine-1-carbonyl)-2-(4,4-difluoro-piperidine-1-carbonyl)-indol-1-yl]-benzoic acid ethyl ester The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-ethoxycarbonylphenylboronic acid, copper(II) acetate and pyridine in dichloromethane, to give the desired product as a white foam (69%).

MS (TIC): 593.4 (M+H$^+$)

Example 87

[5-(4-Cyclopentyl-piperazine-1-carbonyl)-2-(1,1-dioxo-1,l-thiomorpholine-4-carbonyl)-indol-1-yl]-acetonitrile The title compound was synthesized in analogy to example 51, from [5-(4-cyclopentyl-piperazine-1-carbonyl)-1H-indol-2-yl]-(1,1-dioxo-thiomorpholin-4-yl)-methanone (example 34), sodium hydride and bromoacetonitrile in N,N-dimethylformamide, to give the desired product as a light yellow foam (7%).

MS (TIC): 498.2 (M+H$^+$)

Example 88

4-[5-(4-Cyclopentyl-piperazine-1-carbonyl)-2-(4,4-difluoro-piperidine-1-carbonyl)-indol-1-yl]-benzonitrile The title compound was synthesized in analogy to example 66, from [5-(4-cyclopentyl-piperazine-1-carbonyl)-1H-indol-2-yl]-(4,4-difluoro-piperidin-1-yl)-methanone (example 8), 4-cyanophenylboronic acid, copper(II) acetate and pyridine in dichloromethane, to give the desired product as a white foam (19%).

MS (TIC): 546.3 (M+H$^+$)

Example 89

3-[5-(4-Cyclopentyl-piperazine-1-carbonyl)-2-(4,4-difluoro-piperidine-1-carbonyl)-indol-1-yl]-benzonitrile The title compound was synthesized in analogy to example 66, from [5-(4-cyclopentyl-piperazine-1-carbonyl)-1H-indol-2-yl]-(4,4-difluoro-piperidin-1-yl)-methanone (example 8), 3-cyanophenylboronic acid, copper(II) acetate and pyridine in dichloromethane, to give the desired product as a white foam (39%).

MS (TIC): 546.3 (M+H$^+$)

Example 90

(4,4-Difluoro-piperidin-1-yl)-[5-(4-isopropyl-piperazine-1-carbonyl)-1-m-tolyl-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 3-methylphenylboronic acid, copper(II) acetate and pyridine in dichloromethane, to give the desired product as a white foam (45%).

MS (TIC): 509.4 (M+H$^+$)

Example 91

(4,4-Difluoro-piperidin-1-yl)-[5-(4-isopropyl-piperazine-1-carbonyl)-1-(3-trifluoromethyl-phenyl)-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 3-(trifluoromethyl)phenylboronic acid, copper(II) acetate and pyridine in dichloromethane, to give the desired product as a white foam (33%).

MS (TIC): 563.5 (M+H$^+$)

Example 92

3-[2-(4,4-Difluoro-piperidine-1-carbonyl)-5-(4-isopropyl-piperazine-1-carbonyl)-indol-1-yl]-benzoic acid ethyl ester The title compound was synthesized in analogy to example 66, from (4,4-difluoro-piperidin-1-yl)-[5-(4-isopropyl-piperazine-1-carbonyl)-1H-indol-2-yl]-methanone (example 32), 3-ethoxycarbonylphenylboronic acid, copper(II) acetate and pyridine in dichloromethane, to give the desired product as a light yellow foam (29%).

MS (TIC): 567.4 (M+H$^+$)

Example 93

4-[2-(4,4-Difluoro-piperidine-1-carbonyl)-5-(4-isopropyl-piperazine-1-carbonyl)-indol-1-yl]-benzoic acid methyl ester The title compound was synthesized in analogy to example 66, from (4,4-difluoro-piperidin-1-yl)-[5-(4-isopropyl-piperazine-1-carbonyl)-1H-indol-2-yl]-methanone (example 32), 4-methoxycarbonylphenylboronic acid, copper(II) acetate and pyridine in dichloromethane, to give the desired product as a colorless foam (40%).

MS (TIC): 553.3 (M+H$^+$)

Example 94

(4,4-Difluoro-piperidin-1-yl)-[1-(4-fluoro-benzyl)-5-(4-isopropyl-piperazine-1-carbonyl)-1H-indol-2-yl]-methanone The title compound was synthesized in analogy to example 74, from (cyanomethyl)trimethylphosphonium chloride (prepared according to Tetrahedron Lett. 1996, 37 (14), 2459-62), potassium bis(trimethylsilyl)amide, 4-fluorobenzylalcohol and (4,4-difluoro-piperidin-1-yl)-[5-(4-isopropyl-piperazine-1-carbonyl)-1H-indol-2-yl]-methanone (example 32) in toluene to give the compound as a colorless foam (37%).

MS (TIC): 527.1 (M+H$^+$)

Example 95

(4,4-Difluoro-piperidin-1-yl)-[5-(4-isopropyl-piperazine-1-carbonyl)-1-(1-phenyl-ethyl)-1H-indol-2-yl]-methanone The title compound was synthesized in analogy to example 74, from (cyanomethyl)trimethylphosphonium chloride (prepared according to Tetrahedron Lett. 1996, 37 (14), 2459-62), potassium bis(trimethylsilyl)amide, 1-phenylethanol and (4,4-difluoro-piperidin-1-yl)-[5-(4-isopropyl-piperazine-1-carbonyl)-1H-indol-2-yl]-methanone (example 32) in toluene to give the compound as a light brown foam (37%).

MS (TIC): 523.3 (M+H$^+$)

Example 96

Cyclopropylmethyl-5-(4-isopropyl-piperazine-1-carbonyl)-1H-indole-2-carboxylic acid (3-fluoro-oxetan-3-ylmethyl)-amide The title compound was synthesized in analogy to example 51, from 5-(4-isopropyl-piperazine-1-carbonyl)-1H-indole-2-carboxylic acid (3-fluoro-oxetan-3-ylmethyl)-amide, sodium hydride and cyclopropylmethyl bromide in N,N-dimethylformamide, to give the desired product as a colorless foam (40%).

MS (TIC): 457.3 (M+H$^+$)

Intermediate 5-(4-Isopropyl-piperazine-1-carbonyl)-1H-indole-2-carboxylic acid (3-fluoro-oxetan-3-ylmethyl)-amide The title compound was synthesized in analogy to example 1, from 5-(4-isopropyl-piperazine-1-carbonyl)-1H-indole-2-carboxylic acid 1:1 hydrochloride (example 1, intermediate b), (3-fluoro-oxetan-3-yl)-methylamine (commercially available), O-(benzotriazol-1-yl)-N,N,N',N'-tetramethyluronium tetrafluoroborate (commercially available) and N,N-diisopropylethylamine in N,N-dimethylformamide, to give the desired product as a colorless solid (42%).

MS (TIC): 403.3 (M+H$^+$)

Example 97

[1-(3-Chloro-phenyl)-5-(4-isopropyl-piperazine-1-carbonyl)-1H-indol-2-yl]-(1,1-dioxo-thiomorpholin-4-yl)-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-chlorphenylboronic acid, copper(II) acetate and pyridine in dichloromethane, to give the desired product as a light brown solid (21%).

MS (TIC): 543.2 (M+H$^+$)

Example 98

3-[2-(1,1-Dioxo-thiomorpholine-4-carbonyl)-5-(4-isopropyl-piperazine-1-carbonyl)-indol-1-yl]-benzonitrile The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-cyanophenylboronic acid, copper(II) acetate and pyridine in dichloromethane, to give the desired product as a colorless solid (16%).

MS (TIC): 534.3 (M+H$^+$)

Example 99

(1,1-Dioxo-thiomorpholin-4-yl)-[5-(4-isopropyl-piperazine-1-carbonyl)-1-(3-trifluoromethyl-phenyl)-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-(trifluoromethyl)phenylboronic acid, copper(II) acetate and pyridine in dichloromethane, to give the desired product as a light yellow foam (35%).

MS (TIC): 577.1 (M+H$^+$)

Example 100

[1-(4-Chloro-phenyl)-5-(4-cyclopentyl-piperazine-1-carbonyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 4-chlorophenylboronic acid, copper(II) acetate and pyridine in dichloromethane, to give the desired product as a colorless solid (34%).

MS (TIC): 569.3 (M+H$^+$)

Example 101

[5-(4-Cyclopentyl-piperazine-1-carbonyl)-1-isopropyl-1H-indol-2-yl]-(1,1-dioxo-thiomorpholin-4-yl)-methanone The title compound was synthesized in analogy to example 51, from [5-(4-cyclopentyl-piperazine-1-carbonyl)-1H-indol-2-yl]-(1,1-dioxo-thiomorpholin-4-yl)-methanone (example 34), sodium hydride and 2-bromopropane in N,N-dimethylformamide, to give the desired product as a light yellow foam (33%).

MS (TIC): 501.2 (M+H$^+$)

Example 102

[1-(3-Chloro-phenyl)-5-(4-cyclopentyl-piperazine-1-carbonyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 3-chlorophenylboronic acid, copper(II) acetate and pyridine in dichloromethane, to give the desired product as a light yellow solid (20%).

MS (TIC): 569.3 (M+H$^+$)

Example 103

[5-(4-Cyclopentyl-piperazine-1-carbonyl)-1-(4-fluoro-phenyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 4-fluorophenylboronic acid, copper(II) acetate and pyridine in dichloromethane, to give the desired product as a light yellow solid (34%).

MS (TIC): 553.2 (M+H$^+$)

Example 104

[5-(4-Cyclopentyl-piperazine-1-carbonyl)-1-(3-fluoro-phenyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 3-fluorophenylboronic acid, copper(II) acetate and pyridine in dichloromethane, to give the desired product as a light yellow solid (46%).

MS (TIC): 553.2 (M+H$^+$)

Example 105

[5-(4-Cyclopentyl-piperazine-1-carbonyl)-1-(4-trifluoromethyl-phenyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 4-(trifluoromethyl)phenylboronic acid, copper(II)

Example 106

[5-(4-Cyclopentyl-piperazine-1-carbonyl)-1-(3-trifluoromethyl-phenyl)-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 3-(trifluoromethyl)phenylboronic acid, copper(II) acetate and pyridine in dichloromethane, to give the desired product as a light yellow solid (40%).

MS (TIC): 603.2 (M+H$^+$)

Example 107

[5-(4-Cyclopentyl-piperazine-1-carbonyl)-1-p-tolyl-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 4-methylphenylboronic acid, copper(II) acetate and pyridine in dichloromethane, to give the desired product as a light yellow solid (69%).

MS (TIC): 549.3 (M+H$^+$)

Example 108

[5-(4-Cyclopentyl-piperazine-1-carbonyl)-1-m-tolyl-1H-indol-2-yl]-(1,1-dioxo-thiomorpholin-4-yl)-methanone The title compound was synthesized in analogy to example 66, from [5-(4-cyclopentyl-piperazine-1-carbonyl)-1H-indol-2-yl]-(1,1-dioxo-thiomorpholin-4-yl)-methanone (example 34), 3-methylphenylboronic acid, copper(II) acetate and pyridine in dichloromethane, to give the desired product as a light yellow solid (76%).

MS (TIC): 549.3 (M+H$^+$)

Example 109

[5-(4-Cyclopentyl-piperazine-1-carbonyl)-1-cyclopropylmethyl-1H-indol-2-yl]-(1,1-dioxo-thiomorpholin-4-yl)-methanone The title compound was synthesized in analogy to example 51, from [5-(4-cyclopentyl-piperazine-1-carbonyl)-1H-indol-2-yl]-(1,1-dioxo-thiomorpholin-4-yl)-methanone (example 34), sodium hydride and cyclopropylmethyl bromide in N,N-dimethylformamide, to give the desired product as a light yellow solid (70%).

MS (TIC): 513.3 (M+H$^+$)

Example 110

[5-(4-Cyclopentyl-piperazine-1-carbonyl)-1-(2,2,2-trifluoro-ethyl)-1H-indol-2-yl]-(1,1-dioxo-thiomorpholin-4-yl)-methanone The title compound was synthesized in analogy to example 51, from [5-(4-cyclopentyl-piperazine-1-carbonyl)-1H-indol-2-yl]-(1,1-dioxo-thiomorpholin-4-yl)-methanone (example 34), sodium hydride and 2,2,2-trifluoroethyl methanesulfonate in N,N-dimethylformamide, to give the desired product as a light yellow solid (60%).

MS (TIC): 541.2 (M+H$^+$)

Example 111

[1-(4-Chloro-phenyl)-5-(4-isopropyl-piperazine-1-carbonyl)-1H-indol-2-yl]-(1,1-dioxo-thiomorpholin-4-yl)-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 4-chlorophenylboronic acid, copper(II) acetate and pyridine in dichloromethane, to give the desired product as a colorless solid (34%).

MS (ISP): 543.3 (M+H$^+$)

Example 112

4-[2-(1,1-Dioxo-thiomorpholine-4-carbonyl)-5-(4-isopropyl-piperazine-1-carbonyl)-indol-1-yl]-benzonitrile The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 4-cyanophenylboronic acid, copper(II) acetate and pyridine in dichloromethane, to give the desired product as a light brown solid (11%).

MS (ISP): 534.3 (M+H$^+$)

Example 113

(1,1-Dioxo-thiomorpholin-4-yl)-[5-(4-isopropyl-piperazine-1-carbonyl)-1-(4-trifluoromethyl-phenyl)-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 4-(trifluoromethyl)phenylboronic acid, copper(II) acetate and pyridine in dichloromethane, to give the desired product as a light brown solid (12%).

MS (ISP): 577.2 (M+H$^+$)

Example 114

[1-Cyclopropylmethyl-5-(4-isopropyl-piperazine-1-carbonyl)-1H-indol-2-yl]-(1,1-dioxo-thiomorpholin-4-yl)-methanone The title compound was synthesized in analogy to example 51, from [2-(1,1-dioxo-thiomorpholine-4-carbonyl)-1H-indol-5-yl]-(4-isopropyl-piperazin-1-yl)-methanone (example 1), sodium hydride and cyclopropylmethyl bromide in N,N-dimethylformamide, to give the desired product as a colorless foam (27%).

MS (TIC): 487.2 (M+H$^+$)

Example 115

(1,1-Dioxo-thiomorpholin-4-yl)-[5-(4-isopropyl-piperazine-1-carbonyl)-1-(2,2,2-trifluoro-ethyl)-1H-indol-2-yl]-methanone The title compound was synthesized in analogy to example 51, from [2-(1,1-dioxo-thiomorpholine-4-carbonyl)-1H-indol-5-yl]-(4-isopropyl-piperazin-1-yl)-methanone (example 1), sodium hydride and 2,2,2-trifluoroethyl methanesulfonate in N,N-dimethylformamide, to give the desired product as a colorless foam (74%).

MS (TIC): 515.2 (M+H$^+$)

Example 116

[5-(4-Isopropyl-piperazine-1-carbonyl)-1-(3-trifluoromethyl-phenyl)-1H-indol-2-yl]-morpholin-4-yl-methanone A mixture of 0.15 g (0.039 mmol) [5-(4-Isopropyl-piperazine-1-carbonyl)-1H-indol-2-yl]-morpholin-4-yl-methanone, 0.1 g (0.039 mmol) 3-iodobenzotrifluoride, 0.006 g (0.00052 mmol) trans-1,2-diaminocyclohexane, 0.003 g (0.00016 mmol) copper(I)iodide and 0.174 g (0.081 mmol) potassium phosphate in 1 mL dioxane was heated to reflux for 43 h. After 20 h another 0.006 g (0.00052 mmol) trans-1,2-diaminocyclohexane and 0.003 g (0.00016 mmol) copper(I) iodide was added. After filtration the mixture was evaporated to dryness and the residue was purified on silica eluting with a gradient formed from CH$_2$Cl$_2$, methanol and 2N NH$_3$. The product fractions were evaporated to yield 0.147 g (71%) of the title compound as brown foam.

MS (TIC): 529.1 (M+H$^+$).

Example 117

[5-(4-Isopropyl-piperazine-1-carbonyl)-1-(4-trifluoromethyl-phenyl)-1H-indol-2-yl]-morpholin-4-yl-methanone The title compound was synthesized in analogy to example 116, from [5-(4-isopropyl-piperazine-1-carbonyl)-1H-indol-2-yl]-morpholin-4-yl-methanone and 4-iodobenzotrifluoride.

MS (TIC): 529.1 (M+H$^+$).

Example 118

4-[5-(4-Isopropyl-piperazine-1-carbonyl)-2-(morpholine-4-carbonyl)-indol-1-yl]-benzonitrile The title compound was synthesized in analogy to example 116, from [5-(4-isopropyl-piperazine-1-carbonyl)-1H-indol-2-yl]-morpholin-4-yl-methanone and 4-iodobenzonitrile.

MS (TIC): 486.3 (M+H$^+$).

Example 119

(4,4-Difluoro-piperidin-1-yl)-[1-(3-fluoro-phenyl)-5-(4-isopropyl-piperazine-1-carbonyl)-1H-indol-2-yl]-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 3-fluorophenylboronic acid, copper(II) acetate and pyridine in dichloromethane, to give the desired product as a yellow oil (35%).

MS (TIC): 513.3 (M+H$^+$)

Example 120

(1,1-Dioxo-1,l,6-thiomorpholin-4-yl)-[5-(4-isopropyl-piperazine-1-carbonyl)-1-(1-phenyl-ethyl)-1H-indol-2-yl]-methanone The title compound was synthesized in analogy to example 74, from (cyanomethyl)trimethylphosphonium chloride (prepared according to Tetrahedron Lett. 1996, 37 (14), 2459-62), potassium bis(trimethylsilyl)amide, 1-phenylethanol in toluene, to give the desired product as a light brown solid (23%).

MS (TIC): 537.3 (M+H$^+$)

Example 121

(4,4-Difluoro-piperidin-1-yl)-[1-[1-(2-fluoro-phenyl)-ethyl]-5-(4-isopropyl-piperazine-1-carbonyl)-1H-indol-2-yl]-methanone The title compound was synthesized in analogy to example 74, from (cyanomethyl)-trimethylphosphonium chloride (prepared according to Tetrahedron Lett. 1996, 37 (14), 2459-62), potassium bis(trimethylsilyl)amide, 1-(2-fluorophenyl) ethanol and (4,4-difluoro-piperidin-1-yl)-[5-(4-isopropyl-piperazine-1-carbonyl)-1H-indol-2-yl]-methanone (example 32) in toluene, to give the desired product as a light brown foam (15%).

MS (TIC): 541.2 (M+H$^+$)

Example 122

[1-Cyclobutylmethyl-5-(4-isopropyl-piperazine-1-carbonyl)-1H-indol-2-yl]-(4,4-difluoro-piperidin-1-yl)-methanone The title compound was synthesized in analogy to example 51, from (4,4-difluoro-piperidin-1-yl)-[5-(4-isopropyl-piperazine-1-carbonyl)-1H-indol-2-yl]-methanone (example 32), sodium hydride and (bromomethyl)cyclobutane in N,N-dimethylformamide, to give the desired product as a colorless foam (69%).

MS (TIC): 487.2 (M+H$^+$)

Examples 123 and 124

(4,4-Difluoro-piperidin-1-yl)-[5-(4-isopropyl-piperazine-1-carbonyl)-1-((R)-1-phenyl-ethyl)-1H-indol-2-yl]-methanone and (4,4-Difluoro-piperidin-1-yl)-[5-(4-isopropyl-piperazine-1-carbonyl)-1-((S)-1-phenyl-ethyl)-1H-indol-2-yl]-methanone The title compounds were obtained through separation of the enantiomers of (RS)-(4,4-difluoro-piperidin-1-yl)-[5-(4- isopropyl-piperazine-1-carbonyl)-1-(1-phenyl-ethyl)-1H-indol-2-yl]-methanone by chiral HPLC chromatography (Chiralpak AD column; Daicel; flow: 35 mL/min; column size: 5×55 cm; mobile phase: n-heptane: 2-propanol (30:70 v/v); UV detection at 220 nM). The first-eluting enantiomer was obtained as a light brown foam (31%) and the second enantiomer was obtained as a light brown foam (37%).

MS (TIC): 405.4 (M+H$^+$)—enantiomer 1 MS (TIC): 405.4 (M+H$^+$)—enantiomer 2

Example 123 was independently synthesized according to example 74 under inversion of the configuration (e.e. >94%), from (cyanomethyl)trimethylphosphonium chloride (prepared according to Tetrahedron Lett. 1996, 37 (14), 2459-62), potassium bis(trimethylsilyl)amide, (S)-1-phenylethanol and (4,4-difluoro-piperidin-1-yl)-[5-(4-isopropyl-piperazine-1-carbonyl)-1H-indol-2-yl]-methanone (example 32) in toluene, to give the compound as a light brown foam (32%).

MS (TIC): 523.2 (M+H$^+$)

Intermediate (RS)-(4,4-Difluoro-piperidin-1-yl)-[5-(4-isopropyl-piperazine-1-carbonyl)-1-(1-phenyl-ethyl)-1H-indol-2-yl]-methanone The title compound was synthesized in analogy to example 74, from (cyanomethyl)trimethylphosphonium chloride (prepared according to Tetrahedron Lett. 1996, 37 (14), 2459-62), potassium bis(trimethylsilyl)amide, 1-phenylethanol and (4,4-difluoro-piperidin-1-yl)-[5-(4-isopropyl-piperazine-1-carbonyl)-1H-indol-2-yl]-methanone (example 32) in toluene, to give the compound as a light brown foam (37%).

MS (TIC): 523.2 (M+H$^+$)

Example 125

[1-(3-Chloro-phenyl)-5-(4-cyclobutyl-piperazine-1-carbonyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3-chlorophenylboronic acid, copper(II) acetate and pyridine in dichloromethane, to give the desired product as a colorless solid (10%).

MS (ISP): 541.3 (M+H$^+$)

Example 126

3-[5-(4-Cyclobutyl-piperazine-1-carbonyl)-2-(4,4-difluoro-piperidine-1-carbonyl)-indol-1-yl]-benzonitrile The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3-cyanophenylboronic acid, copper(II) acetate and pyridine in dichloromethane, to give the desired product as a colorless foam (20%).

MS (ISP): 532.2 (M+H$^+$)

Example 127

[5-(4-Cyclobutyl-piperazine-1-carbonyl)-1-(3-trifluoromethyl-phenyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3-(trifluoromethyl)phenylboronic acid, copper(II) acetate and pyridine in dichloromethane, to give the desired product as a light brown foam (60%).

MS (TIC): 575.3 (M+H$^+$)

Example 128

[1-(4-Chloro-phenyl)-5-(4-cyclobutyl-piperazine-1-carbonyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 4-chlorophenylboronic acid, copper(II) acetate and pyridine in dichloromethane, to give the desired product as a colorless foam (56%).

MS (TIC): 541.2 (M+H$^+$)

Example 129

4-[5-(4-Cyclobutyl-piperazine-1-carbonyl)-2-(4,4-difluoro-piperidine-1-carbonyl)-indol-1-yl]-benzonitrile The title compound was synthesized in analogy to example 66, from [5-(4-cyclobutyl-piperazine-1-carbonyl)-1H-indol-2-yl]-(4,4-difluoro-piperidin-1-yl)-methanone (example 41), 4-cyanophenylboronic acid, copper(II) acetate and pyridine in dichloromethane, to give the desired product as a off-white foam (30%).

MS (ISP): 532.2 (M+H$^+$)

Example 130

[5-(4-Cyclobutyl-piperazine-1-carbonyl)-1-(4-trifluoromethyl-phenyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3-(trifluoromethyl)phenylboronic acid, copper(II) acetate and pyridine in dichloromethane, to give the desired product as a colorless foam (49%).

MS (TIC): 575.3 (M+H$^+$)

Example 131

[5-(4-Cyclobutyl-piperazine-1-carbonyl)-1-cyclopropylmethyl-1H-indol-2-yl]-(4,4-difluoro-piperidin-1-yl)-methanone The title compound was synthesized in analogy to example 51, from [5-(4-cyclobutyl-piperazine-1-carbonyl)-1H-indol-2-yl]-(4,4-difluoro-piperidin-1-yl)-methanone (example 41), sodium hydride and cyclopropylmethyl bromide in N,N-dimethylformamide, to give the desired product as a colorless foam (73%).

MS (TIC): 485.3 (M+H$^+$)

Example 132

[5-(4-Cyclobutyl-piperazine-1-carbonyl)-1-(2,2,2-trifluoro-ethyl)-1H-indol-2-yl]-(4,4-difluoro-piperidin-1-yl)-methanone The title compound was synthesized in analogy to example 51, from [5-(4-cyclobutyl-piperazine-1-carbonyl)-1H-indol-2-yl]-(4,4-difluoro-piperidin-1-yl)-methanone (example 41), sodium hydride and 2,2,2-trifluoroethyl methanesulfonate in N,N-dimethylformamide, to give the desired product as a colorless foam (50%).

MS (TIC): 513.2 (M+H$^+$)

Example 133

[5-(4-Cyclobutyl-piperazine-1-carbonyl)-1-isopropyl-1H-indol-2-yl]-(4,4-difluoro-piperidin-1-yl)-methanone The title compound was synthesized in analogy to example 51, from [5-(4-cyclobutyl-piperazine-1-carbonyl)-1H-indol-2-yl]-(4,4-difluoro-piperidin-1-yl)-methanone (example 41), sodium hydride and 2-bromopropane in N,N-dimethylformamide, to give the desired product as a colorless foam (34%).

MS (TIC): 473.1 (M+H$^+$)

Example 134

[1-Cyclopropylmethyl-5-(3-dimethylamino-pyrrolidine-1-carbonyl)-1H-indol-2-yl]-(4,4-difluoro-piperidin-1-yl)-methanone The title compound was synthesized in analogy to example 51, from (RS)-(4,4-difluoro-piperidin-1-yl)-[5-(3-dimethylamino-pyrrolidine-1-carbonyl)-1H-indol-2-yl]-methanone (example 42, intermediate a)), sodium hydride and cyclopropylmethyl bromide in N,N-dimethylformamide, to give the desired product as a colorless foam (53%).

MS (TIC): 459.3 (M+H$^+$)

Example 135

(RS)-(4,4-Difluoro-piperidin-1-yl)-[5-(3-dimethylamino-pyrrolidine-1-carbonyl)-1-(2,2,2-trifluoro-ethyl)-1H-indol-2-yl]-methanone The title compound was synthesized in analogy to example 51, from (RS)-(4,4-difluoro-piperidin-1-yl)-[5-(3-dimethylamino-pyrrolidine-1-carbonyl)-1H-indol-2-yl]-methanone (example 42, intermediate a)), sodium hydride and 2,2,2-trifluoroethyl methanesulfonate in N,N-dimethylformamide, to give the desired product as a colorless foam (73%).

MS (TIC): 487.1 (M+H$^+$)

Example 136

(RS)-(4,4-Difluoro-piperidin-1-yl)-[5-(3-dimethylamino-pyrrolidine-1-carbonyl)-1-isopropyl-1H-indol-2-yl]-methanone The title compound was synthesized in analogy to example 51, from (RS)-(4,4-difluoro-piperidin-1-yl)-[5-(3-dimethylamino-pyrrolidine-1-carbonyl)-1H-indol-2-yl]-methanone (example 42, intermediate a)), sodium hydride and 2-bromopropane in N,N-dimethylformamide, to give the desired product as a colorless foam (35%).

MS (TIC): 447.1 (M+H$^+$)

Example 137

(RS)-[1-(3-Chloro-phenyl)-5-(3-dimethylamino-pyrrolidine-1-carbonyl)-1H-indol-2-yl]-(4,4-difluoro-piperidin-1-yl)-methanone The title compound was synthesized in analogy to example 66, from (RS)-(4,4-difluoro-piperidin-1-yl)-[5-(3-dimethylamino-pyrrolidine-1-carbonyl)-1H-indol-2-yl]-methanone (example 42, intermediate a)), 3-chlorophenylboronic acid, copper(II) acetate and pyridine in dichloromethane, to give the desired product as a colorless foam (30%).

MS (ISP): 515.4 (M+H$^+$)

Example 138

(RS)-3-[2-(4,4-Difluoro-piperidine-1-carbonyl)-5-(3-dimethylamino-pyrrolidine-1-carbonyl)-indol-1-yl]-benzonitrile The title compound was synthesized in analogy to example 66, from (RS)-(4,4-difluoro-piperidin-1-yl)-[5-(3-dimethylamino-pyrrolidine-1-carbonyl)-1H-indol-2-yl]-methanone (example 42, intermediate a)), 3-cyanophenylboronic acid, copper(II) acetate and pyridine in dichloromethane, to give the desired product as a colorless foam (40%).

MS (ISP): 506.3 (M+H$^+$)

Example 139

(RS)-(4,4-Difluoro-piperidin-1-yl)-[5-(3-dimethylamino-pyrrolidine-1-carbonyl)-1-(3-trifluoromethyl-phenyl)-1H-indol-2-yl]-methanone The title compound was synthesized in analogy to example 66, from (RS)-(4,4-difluoro-piperidin-1-yl)-[5-(3-dimethylamino-pyrrolidine-1-carbonyl)-1H-indol-2-yl]-methanone (example 42, intermediate a)), 3-(trifluoromethyl)phenylboronic acid, copper(II) acetate and pyridine in dichloromethane, to give the desired product as a light brown foam (60%).

MS (ISP): 549.5 (M+H$^+$)

Example 140

[1-(3-Chloro-phenyl)-5-(4-dimethylamino-piperidine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-dimethylamino-piperidine-1-carbonyl)-1H-indol-2-yl]-methanone, 3-chlorophenylboronic acid, copper(II) acetate and pyridine in dichloromethane, to give the desired product as an off-white foam (28%).

MS (ISP): 529.3 (M+H$^+$)

Intermediates (4,4-Difluoro-piperidin-1-yl)-[5-(4-dimethylamino-piperidine-1-carbonyl)-1H-indol-2-yl]-methanone The title compound was synthesized in analogy to example 1, from 5-(4-dimethylamino-piperidine-1-carbonyl)-1H-indole-2-carboxylic acid hydrochloride, O-(benzotriazol-1-yl)-N,N,N',N'-tetramethyluronium tetrafluoroborate (commercially available), 4-fluoroaniline (commercially available) and N,N-diisopropylethylamine in N,N-dimethylformamide, to give the desired product as a light yellow foam (72%).

MS (TIC): 419.2 (M+H$^+$)

5-(4-Dimethylamino-piperidine-1-carbonyl)-1H-indole-2-carboxylic acid; 1:1 hydrochloride The title compound was synthesized in analogy to example 1, intermediate b), from 5-(4-dimethylamino-piperidine-1-carbonyl)-1H-indole-2-carboxylic acid ethyl ester, to give the desired product as a light brown solid. The so-obtained product was pure enough without further purification for the next step.

MS (TIC): 316.0 (M+H$^+$)

5-(4-Dimethylamino-piperidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 4-dimethylamino-piperidine dihydrochloride (commercially available) and N,N-diisopropylethylamine in N,N-dimethylformamide, to give the desired product as a light yellow foam (67%).

MS (TIC): 344.1 (M+H$^+$)

Example 141

3-[2-(4,4-Difluoro-piperidine-1-carbonyl)-5-(4-dimethylamino-piperidine-1-carbonyl)-indol-1-yl]-benzonitrile The title compound was synthesized in analogy to example 66, from (4,4-difluoro-piperidin-1-yl)-[5-(4-dimethylamino-piperidine-1-carbonyl)-1H-indol-2-yl]-methanone (example 140, intermediate a)), 3-cyanophenylboronic acid, copper(II) acetate and pyridine in dichloromethane, to give the desired product as an off-white foam (26%).

MS (ISP): 520.3 (M+H$^+$)

Example 142

(4,4-Difluoro-piperidin-1-yl)-[5-(4-dimethylamino-piperidine-1-carbonyl)-1-(3-trifluoromethyl-phenyl)-1H-indol-2-yl]-methanone The title compound was synthesized in analogy to example 66, from (4,4-difluoro-piperidin-1-yl)-[5-(4-dimethylamino-piperidine-1-carbonyl)-1H-indol-2-yl]-methanone (example 140, intermediate a)), 3-(trifluoromethyl)phenylboronic acid, copper(II) acetate and pyridine in dichloromethane, to give the desired product as a light brown foam (48%).

MS (ISP): 563.4 (M+H$^+$)

Example 143

[1-(4-Chloro-phenyl)-5-(4-dimethylamino-piperidine-1-carbonyl)-1H-indol-2-yl]-(4,4-difluoro-piperidin-1-yl)-methane The title compound was synthesized in analogy to example 66, from (4,4-difluoro-piperidin-1-yl)-[5-(4-dimethylamino-piperidine-1-carbonyl)-1H-indol-2-yl]-methanone (example 140, intermediate a)), 4-chlorophenylboronic acid, copper(II) acetate and pyridine in dichloromethane, to give the desired product as a light brown foam (57%).

MS (ISP): 529.3 (M+H$^+$)

Example 144

4-[2-(4,4-Difluoro-piperidine-1-carbonyl)-5-(4-dimethylamino-piperidine-1-carbonyl)-indol-1-yl]-benzonitrile The title compound was synthesized in analogy to example 66, from (4,4-difluoro-piperidin-1-yl)-[5-(4-dimethylamino-piperidine-1-carbonyl)-1H-indol-2-yl]-methanone (example 140, intermediate a)), 4-cyanophenylboronic acid, copper(II) acetate and pyridine in dichloromethane, to give the desired product as an off-white foam (22%).

MS (TIC): 520.3 (M+H$^+$)

Example 145

(4,4-Difluoro-piperidin-1-yl)-[5-(4-dimethylamino-piperidine-1-carbonyl)-1-(4-trifluoromethyl-phenyl)-1H-indol-2-yl]-methanone The title compound was synthesized in analogy to example 66, from (4,4-difluoro-piperidin-1-yl)-[5-(4-dimethylamino-piperidine-1-carbonyl)-1H-indol-2-yl]-methanone (example 140, intermediate a)), 4-(trifluoromethyl)phenylboronic acid, copper(II) acetate and pyridine in dichloromethane, to give the desired product as a colorless foam (20%).

MS (TIC): 563.4 (M+H$^+$)

Example 146

[1-Cyclopropyl-5-(4-isopropyl-piperazine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), cyclopropylboronic acid (commercially available), copper(II) acetate and pyridine using chloroform as solvent and stirring at 50° C. for 4 days, to give the desired product as a light brown foam (12%).

MS (TIC): 459.3 (M+H$^+$)

Example 147

(4,4-Difluoro-piperidin-1-yl)-[5-(4-isopropyl-piperazine-1-carbonyl)-1-(1-methyl-1-phenyl-ethyl)-1H-indol-2-yl]-methanone The title compound was synthesized in analogy to example 74, from (cyanomethyl)trimethylphosphonium chloride (prepared according to Tetrahedron Lett. 1996, 37 (14), 2459-62), potassium bis(trimethylsilyl)amide, 2-phenyl-2-propanol and (4,4-difluoro-piperidin-1-yl)-[5-(4-isopropyl-piperazine-1-carbonyl)-1H-indol-2-yl]-methanone (example 32), to give the desired product as a yellow foam (9%).
MS (TIC): 537.5 (M+H$^+$)

Example 148

[1-Cyclopropylmethyl-5-(4-dimethylamino-piperidine-1-carbonyl)-1H-indol-2-yl]-(4,4-difluoro-piperidin-1-yl)-methanone The title compound was synthesized in analogy to example 51, from (4,4-difluoro-piperidin-1-yl)-[5-(4-dimethylamino-piperidine-1-carbonyl)-1H-indol-2-yl]-methanone, (example 140, intermediate a)), sodium hydride and cyclopropylmethyl bromide in N,N-dimethylformamide, to give the desired product as a light yellow oil (36%).
MS (TIC): 473.3 (M+H$^+$)

Example 149

(4,4-Difluoro-piperidin-1-yl)-[5-(4-dimethylamino-piperidine-1-carbonyl)-1-(2,2,2-trifluoro-ethyl)-1H-indol-2-yl]-methanone The title compound was synthesized in analogy to example 51, from (4,4-difluoro-piperidin-1-yl)-[5-(4-dimethylamino-piperidine-1-carbonyl)-1H-indol-2-yl]-methanone, (example 140, intermediate a)), sodium hydride and 2,2,2-trifluoroethyl methanesulfonate in N,N-dimethylformamide, to give the desired product as a light yellow foam (63%).
MS (TIC): 501.2 (M+H$^+$)

Example 150

[1-Cyclobutyl-2-(4,4-difluoro-piperidine-1-carbonyl)-1H-indol-5-yl]-(4-isopropyl-piperazin-1-yl)-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), cyclobutylboronic acid (commercially available), copper (II) acetate and pyridine using chloroform as solvent and stirring under reflux for 6 days, to give the desired product as a light brown foam (14%).
MS (TIC): 473.1 (M+H$^+$)

Example 151

[5-(4-Cyclobutyl-piperazine-1-carbonyl)-1-(4-methanesulfonyl-phenyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 4-(methanesulphonyl)benzeneboronic acid, copper(II) acetate and pyridine in dichloromethane, to give the desired product as a light brown solid (12%).
MS (TIC): 585.2 (M+H$^+$)

Example 152

[5-(4-Cyclobutyl-piperazine-1-carbonyl)-1-(3,5-difluoro-phenyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3,5-difluorophenylboronic acid, copper(II) acetate and pyridine in dichloromethane, to give the desired product as a colorless foam (69%).
MS (TIC): 543.3 (M+H$^+$)

Example 153

[1-(2-Chloro-pyridin-4-yl)-5-(4-cyclobutyl-piperazine-1-carbonyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 2-chloropyridine-4-boronic acid, copper(II) acetate and pyridine in dichloromethane, to give the desired product as a off-white foam (10%).
MS (TIC): 542.2 (M+H$^+$)

Example 154

[1-(6-Chloro-pyridin-3-yl)-5-(4-cyclobutyl-piperazine-1-carbonyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 2-chloropyridine-5-boronic acid, copper(II) acetate and pyridine in dichloromethane, to give the desired product as a off-white foam (26%).
MS (TIC): 542.2 (M+H$^+$)

Example 155

[1-Benzo[1,3]dioxol-5-yl-5-(4-cyclobutyl-piperazine-1-carbonyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 3,4-methylenedioxybenzeneboronic acid, copper(II) acetate and pyridine in dichloromethane, to give the desired product as a colorless foam (24%).
MS (TIC): 551.1 (M+H$^+$)

Example 156

[5-(4-Cyclobutyl-piperazine-1-carbonyl)-1-(4-morpholin-4-yl-phenyl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 4-morpholinophenylboronic acid, copper(II) acetate and pyridine in dichloromethane, to give the desired product as a light brown foam (31%).
MS (TIC): 592.3 (M+H$^+$)

Example 157

[5-(4-Cyclobutyl-piperazine-1-carbonyl)-1-(6-morpholin-4-yl-pyridin-3-yl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 2-morpholino-5-pyridineboronic acid, copper(II) acetate and pyridine in dichloromethane, to give the desired product as a light brown foam (29%).
MS (TIC): 593.4 (M+H$^+$)

Example 158

[5-(4-Cyclobutyl-piperazine-1-carbonyl)-1-(2-methoxy-pyrimidin-5-yl)-1H-indol-2-yl]-(4,4-difluoro-piperidin-1-yl)-methanone The title compound was synthesized in analogy to example 66, from [5-(4-cyclobutyl-piperazine-1-carbonyl)-1H-indol-2-yl]-(4,4-difluoro-piperidin-1-yl)-methanone (example 41), 2-methoxypyrimidine-5-boronic acid, copper(II) acetate and pyridine in dichloromethane, to give the desired product as an off-white foam (11%).
MS (TIC): 539.4 (M+H$^+$)

Example 159

(4,4-Difluoro-piperidin-1-yl)-[5-((S)-3-dimethylamino-pyrrolidine-1-carbonyl)-1-(2,2,2-trifluoro-ethyl)-1H-indol-2-yl]-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 42), sodium hydride and 2,2,2-trifluoroethyl methanesulfonate in N,N-dimethylformamide, to give the desired product as a white foam (85%).
MS (TIC): 527.1 (M+H$^+$)

Example 160

(4,4-Difluoro-piperidin-1-yl)-[5-((R)-3-dimethylamino-pyrrolidine-1-carbonyl)-1-(2,2,2-trifluoro-ethyl)-1H-indol-2-yl]-methanone The title compound was synthesized in analogy to example 51, from [2-(4,4-difluoro-piperidine-1-carbonyl)-1H-indol-5-yl]-((R)-2-pyrrolidin-1-ylmethyl-pyrrolidin-1-yl)-methanone (example 43), sodium hydride and 2,2,2-trifluoroethyl methanesulfonate in N,N-dimethylformamide, to give the desired product as a white foam (85%).
MS (TIC): 527.1 (M+H$^+$)

Example 161

N-{4-[5-(4-Cyclobutyl-piperazine-1-carbonyl)-2-(4,4-difluoro-piperidine-1-carbonyl)-indol-1-yl]-phenyl}-methanesulfonamide The title compound was synthesized in analogy to example 66, from [5-(4-cyclobutyl-piperazine-1-carbonyl)-1H-indol-2-yl]-(4,4-difluoro-piperidin-1-yl)-methanone (example 41), 4-(methanesulfonylamino)phenylboronic acid, copper(II) acetate and pyridine in dichloromethane, to give the desired product as a colorless foam (19%).
MS (TIC): 598.2 (M+H$^+$)

Example 162

[1-Cyclopropylmethyl-5-((S)-2-pyrrolidin-1-ylmethyl-pyrrolidine-1-carbonyl)-1H-indol-2-yl]-(4,4-difluoro-piperidin-1-yl)-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and cyclopropylmethyl bromide in N,N-dimethylformamide, to give the desired product as a colorless foam (80%).
MS (TIC): 499.2 (M+H$^+$)

Example 163

(4,4-Difluoro-piperidin-1-yl)-[1-isopropyl-5-((S)-2-pyrrolidin-1-ylmethyl-pyrrolidine-1-carbonyl)-1H-indol-2-yl]-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and 2-bromopropane in N,N-dimethylformamide, to give the desired product as a colorless foam (45%).
MS (TIC): 487.2 (M+H$^+$)

Example 162

(4,4-Difluoro-piperidin-1-yl)-[5-((S)-2-pyrrolidin-1-ylmethyl-pyrrolidine-1-carbonyl)-1-(2,2,2-trifluoro-ethyl)-1H-indol-2-yl]-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and 2,2,2-trifluoroethyl methanesulfonate in N,N-dimethylformamide, to give the desired product as a white foam (85%).
MS (TIC): 527.1 (M+H$^+$)

Example 165

(4,4-Difluoro-piperidin-1-yl)-[1-(2-methoxy-ethyl)-5-((S)-2-pyrrolidin-1-ylmethyl-pyrrolidine-1-carbonyl)-1H-indol-2-yl]-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and 2-bromoethyl methyl ether in N,N-dimethylformamide, to give the desired product as a white foam (69%).

MS (TIC): 503.2 (M+H$^+$)

Example 166

[1-Cyclobutylmethyl-5-((S)-2-pyrrolidin-1-ylmethyl-pyrrolidine-1-carbonyl)-1H-indol-2-yl]-(4,4-difluoro-piperidin-1-yl)-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and (bromomethyl)cyclobutan in N,N-dimethylformamide, to give the desired product as a white foam (73%).

MS (TIC): 513.3 (M+H$^+$)

Example 167

(4,4-Difluoro-piperidin-1-yl)-[1-(2-hydroxy-ethyl)-5-((S)-2-pyrrolidin-1-ylmethyl-pyrrolidine-1-carbonyl)-1H-indol-2-yl]-methanone The solution of 90 mg (0.15 mmol) [1-[2-(tert-butyl-dimethyl-silanyloxy)-ethyl]-5-((S)-2-pyrrolidin-1-ylmethyl-pyrrolidine-1-carbonyl)-1H-indol-2-yl]-(4,4-difluoro-piperidin-1-yl)-methanone in 3 mL dichloromethane was cooled to 0° C. and 1.0 mL (1.49 g, 13.1 mmol) trifluoroacetic acid were added. The cooling bath was removed and after stirring for 1 h at room temperature the pH of the solution was neutralized by adding 1M aqueous sodium hydroxide solution. The phases were separated and the aqueous phase was extracted three times with dichloromethane. The combined organic layers were dried over magnesium sulfate, filtered and evaporated. The crude product was purified by flash column chromatography on silica gel with dichloromethane:methanol as eluant (gradient 100:0 to 50:50) to give 41 mg (56%) of the desired compound as a white foam.

MS (TIC): 489.3 (M+H$^+$)

Intermediate

[1-[2-(tert-Butyl-dimethyl-silanyloxy)-ethyl]-5-((S)-2-pyrrolidin-1-ylmethyl-pyrrolidine-1-carbonyl)-1H-indol-2-yl]-(4,4-difluoro-piperidin-1-yl)-methanone The title compound was synthesized in analogy to example 51, from [2-(4,4-difluoro-piperidine-1-carbonyl)-1H-indol-5-yl]-((S)-2-pyrrolidin-1-ylmethyl-pyrrolidin-1-yl)-methanone (example 44), sodium hydride and (2-bromoethoxy)-tert-butyldimethylsilane (commercially available) in N,N-dimethylformamide, to give the desired product as a colorless oil (44%).

MS (TIC): 603.3 (M+H$^+$)

Example 168

[5-([1,4']Bipiperidinyl-1'-carbonyl)-1H-indol-2-yl]-(4,4-difluoro-piperidin-1-yl)-methanone The title compound was synthesized in analogy to example 1, from 5-([1,4']bipiperidinyl-1'-carbonyl)-1H-indole-2-carboxylic acid; hydrochloride, O-(benzotriazol-1-yl)-N,N,N',N'-tetramethyluronium tetrafluoroborate (commercially available), 4,4-difluoropiperidine (commercially available) and N,N-diisopropyl-ethylamine in N,N-dimethylformamide, to give the desired product as a light yellow solid (44%).

MS (TIC): 458.2 (M+H$^+$)

Intermediates 5-([1,4']Bipiperidinyl-1'-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 4-piperidinopiperidine (commercially available) and N,N-diisopropylethylamine in N,N-dimethylformamide, to give the desired product as a brown solid (67%).

MS (ISP): 370.1 (M+H$^+$)

5-([1,4']Bipiperidinyl-1'-carbonyl)-1H-indole-2-carboxylic acid; hydrochloride

The title compound was synthesized in analogy to example 1, intermediate b), from 5-([1,4']bipiperidinyl-1'-carbonyl)-1H-indole-2-carboxylic acid ethyl ester, to give the desired product as a brown solid (>100%). The so-obtained product was pure enough for the next step without further purification.

MS (ISP): 354.3 (M−H)

Example 169

(4,4-Difluoro-piperidin-1-yl)-[5-(4-pyrrolidin-1-yl-piperidine-1-carbonyl)-1H-indol-2-yl]-methanone The title compound was synthesized in analogy to example 1, from 5-(4-pyrrolidin-1-yl-piperidine-1-carbonyl)-1H-indole-2-carboxylic acid; hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, to give the desired product as a yellow solid (67%).

MS (ISP): 445.1 (M+H$^+$)

Intermediates 5-(4-Pyrrolidin-1-yl-piperidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 4-(1-pyrrolidinyl)-piperidine (commercially available) and N,N-diisopropylethylamine in N,N-dimethylformamide, to give the desired product as a brown solid (67%).

MS (ISP): 370.1 (M+H$^+$)

5-(4-Pyrrolidin-1-yl-piperidine-1-carbonyl)-1H-indole-2-carboxylic acid; hydrochloride The title compound was synthesized in analogy to example 1, intermediate b), from 5-(4-pyrrolidin-1-yl-piperidine-1-carbonyl)-1H-indole-2-carboxylic acid ethyl ester, to give the desired product as a brown solid (>100%). The so-obtained product was pure enough for the next step without further purification.
MS (ISP): 342.0 (M−H)

Example 170

[2-(4,4-Difluoro-piperidine-1-carbonyl)-1H-indol-5-yl]-(4-morpholin-4-yl-piperidin-1-yl)-methanone The title compound was synthesized in analogy to example 1, from 5-(4-morpholin-4-yl-piperidine-1-carbonyl)-1H-indole-2-carboxylic acid; hydrochloride, O-(benzotriazol-1-yl)-N,N,N',N'-tetramethyluronium tetrafluoroborate (commercially available), 4,4-difluoropiperidine (commercially available) and N,N-diisopropylethylamine in N,N-dimethylformamide, to give the desired product as a brown solid (86%).
MS (ISP): 461.1 (M+H$^+$)

Intermediates 5-(4-Morpholin-4-yl-piperidine-1-carbonyl)-1H-indole-2-carboxylic acid ethyl ester The title compound was synthesized in analogy to example 1, intermediate a), from 1H-indole-2,5-dicarboxylic acid 2-ethyl ester, O-(benzotriazol-1-yl)-N,N,N',N'-tetramethyluronium tetrafluoroborate (commercially available), 4-(piperidin-4-yl)-morpholine (commercially available) and N,N-diisopropylethylamine in N,N-dimethylformamide, to give the desired product as a light yellow foam (72%).
MS (ISP): 386.2 (M+H$^+$)

5-(4-Morpholin-4-yl-piperidine-1-carbonyl)-1H-indole-2-carboxylic acid; hydrochloride The title compound was synthesized in analogy to example 1, intermediate b), from 5-(4-morpholin-4-yl-piperidine-1-carbonyl)-1H-indole-2-carboxylic acid ethyl ester, to give the desired product as a brown solid (>100%). The so-obtained product was pure enough for the next step without further purification.

a anti-hypertensive agent.

Example 171

[5-([1,4']Bipiperidinyl-1'-carbonyl)-1-cyclopropylmethyl-1H-indol-2-yl]-(4,4-difluoro-piperidin-1-yl)-methanone The title compound was synthesized in analogy to example 51, from [5-([1,4']bipiperidinyl-1'-carbonyl)-1H-indol-2-yl]-(4,4-difluoro-piperidin-1-yl)-methanone (example 168), sodium hydride and cyclopropylmethyl bromide in N,N-dimethylformamide, to give the desired product as a colorless solid (91%).
MS (ISP): 513.4 (M+H$^+$)

Example 172

[5-([1,4']Bipiperidinyl-1'-carbonyl)-1-(2,2,2-trifluoro-ethyl)-1H-indol-2-yl]-(4,4-difluoro-piperidin-1-yl)-methanone The title compound was synthesized in analogy to example 51, from [5-([1,4']bipiperidinyl-1'-carbonyl)-1H-indol-2-yl]-(4,4-difluoro-piperidin-1-yl)-methanone (example 168), sodium hydride and 2,2,2-trifluoroethyl methanesulfonate in N,N-dimethylformamide to give the desired product as a colorless solid (89%).
MS (ISP): 541.2 (M+H$^+$)

Example 173

[5-([1,4']Bipiperidinyl-1'-carbonyl)-1-isopropyl-1H-indol-2-yl]-(4,4-difluoro-piperidin-1-yl)-methanone The title compound was synthesized in analogy to example 51, from [5-([1,4']bipiperidinyl-1'-carbonyl)-1H-indol-2-yl]-(4,4-difluoro-piperidin-1-yl)-methanone (example 168), sodium hydride and 2-bromopropane in N,N-dimethylformamide, to give the desired product as a brown oil (62%).
MS (ISP): 501.4 (M+H$^+$)

Example 174

[5-([1,4']Bipiperidinyl-1'-carbonyl)-1-(2-chloro-pyridin-4-yl)-1H-indol-2-yl]-(4,4-difluoro-piperidin-1-yl)-methanone The title compound was synthesized in analogy to example 66, from [5-([1,4']bipiperidinyl-1'-carbonyl)-1H-indol-2-yl]-(4,4-difluoro-piperidin-1-yl)-methanone (example 168), 2-chloropyridine-4-boronic acid, copper(II) acetate and pyridine in dichloromethane, to give the desired product as a yellow solid (35%).
MS (ISP): 570.3 (M+H$^+$)

Example 175

[5-([1,4']Bipiperidinyl-1'-carbonyl)-1-(3-chloro-phenyl)-1H-indol-2-yl]-(4,4-difluoro-piperidin-1-yl)-methanone The title compound was synthesized in analogy to example 66, from [5-([1,4']bipiperidinyl-1'-carbonyl)-1H-indol-2-yl]-(4,4-difluoro-piperidin-1-yl)-methanone (example 168), 3-chlorophenylboronic acid, copper(II) acetate and pyridine in dichloromethane, to give the desired product as a light red solid (77%).
MS (ISP): 569.4 (M+H$^+$)

Example 176

[5-([1,4']Bipiperidinyl-1'-carbonyl)-1-(3-trifluoromethyl-phenyl)-1H-indol-2-yl]-(4,4-difluoro-piperidin-1-yl)-methanone The title compound was synthesized in analogy to example 66, from [5-([1,4']bipiperidinyl-1'-carbonyl)-1H-indol-2-yl]-(4,4-difluoro-piperidin-1-yl)-methanone (example 168), 3-(trifluoromethyl)phenylboronic acid, copper(II) acetate and pyridine in dichloromethane, to give the desired product as a brown oil (66%).
MS (ISP): 603.2 (M+H$^+$)

Example 177

[5-([1,4]Bipiperidinyl-1'-carbonyl)-1-(6-chloro-pyridin-3-yl)-1H-indol-2-yl]-(4,4-difluoro-piperidin-1-yl)-methanone The title compound was synthesized in analogy to example 66, from [5-([1,4']bipiperidinyl-1'-carbonyl)-1H-indol-2-yl]-(4,4-difluoro-piperidin-1-yl)-methanone (example 168), 2-chloropyridine-5-boronic acid, copper(II) acetate and pyridine in dichloromethane, to give the desired product as a brown oil (57%).

MS (ISP): 570.3 (M+H$^+$)

Example 178

[1-Cyclopropylmethyl-5-(4-pyrrolidin-1-yl-piperidine-1-carbonyl)-1H-indol-2-yl]-(4,4-difluoro-piperidin-1-yl)-methanone The title compound was synthesized in analogy to example 51, from (4,4-difluoro-piperidin-1-yl)-[5-(4-pyrrolidin-1-yl-piperidine-1-carbonyl)-1H-indol-2-yl]-methanone (example 169), sodium hydride and cyclopropylmethyl bromide in N,N-dimethylformamide, to give the desired product as a yellow solid (53%).

MS (ISP): 499.3 (M+H$^+$)

Example 179

(4,4-Difluoro-piperidin-1-yl)-[5-(4-pyrrolidin-1-yl-piperidine-1-carbonyl)-1-(2,2,2-trifluoro-ethyl)-1H-indol-2-yl]-methanone The title compound was synthesized in analogy to example 51, from (4,4-difluoro-piperidin-1-yl)-[5-(4-pyrrolidin-1-yl-piperidine-1-carbonyl)-1H-indol-2-yl]-methanone (example 169), sodium hydride and 2,2,2-trifluoroethyl methanesulfonate in N,N-dimethylformamide to give the desired product as a yellow solid (46%).

MS (ISP): 527.2 (M+H$^+$)

Example 180

(4,4-Difluoro-piperidin-1-yl)-[1-isopropyl-5-(4-pyrrolidin-1-yl-piperidine-1-carbonyl)-1H-indol-2-yl]-methanone The title compound was synthesized in analogy to example 51, from (4,4-difluoro-piperidin-1-yl)-[5-(4-pyrrolidin-1-yl-piperidine-1-carbonyl)-1H-indol-2-yl]-methanone (example 169), sodium hydride and 2-bromopropane in N,N-dimethylformamide, to give the desired product as a white solid (66%).

MS (ISP): 487.5 (M+H$^+$)

Example 181

[1-(2-Chloro-pyridin-4-yl)-5-(4-pyrrolidin-1-yl-piperidine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-pyrrolidin-1-yl-piperidine-1-carbonyl)-1H-indol-2-yl]-methanone (example 169), 2-chloropyridine-4-boronic acid, copper(II) acetate and pyridine in dichloromethane, to give the desired product as a yellow oil (17%).

MS (ISP): 556.1 (M+H$^+$)

Example 182

[1-(3-Chloro-phenyl)-5-(4-pyrrolidin-1-yl-piperidine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-pyrrolidin-1-yl-piperidine-1-carbonyl)-1H-indol-2-yl]-methanone (example 169), 3-chlorophenylboronic acid, copper(II) acetate and pyridine in dichloromethane, to give the desired product as a brown oil (93%).

Example 183

(4,4-Difluoro-piperidin-1-yl)-[5-(4-pyrrolidin-1-yl-piperidine-1-carbonyl)-1-(3-trifluoromethyl-phenyl)-1H-indol-2-yl]-methanone The title compound was synthesized in analogy to example 66, from (4,4-difluoro-piperidin-1-yl)-[5-(4-pyrrolidin-1-yl-piperidine-1-carbonyl)-1H-indol-2-yl]-methanone (example 169), 3-(trifluoromethyl)phenylboronic acid, copper(II) acetate and pyridine in dichloromethane, to give the desired product as a brown oil (53%).

MS (ISP): 589.4 (M+H$^+$)

Example 184

[1-(6-Chloro-pyridin-3-yl)-5-(4-pyrrolidin-1-yl-piperidine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-pyrrolidin-1-yl-piperidine-1-carbonyl)-1H-indol-2-yl]-methanone (example 169), 2-chloropyridine-5-boronic acid, copper(II) acetate and pyridine in dichloromethane, to give the desired product as a brown oil (57%).

MS (ISP): 556.1 (M+H$^+$)

Example 185

[1-Cyclopropylmethyl-5-(4-morpholin-4-yl-piperidine-1-carbonyl)-1H-indol-2-yl]-(4,4-difluoro-piperidin-1-yl)-methanone The title compound was synthesized in analogy to example 51, from [2-(4,4-difluoro-piperidine-1-carbonyl)-1H-indol-5-yl]-(4-morpholin-4-yl-piperidin-1-yl)-methanone (example 170), sodium hydride and cyclopropylmethyl bromide in N,N-dimethylformamide, to give the desired product as a white solid (16%).

MS (ISP): 515.4 (M+H$^+$)

Example 186

(4,4-Difluoro-piperidin-1-yl)-[5-(4-morpholin-4-yl-piperidine-1-carbonyl)-1-(2,2,2-trifluoro-ethyl)-1H-indol-2-yl]-methanone The title compound was synthesized in analogy to example 51, from [2-(4,4-difluoro-piperidine-1-carbonyl)-1H-indol-5-yl]-(4-morpholin-4-yl-piperidin-1-yl)-methanone (example 170), sodium hydride and 2,2,2-trifluoroethyl methanesulfonate in N,N-dimethylformamide, to give the desired product as a brown oil (56%).

MS (ISP): 543.3 (M+H$^+$)

Example 187

(4,4-Difluoro-piperidin-1-yl)-[1-isopropyl-5-(4-morpholin-4-yl-piperidine-1-carbonyl)-1H-indol-2-yl]-methanone The title compound was synthesized in analogy to example 51, from [2-(4,4-difluoro-piperidine-1-carbonyl)-1H-indol-5-yl]-(4-morpholin-4-yl-piperidin-1-yl)-methanone (example 170), sodium hydride and 2-bromopropane in N,N-dimethylformamide, to give the desired product as a brown oil (88%).

MS (ISP): 503.4 (M+H$^+$)

Example 188

[1-(3-Chloro-phenyl)-5-(4-morpholin-4-yl-piperidine-1-carbonyl)-1H-indol-2-yl]-(4,4-difluoro-piperidin-1-yl)-methanone The title compound was synthesized in analogy to example 66, from [2-(4,4-difluoro-piperidine-1-carbonyl)-1H-indol-5-yl]-(4-morpholin-4-yl-piperidin-1-yl)-methanone (example 170), 3-chlorophenylboronic acid, copper(II) acetate and pyridine in dichloromethane, to give the desired product as a white solid (64%).

MS (ISP): 571.3 (M+H$^+$)

Example 189

(4,4-Difluoro-piperidin-1-yl)-[5-(4-morpholin-4-yl-piperidine-1-carbonyl)-1-(3-trifluoromethyl-phenyl)-1H-indol-2-yl]-methanone The title compound was synthesized in analogy to example 66, from [2-(4,4-difluoro-piperidine-1-carbonyl)-1H-indol-5-yl]-(4-morpholin-4-yl-piperidin-1-yl)-methanone (example 170), 3-(trifluoromethyl)phenylboronic acid, copper(II) acetate and pyridine in dichloromethane, to give the desired product as a brown oil (60%).

MS (ISP): 605.2 (M+H$^+$)

Example 190

[1-(6-Chloro-pyridin-3-yl)-5-(4-morpholin-4-yl-piperidine-1-carbonyl)-1H-indol-2-yl]-(4,4-difluoro-piperidin-1-yl)-methanone The title compound was synthesized in analogy to example 66, from [2-(4,4-difluoro-piperidine-1-carbonyl)-1H-indol-5-yl]-(4-morpholin-4-yl-piperidin-1-yl)-methanone (example 170), 2-chloropyridine-5-boronic acid, copper(II) acetate and pyridine in dichloromethane, to give the desired product as a yellow solid (31%).

MS (TS): 572.3 (M+H$^+$)

Example 191

[1-Cyclopropylmethyl-5-(4-isopropyl-piperazine-1-carbonyl)-1H-indol-2-yl]-(4-methoxy-piperidin-1-yl)-methanone The title compound was synthesized in analogy to example 51, from [5-(4-isopropyl-piperazine-1-carbonyl)-1H-indol-2-yl]-(4-methoxy-piperidin-1-yl)-methanone (example 21), sodium hydride and cyclopropylmethyl bromide in N,N-dimethylformamide, to give the desired product as a colorless foam (62%).

MS (ISP): 467.4 (M+H$^+$)

Example 192

[5-(4-Isopropyl-piperazine-1-carbonyl)-1-(2,2,2-trifluoro-ethyl)-1H-indol-2-yl]-(4-methoxy-piperidin-1-yl)-methanone The title compound was synthesized in analogy to example 51, from [5-(4-isopropyl-piperazine-1-carbonyl)-1H-indol-2-yl]-(4-methoxy-piperidin-1-yl)-methanone (example 21), sodium hydride and 2,2,2-trifluoroethyl methanesulfonate in N,N-dimethylformamide, to give the desired product as a light brown foam (83%).

MS (ISP): 495.4 (M+H$^+$)

Example 193

[1-(3-Chloro-phenyl)-5-(4-isopropyl-piperazine-1-carbonyl)-1H-indol-2-yl]-(4-methoxy-piperidin-1-yl)-methanone The title compound was synthesized in analogy to example 66, from [5-(4-isopropyl-piperazine-1-carbonyl)-1H-indol-2-yl]-(4-methoxy-piperidin-1-yl)-methanone (example 21), 3-chlorophenylboronic acid, copper(II) acetate and pyridine in dichloromethane, to give the desired product as a colorless foam (43%).

MS (ISP): 523.3 (M+H$^+$)

Example 194

[5-(4-Isopropyl-piperazine-1-carbonyl)-1-(3-trifluoromethyl-phenyl)-1H-indol-2-yl]-(4-methoxy-piperidin-1-yl)-methanone The title compound was synthesized in analogy to example 66, from [5-(4-isopropyl-piperazine-1-carbonyl)-1H-indol-2-yl]-(4-methoxy-piperidin-1-yl)-methanone (example 21), 3-(trifluoromethyl)phenylboronic acid, copper(II) acetate and pyridine in dichloromethane, to give the desired product as a colorless foam (65%).

MS (ISP): 557.4 (M+H$^+$)

Example 195

[1-(2-Chloro-pyridin-4-yl)-5-(4-isopropyl-piperazine-1-carbonyl)-1H-indol-2-yl]-(4-methoxy-piperidin-1-yl)-methanone The title compound was synthesized in analogy to example 66, from [5-(4-isopropyl-piperazine-1-carbonyl)-1H-indol-2-yl]-(4-methoxy-piperidin-1-yl)-methanone (example 21), 2-chloropyridine-4-boronic acid, copper(II) acetate and pyridine in dichloromethane, to give the desired product as a light brown foam (33%).

MS (ISP): 524.3 (M+H$^+$)

Example 196

(1,4-Dioxa-8-aza-spiro[4.5]dec-8-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid 1:1 hydrochlorid (example 1, intermediate b), O-(benzotriazol-1-yl)-N,N,N',N'-tetramethyluronium tetrafluoroborate (commercially available), 1,4-dioxa-8-aza-spiro[4.5]decane (commercially available) and N,N-diisopropylethylamine in N,N-dimethylformamide, to give the desired product as a light brown solid (64%).

MS (ISP): 441.2 (M+H$^+$)

Example 197

[1-Cyclopropylmethyl-5-(4-isopropyl-piperazine-1-carbonyl)-1H-indol-2-yl]-(1,4-dioxa-8-aza-spiro[4.5]dec-8-yl)-methanone The title compound was synthesized in analogy to example 51, from (1,4-dioxa-8-aza-spiro[4.5]dec-8-yl)-[5-(4-isopropyl-piperazine-1-carbonyl)-1H-indol-2-yl]-methanone (example 196), sodium hydride and cyclopropylmethyl bromide in N,N-dimethylformamide, to give the desired product as a colorless foam (76%).

MS (ISP): 495.4 (M+H$^+$)

Example 198

(1,4-Dioxa-8-aza-spiro[4.5]dec-8-yl)-[5-(4-isopropyl-piperazine-1-carbonyl)-1-(2,2,2-trifluoro-ethyl)-1H-indol-2-yl]-methanone The title compound was synthesized in analogy to example 51, from (1,4-dioxa-8-aza-spiro[4.5]dec-8-yl)-[5-(4-isopropyl-piperazine-1-carbonyl)-1H-indol-2-yl]-methanone (example 196), sodium hydride and 2,2,2-trifluoroethyl methanesulfonate in N,N-dimethylformamide, to give the desired product as a colorless foam (78%).

MS (ISP): 523.4 (M+H$^+$)

Example 199

[1-(3-Chloro-phenyl)-5-(4-isopropyl-piperazine-1-carbonyl)-1H-indol-2-yl]-(1,4-dioxa-8-aza-spiro[4.5]dec-8-yl)-methanone The title compound was synthesized in analogy to example 66, from (1,4-dioxa-8-aza-spiro[4.5]dec-8-yl)-[5-(4-isopropyl-piperazine-1-carbonyl)-1H-indol-2-yl]-methanone (example 196), 3-chlorophenylboronic acid, copper(II) acetate and pyridine in dichloromethane, to give the desired product as a light brown foam (50%).

MS (ISP): 551.2 (M+H$^+$)

Example 200

(1,4-Dioxa-8-aza-spiro[4.5]dec-8-yl)-[5-(4-isopropyl-piperazine-1-carbonyl)-1-(3-trifluoromethyl-phenyl)-1H-indol-2-yl]-methanone The title compound was synthesized in analogy to example 66, from (1,4-dioxa-8-aza-spiro[4.5]dec-8-yl)-[5-(4-isopropyl-piperazine-1-carbonyl)-1H-indol-2-yl]-methanone (example 196), 3-(trifluoromethyl)phenylboronic acid, copper (II) acetate and pyridine in dichloromethane, to give the desired product as a colorless foam (55%).

MS (ISP): 585.2 (M+H$^+$)

Example 201

[1-(2-Chloro-pyridin-4-yl)-5-(4-isopropyl-piperazine-1-carbonyl)-1H-indol-2-yl]-(1,4-dioxa-8-aza-spiro[4.5]dec-8-yl)-methanone The title compound was synthesized in analogy to example 66, from (1,4-dioxa-8-aza-spiro[4.5]dec-8-yl)-[5-(4-isopropyl-piperazine-1-carbonyl)-1H-indol-2-yl]-methanone (example 196), 2-chloropyridine-4-boronic acid, copper(II) acetate and pyridine in dichloromethane, to give the desired product as a light brown foam (42%).

MS (ISP): 552.3 (M+H$^+$)

Example 202

[5-(4-Cyclobutyl-piperazine-1-carbonyl)-1H-indol-2-yl]-(1,1-dioxothiomorpholin-4-yl)-methanone The title compound was synthesized in analogy to example 1, from 5-(4-cyclobutyl-piperazine-1-carbonyl)-1H-indole-2-carboxylic acid hydrochloride (example 41, intermediate b)), O-(benzotriazol-1-yl)-N,N,N',N'-tetramethyluronium tetrafluoroborate (commercially available) and N,N-diisopropylethylamine in N,N-dimethylformamide, to give the desired product as a light brown solid (82%).

MS (ISP): 445.2 (M+H$^+$)

Example 203

[5-(4-Cyclobutyl-piperazine-1-carbonyl)-1-cyclopropylmethyl-1H-indol-2-yl]-(1,1-dioxothiomorpholin-4-yl)-methanone The title compound was synthesized in analogy to example 51, from [5-(4-cyclobutyl-piperazine-1-carbonyl)-1H-indol-2-yl]-(1,1-dioxothiomorpholin-4-yl)-methanone (example 202), sodium hydride and cyclopropylmethyl bromide in N,N-dimethylformamide, to give the desired product as a colorless foam (80%).

MS (ISP): 499.2 (M+H$^+$)

Example 204

[5-(4-Cyclobutyl-piperazine-1-carbonyl)-1-(2,2,2-trifluoro-ethyl)-1H-indol-2-yl]-(1,1-dioxothiomorpholin-4-yl)-methanone The title compound was synthesized in analogy to example 51, from [5-(4-cyclobutyl-piperazine-1-carbonyl)-1H-indol-2-yl]-(1,1-dioxothiomorpholin-4-yl)-methanone (example 202), sodium hydride and 2,2,2-trifluoroethyl methanesulfonate in N,N-dimethylformamide, to give the desired product as a yellow solid (73%).

MS (ISP): 527.1 (M+H$^+$)

Example 205

[5-(4-Cyclobutyl-piperazine-1-carbonyl)-1-isopropyl-1H-indol-2-yl]-(1,1-dioxothiomorpholin-4-yl)-methanone The title compound was synthesized in analogy to example 51, from [5-(4-cyclobutyl-piperazine-1-carbonyl)-1H-indol-2-yl]-(1,1-dioxothiomorpholin-4-yl)-methanone (example 202), sodium hydride and 2-bromopropane in N,N-dimethylformamide, to give the desired product as a light brown foam (49%).

MS (ISP): 487.2 (M+H$^+$)

Example 206

[5-(4-Cyclobutyl-piperazine-1-carbonyl)-2-(1,1-dioxothiomorpholine-4-carbonyl)-indol-1-yl]-acetonitrile The title compound was synthesized in analogy to example 51, from [5-(4-cyclobutyl-piperazine-1-carbonyl)-1H-indol-2-yl]-(1,1-dioxothiomorpholin-4-yl)-methanone (example 202), sodium hydride and bromoacetonitrile in N,N-dimethylformamide, to give the desired product as a yellow gum (7%).

MS (ISP): 484.3 (M+H$^+$)

Example 207

[5-(4-Cyclobutyl-piperazine-1-carbonyl)-1-(3-fluoro-phenyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-fluorophenylboronic acid, copper(II) acetate and pyridine in dichloromethane, to give the desired product as a colorless solid (35%).

MS (ISP): 539.4 (M+H$^+$)

Example 208

[5-(4-Cyclobutyl-piperazine-1-carbonyl)-1-m-tolyl-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-methylphenylboronic acid, copper(II) acetate and pyridine in dichloromethane, to give the desired product as a colorless foam (56%).

MS (ISP): 535.4 (M+H$^+$)

Example 209

[1-(3-Chloro-phenyl)-5-(4-cyclobutyl-piperazine-1-carbonyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-chlorophenylboronic acid, copper(II) acetate and pyridine in dichloromethane, to give the desired product as a colorless foam (72%).

MS (ISP): 555.2 (M+H$^+$)

Example 210

[5-(4-Cyclobutyl-piperazine-1-carbonyl)-1-(3-trifluoromethyl-phenyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-(trifluoromethyl)phenylboronic acid, copper(II) acetate and pyridine in dichloromethane, to give the desired product as a colorless foam (60%).

MS (ISP): 589.5 (M+H$^+$)

Example 211

3-[5-(4-Cyclobutyl-piperazine-1-carbonyl)-2-(1,1-dioxothiomorpholine-4-carbonyl)-indol-1-yl]-benzonitrile The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-cyanophenylboronic acid, copper(II) acetate and pyridine in dichloromethane, to give the desired product as a colorless foam (49%).

MS (ISP): 546.3 (M+H$^+$)

Example 212

[5-(4-Cyclobutyl-piperazine-1-carbonyl)-1-(3-methanesulfonyl-phenyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-methylsulfonylphenylboronic acid, copper(II) acetate and pyridine in dichloromethane, to give the desired product as a colorless foam (37%).

MS (ISP): 599.3 (M+H$^+$)

Example 213

[5-(4-Cyclobutyl-piperazine-1-carbonyl)-1-(3-trifluoromethoxy-phenyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 3-(trifluoromethoxy)phenylboronic acid, copper(II) acetate and pyridine in dichloromethane, to give the desired product as a light brown foam (61%).

MS (ISP): 605.2 (M+H$^+$)

Example 214

[1-(2-Chloro-pyridin-4-yl)-5-(4-cyclobutyl-piperazine-1-carbonyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 2-chloropyridine-4-boronic acid, copper(II) acetate and pyridine in dichloromethane, to give the desired product as a colorless foam (32%).

MS (ISP): 556.1 (M+H$^+$)

Example 215

[1-(6-Chloro-pyridin-3-yl)-5-(4-cyclobutyl-piperazine-1-carbonyl)-1H-indol-2-yl]-(1,1-dioxothiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 2-chloropyridine-5-boronic acid, copper(II) acetate and pyridine in dichloromethane, to give the desired product as a colorless foam (54%).

MS (ISP): 556.1 (M+H$^+$)

Example 216

[5-(4-Cyclobutyl-piperazine-1-carbonyl)-1-(4-methanesulfonyl-phenyl)-1H-indol-2-yl]-(1,1-dioxo-thiomorpholin-4-yl)-methanone The title compound was synthesized in analogy to example 66, from [5-(4-cyclobutyl-piperazine-1-carbonyl)-1H-indol-2-yl]-(1,1-dioxothiomorpholin-4-yl)-methanone (example 202), 4-methylsulfonylphenylboronic acid, copper(II) acetate and pyridine in dichloromethane, to give the desired product as a light brown solid (41%).

MS (ISP): 599.3 (M+H$^+$)

Example 217

(1,1-Dioxothiomorpholin-4-yl)-[1-isopropyl-5-(4-isopropyl-piperazine-1-carbonyl)-1H-indol-2-yl]-methanone The title compound was synthesized in analogy to example 51, from [2-(1,1-dioxo-thiomorpholine-4-carbonyl)-1H-indol-5-yl]-(4-isopropyl-piperazin-1-yl)-methanone (example 1), sodium hydride and 2-bromopropane in N,N-dimethylformamide, to give the desired product as a light brown foam (42%).

MS (ISP): 475.1 (M+H$^+$)

Example 218

[2-(1,1-Dioxothiomorpholine-4-carbonyl)-5-(4-isopropyl-piperazine-1-carbonyl)-indol-1-yl]-acetonitrile The title compound was synthesized in analogy to example 51, from [2-(1,1-dioxo-thiomorpholine-4-carbonyl)-1H-indol-5-yl]-(4-isopropyl-piperazin-1-yl)-methanone (example 1), sodium hydride and bromoacetonitrile in N,N-dimethylformamide, to give the desired product as a brown gum (11%).

MS (ISP): 472.0 (M+H$^+$)

Example 219

(1,1-Dioxo-thiomorpholin-4-yl)-[5-(4-isopropyl-piperazine-1-carbonyl)-1-m-tolyl-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-methylphenylboronic acid, copper(II) acetate, pyridine and using chloroforme instead of dichloromethane as solvent, to give the desired product as a colorless foam (94%).

MS (ISP): 523.3 (M+H$^+$)

Example 220

(1,1-Dioxothiomorpholin-4-yl)-[1-(3-fluoro-phenyl)-5-(4-isopropyl-piperazine-1-carbonyl)-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-fluorophenylboronic acid, copper(II) acetate, pyridine and using chloroforme instead of dichloromethane as solvent, to give the desired product as a colorless foam (35%).

MS (ISP): 527.2 (M+H$^+$)

Example 221

(1,1-Dioxothiomorpholin-4-yl)-[5-(4-isopropyl-piperazine-1-carbonyl)-1-(4-methanesulfonyl-phenyl)-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 4-methylsulfonylphenylboronic acid, copper(II) acetate, pyridine and using chloroforme instead of dichloromethane as solvent, to give the desired product as a colorless solid (25%).

MS (ISP): 587.4 (M+H$^+$)

Example 222

[1-(2-Chloro-pyridin-4-yl)-5-(4-isopropyl-piperazine-1-carbonyl)-1H-indol-2-yl]-(1,1-dioxothiomorpholin-4-yl)-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 2-chloropyridine-4-boronic acid, copper(II) acetate, pyridine and using chloroforme instead of dichloromethane as solvent, to give the desired product as a light brown solid (10%).

MS (ISP): 544.3 (M+H$^+$)

Example 223

[1-(6-Chloro-pyridin-3-yl)-5-(4-isopropyl-piperazine-1-carbonyl)-1H-indol-2-yl]-(1,1-dioxothiomorpholin-4-yl)-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 2-chloropyridine-5-boronic acid, copper(II) acetate, pyridine and using chloroforme instead of dichloromethane as solvent, to give the desired product as a light brown solid (19%).

MS (ISP): 544.3 (M+H$^+$)

Example 224

(1,1-Dioxothiomorpholin-4-yl)-[5-(4-isopropyl-piperazine-1-carbonyl)-1-(3-methanesulfonyl-phenyl)-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), 3-methylsulfonylphenylboronic acid, copper(II) acetate, pyridine and using chloroforme instead of dichloromethane as solvent, to give the desired product as a colorless solid (16%).

MS (ISP): 587.4 (M+H$^+$)

Example 225

(1,1-Dioxothiomorpholin-4-yl)-[5-(4-isopropyl-piperazine-1-carbonyl)-1-pyrimidin-5-yl-1H-indol-2-yl]-methanone The title compound was synthesized in analogy to example 66, from [2-(1,1-dioxo-thiomorpholine-4-carbonyl)-1H-indol-5-yl]-(4-isopropyl-piperazin-1-yl)-methanone (example 1), pyrimidine-5-boronic acid, copper(II) acetate, pyridine and using chloroforme instead of dichloromethane as solvent, to give the desired product as a colorless solid (8%).

MS (ISP): 511.3 (M+H$^+$)

Example 226

[1-(2-Chloro-pyridin-4-yl)-5-(4-isopropyl-piperazine-1-carbonyl)-1H-indol-2-yl]-(4,4-difluoro-piperidin-1-yl)-methanone The title compound was synthesized in analogy to example 66, from (4,4-difluoro-piperidin-1-yl)-[5-(4-isopropyl-piperazine-1-carbonyl)-1H-indol-2-yl]-methanone (example 32), 2-chloropyridine-4-boronic acid, copper(II) acetate, pyridine and using chloroforme instead of dichloromethane as solvent, to give the desired product as a light yellow foam (20%).

MS (ISP): 530.2 (M+H$^+$)

Examples 227 and 228

[4-Chloro-2-(4,4-difluoro-piperidine-1-carbonyl)-1H-indol-5-yl]-(4-isopropyl-piperazin-1-yl)-methanone and [6-Chloro-2-(4,4-difluoro-piperidine-1-carbonyl)-1H-indol-5-yl]-(4-isopropyl-piperazin-1-yl)-methanone The title compounds were synthesized in analogy to example 1, from 4-chloro- or 6-chloro-5-(4-isopropyl-piperazine-1-carbonyl)-1H-indole-2-carboxylic acid; hydrochloride (intermediates c), O-(benzotriazol-1-yl)-N,N,N',N'-tetramethyluronium tetrafluoroborate (commercially available), 2,4-difluoro piperidine (commercially available) and N,N-diisopropylethylamine in N,N-dimethylformamide, to give the desired products as colorless solids in 66% (4-chloro) and 75% (6-chloro) yield.

MS (ISP): 453.3 (M+H$^+$) both isomers

Intermediates

2-Chloro-4-{N'-[1-ethoxycarbonyl-eth-(E/Z)-ylidene]-hydrazino}-benzoic acid

To the suspension of 1.1 g (4.93 mmol) 2-chloro-4-hydrazino-benzoic acid hydrochloride in 11 mL ethanol, 0.84 mL (0.637 g, 4.93 mmol) N,N-diisopropyl-ethylamine and 0.66 mL (0.687 g, 5.92 mmol) ethyl pyruvate were added and the turbid solution was stirred under reflux for 2.75 hrs. After cooling down to room temperature, the suspension was filtered and the filter cake was washed with ethanol to give a first batch of the desired product (light brown solid; 31%). The mother liquor was kept overnight in a refrigerator and the resulting suspension was filtered again to give a second batch of compound (light brown solid; 13%).

MS (ISP): 283.2 (M+H$^+$)

4-Chloro-5-(4-isopropyl-piperazine-1-carbonyl)-1H-indole-2-carboxylic acid ethyl ester and 6-chloro-5-(4-isopropyl-piperazine-1-carbonyl)-1H-indole-2-carboxylic acid ethyl ester The mixture of 7.85 g (27.6 mmol) 2-chloro-4-{N'-[1-ethoxycarbonyl-eth-(E/Z)-ylidene]-hydrazino}-benzoic acid and 52.6 g (0.386 mol) zinc chloride was heated under stirring to 180° C. After 10 min. the heating bath was removed and 125 mL water and 4.64 mL concentrated hydrochloric acid were added. The reaction mixture was homogenized in an ultrasonic bath and then refluxed for 1 h. The resulting homogenous suspension was put in a refrigerator for 16 hrs, filtered, washed with water and dried to give 5 g of a light brown solid containing a mixture of both 4-chloro- and 6-chloro-1H-indole-2,5-dicarboxylic acid 2-ethyl ester (MS (ISP): 222.2 (M−H$^+$)).

This mixture was dissolved in 50 mL N,N-dimethylformamide and 7.5 g (23.3 mmol) O-benzotriazol-1-yl-N,N,N',N'-tetramethyluronium tetrafluoroborate were added. After 10 min., 2.99 g (23.3 mmol) 1-isopropylpiperazine (commercially available) was added, the solution was cooled to 0° C. and 15.9 mL (12.1 g, 93.6 mmol) N,N-diisopropylethylamine were added. The cooling bath was removed and after stirring for 1.25 hrs at room temperature, the reaction solution was poured on 300 mL saturated aqueous sodium bicarbonate solution and extracted three times with ethyl acetate. The combined organic layers were washed with three times with water followed by brine, dried over magnesium sulfate, filtered and evaporated. The residue was chromatographed on silica gel with dichloromethane:methanol (1:1 v/v) as eluant and both compounds were individually purified by silica gel column chromatography using isopropyl acetate:methanol (9:1 v/v) as eluant to give 175 mg (2.5%; light brown solid) of the 4-chloro and 229 mg (3.2%, off-white solid) of the 6-chloro-5-(4-isopropyl-piperazine-1-carbonyl)-1H-indole-2-carboxylic acid ethyl ester, respectively.

MS (ISP): 378.2 (M+H$^+$). 4-Chloro isomer MS (ISP): 378.4 (M+H$^+$). 6-Chloro isomer 4-Chloro-5-(4-isopropyl-piperazine-1-carbonyl)-1H-indole-2-carboxylic acid; hydrochloride and 6-Chloro-5-(4-isopropyl-piperazine-1-carbonyl)-1H-indole-2-carboxylic acid; hydrochloride The title compounds were synthesized in analogy to example 1, intermediate b), from 4- or 6-chloro-5-(4-isopropyl-piperazine-1-carbonyl)-1H-indole-2-carboxylic acid ethyl ester, to give the title compounds as brown (4-chloro isomer) or colorless solids (6-chloro isomer) in quantitative yields. The compounds were pure enough for the next step without further purification.

MS (ISP): 350.3 (M+H$^+$). 4-Chloro isomer MS (ISP): 350.3 (M+H$^+$). 6-Chloro isomer Example 229

[6-Chloro-1-(2-chloro-pyridin-4-yl)-5-(4-isopropyl-piperazine-1-carbonyl)-1H-indol-2-yl]-(4,4-difluoro-piperidin-1-yl)-methanone The title compound was synthesized in analogy to example 66, from [6-chloro-2-(4,4-difluoro-piperidine-1-carbonyl)-1H-indol-5-yl]-(4-isopropyl-piperazin-1-yl)-methanone (example 227), 2-chloropyridine-4-boronic acid, copper(II) acetate, pyridine and using chloroforme instead of dichloromethane as solvent, to give the desired product as a colorless foam (19%).

MS (ISP): 564.4 (M+H$^+$)

Example 230

[4-Chloro-1-(2-chloro-pyridin-4-yl)-5-(4-isopropyl-piperazine-1-carbonyl)-1H-indol-2-yl]-(4,4-difluoro-piperidin-1-yl)-methanone The title compound was synthesized in analogy to example 66, from [4-chloro-2-(4,4-difluoro-piperidine-1-carbonyl)-1H-indol-5-yl]-(4-isopropyl-piperazin-1-yl)-methanone (example 228), 2-chloropyridine-4-boronic acid, copper(II) acetate, pyridine and using chloroforme instead of dichloromethane as solvent, to give the desired product as a colorless foam (34%).

MS (ISP): 564.4 (M+H$^+$)

Example 231

[6-Chloro-1-isopropyl-5-(4-isopropyl-piperazine-1-carbonyl)-1H-indol-2-yl]-(4,4-difluoro-piperidin-1-yl)-methanone The title compound was synthesized in analogy to example 51, from [2-(1,1-dioxo-thiomorpholine-4-carbonyl)-1H-indol-5-yl]-(4-isopropyl-piperazin-1-yl)-methanone (example 1), sodium hydride and 2-bromopropane in N,N-dimethylformamide, to give the desired product as a colorless foam (61%).

MS (ISP): 495.3 (M+H$^+$)

Examples 232 and 233

[7-Chloro-2-(4,4-difluoro-piperidine-1-carbonyl)-1H-indol-5-yl]-(4-isopropyl-piperazin-1-yl)-methanone and [7-Chloro-5-(4-isopropyl-piperazine-1-carbonyl)-1H-indol-2-yl]-(4-isopropyl-piperazin-1-yl)-methanone The title compounds were synthesized in analogy to example 1, from 7-chloro-2-(4,4-difluoro-piperidine-1-carbonyl)-1H-indole-5-carboxylic acid hydrochloride and 7-chloro-1H-indole-2,5-dicarboxylic acid (intermediate c), 1-isopropylpiperazine (commercially available), O-(benzotriazol-1-yl)-N,N,N',N'-tetramethyluronium tetrafluoroborate (commercially available) and N,N-diisopropylethylamine in N,N-dimethylformamide. The products were separated by silica gel chromatography using dichloromethane:methanol (19:1 v/v) as eluant.

MS (ISP): 453.2 (M+H$^+$) MS (ISP): 460.3 (M+H$^+$)

Intermediates (5-Bromo-7-chloro-1H-indol-2-yl)-(4,4-difluoro-piperidin-1-yl)-methanone The title compound was synthesized in analogy to example 1 from 5-bromo-7-chloro-1H-indole-2-carboxylic acid (commercially available), O-(benzotriazol-1-yl)-N,N,N',N'-tetramethyluronium tetrafluoroborate (commercially available), 2,4-difluoro piperidine (commercially available) and N,N-diisopropylethylamine in N,N-dimethylformamide to give the desired product as a colorless foam (89%).

MS (EI): 378.0 (M)

7-Chloro-2-(4,4-difluoro-piperidine-1-carbonyl)-1H-indole-5-carboxylic acid methyl ester The mixture consistent of 100 mg (0.265 mmol) (5-bromo-7-chloro-1H-indol-2-yl)-(4,4-difluoro-piperidin-1-yl)-methanone, 15 mg (0.0184 mmol) 1,1'-bis(diphenylphosphino)ferrocene palladium dichloride and 55.6 µL (0.398 mmol) triethylamine in 1 mL ethanol and 1 mL ethyl acetate was stirred overnight at 100° C. under an atmosphere of carbon monoxide (120 bar). After cooling to room temperature the reaction mixture is filtered, evaporated and chromatographed on silica gel with ethyl acetate:n-heptane (1:2 v/v) as eluant to give the desired compound as a colorless solid (69%).

MS (TIC): 713.1 (2M+H$^+$); 357.1 (M+H$^+$)

7-Chloro-2-(4,4-difluoro-piperidine-1-carbonyl)-1H-indole-5-carboxylic acid; hydrochloride and 7-chloro-1H-indole-2,5-dicarboxylic acid To the solution of 0.2 g (0.56 mmol) 7-chloro-2-(4,4-difluoro-piperidine-1-carbonyl)-1H-indole-5-carboxylic acid methyl ester in 8 mL tetrahydrofuran, 17 mg (0.71 mmol) lithium hydroxide were added and after the addition of 4 mL water, the solution was stirred at reflux temperature. After eight hours, the oil bath was removed and the solvent was removed at a rotary evaporator. The pH of the residual solution was adjusted to 1-2 using 4M hydrochloric acid upon which a suspension formed. The suspension was filtered and the remaining solid was washed with a small amount of water to give a mixture of the title compound and 7-chloro-1H-indole-2,5-dicarboxylic acid (60% overall) in form of a colorless solid.

MS (ISP): 341.1 (M−H$^+$)

Example 234

[7-Chloro-1-isopropyl-5-(4-isopropyl-piperazine-1-carbonyl)-1H-indol-2-yl]-(4,4-difluoro-piperidin-1-yl)-methanone The title compound was synthesized in analogy to example 51, from [7-chloro-2-(4,4-difluoro-piperidine-1-carbonyl)-1H-indol-5-yl]-(4-isopropyl-piperazin-1-yl)-methanone (example 232), sodium hydride and 2-bromopropane in N,N-dimethylformamide, to give the desired product as a colorless foam (24%).

MS (ISP): 495.2 (M+H$^+$)

Example 235

[5-(3-Dimethylamino-piperidine-1-carbonyl)-1H-indol-2-yl]-morpholin-4-yl-methanone The title compound was synthesized in analogy to Example 1, from 5-(3-dimethylamino-piperidine-1-carbonyl)-1H-indole-2-carboxylic acid, morpholine and 1-ethyl-3-(3-dimethylaminopropyl)-carbodiimide hydrochloride, to afford the product as an off-white solid (37%).

MS (m/z): 385.3 (M+H$^+$)

Intermediates

Ethyl 5-(3-dimethylamino-piperidine-1-carbonyl)-1H-indole-2-carboxylate

The title compound was synthesized in analogy to Example 1, Intermediate 1a), from 1H-indole-2,5-dicarboxylic acid 2-ethyl ester, 3-dimethylamino-piperidine and 1-ethyl-3-(3-dimethylaminopropyl)-carbodiimide hydrochloride, to afford the product as a light-brown solid (63%).

MS (m/z): 343.4 (M+H$^+$)

5-(3-Dimethylamino-piperidine-1-carbonyl)-1H-indole-2-carboxylic acid

The title compound was synthesized in analogy to Example 1, Intermediate 1b), from ethyl 5-(3-dimethylamino-piperidine-1-carbonyl)-1H-indole-2-carboxylate, to afford the product as a light-brown solid.

MS (m/z): 316.1 (M+H$^+$)

Example 236

[5-(3-Dimethylamino-piperidine-1-carbonyl)-1-isopropyl-1H-indol-2-yl]-morpholin-4-yl-methanone The title compound was synthesized in analogy to Example 1, from 5-(3-dimethylamino-piperidine-1-carbonyl)-1-isopropyl-1H-indole-2-carboxylic acid, morpholine and 1-ethyl-3-(3-dimethylaminopropyl)-carbodiimide hydrochloride, to afford the product as a colorless foam (42%).

MS (m/z): 427.4 (M+H$^+$)

Intermediates 5-(3-Dimethylamino-piperidine-1-carbonyl)-1-isopropyl-1H-indole-2-carboxylic acid ethyl ester To a solution of ethyl 5-(3-dimethylamino-piperidine-1-carbonyl)-1H-indole-2-carboxylate (1.51 g, 4 mmol) in acetonitrile (30 ml) were added isopropylmethane-sulfonate (1.8 eq, 1.1 g) and caesium carbonate (1.8 eq, 2.6 g). The mixture was heated overnight at reflux. The solvent was evaporated under reduced pressure and the residue partitioned between water and tert-butylmethyl ether. The phases were separated, the aqueous phase extracted with tert-butylmethyl ether and the combined organic phases washed with brine, dried over magnesium sulfate and evaporated under reduced pressure. The residue was purified by column chromatography on silica gel (4:1 chloroform/methanol eluant) to afford the product as a light-brown gum. (31%)

MS (m/z): 386.3 (M+H$^+$)

5-(3-dimethylamino-piperidine-1-carbonyl)-1-isopropyl-1H-indole-2-carboxylic acid The title compound was synthesized in analogy to Example 1, Intermediate 1b), from 5-(3-dimethylamino-piperidine-1-carbonyl)-1-isopropyl-1H-indole-2-carboxylic acid ethyl ester, to afford the product as a light-brown gum.

Example 237

(4,4-Difluoro-piperidin-1-yl)-[5-(3-dimethylamino-piperidine-1-carbonyl)-1-isopropyl-1H-indol-2-yl]-methanone The title compound was synthesized in analogy to Example 1, from 5-(3-dimethylamino-piperidine-1-carbonyl)-1-isopropyl-1H-indole-2-carboxylic acid, 4,4-difluoropiperidine hydrochloride, triethylamine and 1-ethyl-3-(3-dimethylaminopropyl)-carbodiimide hydrochloride, to afford the product as a light-brown oil (79%).

MS (m/z): 461.3 (M+H$^+$)

Example 238

[5-(3-Dimethylamino-piperidine-1-carbonyl)-1-isopropyl-1H-indol-2-yl]-(1,1-dioxo-thiomorpholin-4-yl)-methanone The title compound was synthesized in analogy to Example 1, from 5-(3-dimethylamino-piperidine-1-carbonyl)-1-isopropyl-1H-indole-2-carboxylic acid, thiomorpholine 1,1-dioxide and 1-ethyl-3-(3-dimethylaminopropyl)-carbodiimide hydrochloride, to afford the product as an off-white solid (15%).

MS (m/z): 475.4 (M+H$^+$)

Example 239

[1-Isopropyl-5-(4-isopropyl-[1,4]diazepane-1-carbonyl)-1H-indol-2-yl]-morpholin-4-yl-methanone To a solution of 4-[1-isopropyl-2-(morpholine-4-carbonyl)-1H-indole-5-carbonyl]-[1,4]diazepane-1-carboxylic acid tert-butyl ester (134 mg) in ethyl acetate was added a 5M solution of hydrogen chloride in ethyl acetate. The mixture was stirred 2 days at room temperature, and evaporated to dryness to afford the hydrochloride salt of the deprotected amine as a white solid. The solid was suspended in 1,2-dichloroethane (5 ml). Triethylamine (0.06 ml), acetone (0.22 ml) and sodium triacetoxyborohydride (171 mg) were added and the mixture stirred 2 days at room temperature. Sodium bicarbonate was added and the mixture stirred vigorously. The product was isolated by column chromatography on silica gel (18:2:0.05 chloroform/methanol/aq ammonium hydroxide eluant) as a light yellow gum (97%).

MS (m/z): 441.6 (M+H$^+$)

Intermediates

4-[1-Isopropyl-2-(morpholine-4-carbonyl)-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1-isopropyl-1H-indole-2-carboxylic acid, morpholine and 1-ethyl-3-(3-dimethylaminopropyl)-carbodiimide hydrochloride, to afford the product as a yellow solid (91%).

MS (m/z): 499.5 (M+H$^+$)

5-(4-tert-Butoxycarbonyl-[1,4]diazepane-1-carbonyl)-1-isopropyl-1H-indole-2-carboxylic acid The title compound was synthesized in analogy to Example 1, Intermediate 1b), from 5-(4-tert-butoxycarbonyl-[1,4]diazepane-1-carbonyl)-1-isopropyl-1H-indole-2-carboxylic acid ethyl ester, to afford the product as an off-white powder (78%).

MS (m/z): 430.5 (M+H$^+$)

5-(4-tert-Butoxycarbonyl-[1,4]diazepane-1-carbonyl)-1-isopropyl-1H-indole-2-carboxylic acid ethyl ester The title compound was synthesized in analogy to example 239, Intermediate a), from 5-(4-tert-butoxycarbonyl-[1,4]diazepane-1-carbonyl)-1H-indole-2-carboxylic acid ethyl ester and isopropylmethanesulfonate, to afford the product as a yellow oil (62%).

MS (m/z): 458.5 (M+H$^+$)

5-(4-tert-Butoxycarbonyl-[1,4]diazepane-1-carbonyl)-1H-indole-2-carboxylic acid ethyl ester The title compound was synthesized in analogy to Example 1, from 1H-indole-2,5-dicarboxylic acid 2-ethyl ester, [1,4]diazepane-1-carboxylic acid tert-butyl ester and 1-ethyl-3-(3-dimethylaminopropyl)-carbodiimide hydrochloride, to afford the product as a white solid (69%).

MS (m/z): 416.5 (M+H$^+$)

Example 240

(4,4-Difluoro-piperidin-1-yl)-[1-isopropyl-5-(4-isopropyl-[1,4]diazepane-1-carbonyl)-1H-indol-2-yl]-methanone The title compound was synthesized in analogy to Example 239, from 4-[2-(4,4-difluoro-piperidine-1-carbonyl)-1-isopropyl-1H-indole-5-carbonyl]-[1,4]diazepane-1-carboxylic acid tert-butyl ester, to afford the product as a light-yellow gum (88%).

MS (m/z): 475.3 (M+H$^+$)

Intermediate

4-[2-(4,4-Difluoro-piperidine-1-carbonyl)-1-isopropyl-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1-isopropyl-1H-indole-2-carboxylic acid, 4,4-difluoropiperidine hydrochloride, triethylamine and 1-ethyl-3-(3-dimethylaminopropyl)-carbodiimide hydrochloride, to afford the product as a yellow solid (70%).

MS (m/z): 533.3 (M+H$^+$)

Example 241

[5-(4-sec-Butyl-[1,4]diazepane-1-carbonyl)-1H-indol-2-yl]-morpholin-4-yl-methanone The title compound was synthesized in analogy to Example 239, from 4-[2-(morpholine-4-carbonyl)-1H-indole-5-carbonyl]-[1,4]diazepane-1-carboxylic acid tert-butyl ester and 2-butanone, to afford the product as a light-yellow gum (19%).

MS (m/z): 413.5 (M+H$^+$)

Intermediates

4-[2-(Morpholine-4-carbonyl)-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1H-indole-2-carboxylic acid, morpholine and 1-ethyl-3-(3-dimethylaminopropyl)-carbodiimide hydrochloride, to afford the product as an off-white solid (99%).

MS (m/z): 457.3 (M+H$^+$)

5-(4-tert-butoxycarbonyl-[1,4]diazepane-1-carbonyl)-1H-indole-2-carboxylic acid

The title compound was synthesized in analogy to Example 1, Intermediate 1b), from 5-(4-tert-butoxycarbonyl-[1,4]diazepane-1-carbonyl)-1H-indole-2-carboxylic acid ethyl ester, to afford the product as a light brown gum (96%).

MS (m/z): 386.4 (M−H)$^−$

Example 242

(1,1-Dioxo-thiomorpholin-4-yl)-[1-isopropyl-5-(4-isopropyl-[1,4]diazepane-1-carbonyl)-1H-indol-2-yl]-methanone The title compound was synthesized in analogy to Example 239, from 4-[2-(1,1-dioxo-thiomorpholine-4-carbonyl)-1-isopropyl-1H-indole-5-carbonyl]-[1,4]diazepane-1-carboxylic acid tert-butyl ester, to afford the product as an off-white solid (47%).

MS (m/z): 489.3 (M+H$^+$)

Intermediate

4-[2-(1,1-dioxo-thiomorpholine-4-carbonyl)-1-isopropyl-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1-isopropyl-1H-indole-2-carboxylic acid, thiomorpholine 1,1-dioxide and 1-ethyl-3-(3-dimethylaminopropyl)-carbodiimide hydrochloride, to afford the product as an off-white solid (85%).

MS (m/z): 547.2 (M+H$^+$)

Example 243

[5-(4-Isopropyl-[1,4]diazepane-1-carbonyl)-1H-indol-2-yl]-morpholin-4-yl-methanone The title compound was synthesized in analogy to Example 239, from 4-[2-(morpholine-4-carbonyl)-1H-indole-5-carbonyl]-[1,4]diazepane-1-carboxylic acid tert-butyl ester, to afford the product as a white solid (55%).

MS (m/z): 399.3 (M+H$^+$)

Example 244

(4,4-Difluoro-piperidin-1-yl)-[5-(4-isopropyl-[1,4]diazepane-1-carbonyl)-1H-indol-2-yl]-methanone The title compound was synthesized in analogy to Example 239, from 4-[2-(4,4-difluoro-piperidine-1-carbonyl)-1H-indole-5-carbonyl]-[1,4]diazepane-1-carboxylic acid tert-butyl ester, to afford the product as an orange solid (14%).

MS (m/z): 433.3 (M+H$^+$)

Intermediate 4-[2-(4,4-difluoro-piperidine-1-carbonyl)-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1H-indole-2-carboxylic acid, 4,4-difluoropiperidine hydrochloride, triethylamine and 1-ethyl-3-(3-dimethylaminopropyl)-carbodiimide hydrochloride, to afford the product as a yellow solid (87%).

MS (m/z): 491.2 (M+H$^+$)

Example 245

(1,1-Dioxo-thiomorpholin-4-yl)-[5-(4-isopropyl-[1,4]diazepane-1-carbonyl)-1H-indol-2-yl]-methanone The title compound was synthesized in analogy to Example 239, from 4-[2-(1,1-dioxo-thiomorpholine-4-carbonyl)-1H-indole-5-carbonyl]-[1,4]diazepane-1-carboxylic acid tert-butyl ester, to afford the product as a white solid (68%).

MS (m/z): 447.1 (M+H$^+$)

Intermediate

4-[2-(1,1-Dioxo-thiomorpholine-4-carbonyl)-1H-indole-5-carbonyl]-[1,4]diazepane-1-carboxylic acid tert-butyl ester The title compound was synthesized in analogy to Example 1, from 5-(4-tert-butoxycarbonyl-[1,4]diazepane-1-carbonyl)-1H-indole-2-carboxylic acid, thiomorpholine 1,1-dioxide and 1-ethyl-3-(3-dimethylaminopropyl)-carbodiimide hydrochloride, to afford the product as a yellow solid (95%).

MS (m/z): 505.1 (M+H$^+$)

Example 246

[5-(4-Cyclopropyl-[1,4]diazepane-1-carbonyl)-1H-indol-2-yl]-(1,1-dioxo-thiomorpholin-4-yl)-methanone To a solution of 4-[2-(1,1-dioxo-thiomorpholine-4-carbonyl)-1H-indole-5-carbonyl]-[1,4]diazepane-1-carboxylic acid tert-butyl ester (120 mg) in ethyl acetate (3 ml) was added 5M methanolic hydrogen chloride solution. The mixture was stirred overnight at room temperature. The solvent was removed under reduced pressure and the residue dissolved in methanol. (1-Ethoxycyclopropoxy)trimethylsilane (125 mg) and acetic acid (0.14 ml) were added. Sodium cyanoborohydride (45 mg) was slowly added, and the mixture stirred overnight at room temperature. The reaction was quenched by the addition of saturated aqueous sodium hydrogencarbonate solution. The mixture was extracted with dichloromethane (3×25 ml), dried over magnesium sulfate and evaporated under reduced pressure. The residue was purified by column chromatography on silica gel (19:1 chloroform/methanol eluant) to afford the product as an off-white solid (47%).

MS (m/z): 445.3 (M+H$^+$)

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

-continued

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:
1. A compound of formula I:

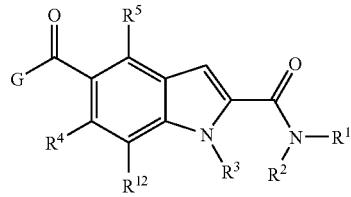

wherein:
R$^1$ is selected from the group consisting of
lower alkyl, lower alkenyl, lower alkinyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one to three groups independently selected from lower alkyl, halogen, lower halogenalkoxy and lower hydroxyalkyl,
lower phenylalkyl wherein the phenyl ring may be unsubstituted or substituted with one to three groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl,
lower heterocyclylalkyl wherein the heterocyclyl ring may be unsubstituted or substituted with one or two groups selected from lower alkyl and halogen, and
7-oxa-bicyclo[2.2.1]heptyl;

$R^2$ is selected from the group consisting of hydrogen,
lower alkyl, lower alkenyl, lower alkinyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
   phenyl unsubstituted or substituted with one to three groups independently selected from lower alkyl, halogen, lower halogenalkoxy and lower hydroxyalkyl,
   lower phenylalkyl wherein the phenyl ring may be unsubstituted or substituted with one to three groups independently selected from lower alkyl, halogen, lower alkoxy and lower hydroxyalkyl,
   lower heteroarylalkyl wherein the heteroaryl ring may be unsubstituted or substituted with one or two groups independently selected from lower alkyl, halogen, lower alkoxy and lower hydroxyalkyl, and
   lower heterocyclylalkyl wherein the heterocycly ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring
   being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or
   being condensed with a phenyl ring, said phenyl ring being unsubstituted or substituted by one, two or three groups independently selected from lower alkyl, lower alkoxy and halogen, or
   $R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one;
$R^3$ is selected from the group consisting of hydrogen, lower alkyl, cycloalkyl, lower hydroxyalkyl, lower alkoxyalkyl, lower halogenalkyl, lower cycloalkylalkyl, lower alkanoyl, lower cyanoalkyl, lower alkylsulfonyl,
   phenylsulfonyl wherein the phenyl ring may be unsubstituted or substituted with one to three groups independently selected from lower alkyl, halogen, lower alkoxy, lower halogenalkoxy and lower hydroxyalkyl,
   phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl,
   lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
   heteroaryl unsubstituted or substituted with one or two groups independently selected from lower alkyl, lower alkoxy, cyano, morpholinyl and halogen;

$R^4$, $R^{12}$ and $R^5$ are hydrogen, or
   one of $R^4$, $R^{12}$ and $R^5$ is halogen and the other ones are hydrogen;
G is

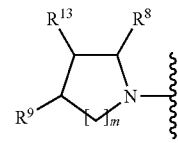

G2 wherein
   m is 1 or 2;
   $R^8$ is hydrogen or lower heterocyclylalkyl;
   $R^9$ is hydrogen or $-NR^{10}R^{11}$;
   $R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur;
   $R^{13}$ is hydrogen or $-NR^{10}R^{11}$;
or a pharmaceutically acceptable salt thereof.

2. The compound according to claim 1, wherein $R^1$ is selected from the group consisting of
   lower alkyl, lower alkenyl, lower alkinyl,
   cycloalkyl, lower cycloalkylalkyl,
   lower hydroxyalkyl,
   lower alkoxyalkyl,
   lower alkylsulfanylalkyl,
   lower dialkylaminoalkyl,
   lower dialkylcarbamoylalkyl,
   phenyl unsubstituted or substituted with one to three groups independently selected from lower alkyl, halogen, lower halogenalkoxy and lower hydroxyalkyl,
   lower phenylalkyl wherein the phenyl ring may be unsubstituted or substituted with one to three groups independently selected from lower alkyl, halogen, lower alkoxy and lower hydroxyalkyl,
   lower heteroarylalkyl wherein the heteroaryl ring may be unsubstituted or substituted with one or two groups independently selected from lower alkyl, halogen, lower alkoxy and lower hydroxyalkyl,
   lower heterocyclylalkyl wherein the heterocyclyl ring may be unsubstituted or substituted with one or two groups selected from lower alkyl and halogen, and
   7-oxa-bicyclo[2.2.1]heptyl; and
   $R^2$ is hydrogen or lower alkyl.

3. The compound according to claim 1, wherein $R^1$ is selected from the group consisting of cycloalkyl,
   phenyl unsubstituted or substituted with one to three groups independently selected from lower alkyl, halogen, lower halogenalkoxy and lower hydroxyalkyl,
   lower phenylalkyl wherein the phenyl ring may be unsubstituted or substituted with one to three groups independently selected from lower alkyl, halogen, lower alkoxy and lower hydroxyalkyl, and
   lower heterocyclylalkyl wherein the heterocyclyl ring may be unsubstituted or substituted with one or two groups selected from lower alkyl and halogen; and
   $R^2$ is hydrogen or lower alkyl.

4. The compound according to claim 1, wherein
   $R^1$ and $R^2$ together with the nitrogen atom to which they are attached form a 4-, 5-, 6- or 7-membered saturated or partly unsaturated heterocyclic ring optionally containing a further heteroatom selected from oxygen or sulfur, a sulfinyl group or a sulfonyl group, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or $R^1$ and $R^2$ together with the nitrogen atom to which they are attached form a group selected from 1-oxa-8-aza-spiro [4.5]decyl, 1,4-dioxa-8-aza-spiro[4.5]decyl and [1,4] oxazepan-7-one.

5. The compound according to claim 1, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine, 1,1-dioxothiomorpholine and 3,6-dihydro-2H-pyridine, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or wherein $R^1$ and $R^2$ together with the nitrogen atom to which they are attached form a group selected from 1-oxa-8-aza-spiro[4.5]decyl, 1,4-dioxa-8-aza-spiro[4.5]decyl and [1,4]oxazepan-7-one.

6. The compound according to claim 1, wherein $R^1$ and $R^2$ together with the nitrogen atom to which they are attached form a heterocyclic ring selected from the group consisting of morpholine, thiomorpholine, 1,1-dioxothiomorpholine, pyrrolidine, piperidine and azepane, said heterocyclic ring being unsubstituted or substituted by one, two or three groups independently selected from lower alkyl, halogen, lower halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen, or wherein $R^1$ and $R^2$ together with the nitrogen atom to which they are attached form a 1,4-dioxa-8-aza-spiro[4.5]decyl group.

7. The compound according to claim 1, wherein $R^1$ and $R^2$ together with the nitrogen atom to which they are attached form a heterocyclic ring selected from the group consisting of morpholine, thiomorpholine, 1,1-dioxothio-morpholine, pyrrolidine, piperidine and 4,4-difluoropiperidinyl.

8. The compound according to claim 1, wherein $R^3$ is selected from the group consisting of hydrogen, lower alkyl, cycloalkyl, lower hydroxyalkyl, lower alkoxyalkyl, lower halogenalkyl, lower cycloalkylalkyl, lower cyanoalkyl, lower alkylsulfonyl, phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, benzodioxolyl, lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and heteroaryl unsubstituted or substituted with one or two groups independently selected from lower alkyl, lower alkoxy, cyano, morpholinyl and halogen.

9. The compound according to claim 1, wherein $R^3$ is selected from the group consisting of hydrogen, lower alkyl, cycloalkyl, lower hydroxyalkyl, lower alkoxyalkyl, lower halogenalkyl, lower cycloalkylalkyl, lower cyanoalkyl and lower alkylsulfonyl.

10. The compound according to claim 1, wherein $R^3$ is lower alkyl or lower halogenalkyl.

11. The compound according to claim 1, wherein $R^3$ is phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower alkylsulfonyl and lower alkylsulfonylamino, benzodioxolyl, or lower phenylalkyl, wherein the phenyl ring may be unsubstituted or substituted with one to three groups independently selected from halogen, cyano or lower halogenalkyl.

12. The compound according to claim 1, wherein $R^3$ is unsubstituted phenyl or phenyl substituted with one to three groups independently selected from halogen, cyano or lower halogenalkyl.

13. The compound according to claim 1, wherein $R^3$ is heteroaryl selected from pyridyl or pyrimidinyl, said heteroaryl being unsubstituted or substituted with one or two groups independently selected from lower alkyl, lower alkoxy, cyano, morpholinyl and halogen.

14. The compound according to claim 1, wherein $R^4$, $R^{12}$ and $R^5$ are hydrogen.

15. The compound according to claim 1, wherein $R^8$ is hydrogen, $R^9$ is $—NR^{10}R^{11}$, $R^{13}$ is hydrogen and $R^{10}$ and $R^{11}$ independently from each other are lower alkyl or together with the nitrogen atom to which they are attached form a 5- or 6-membered saturated heterocyclic ring optionally containing a further heteroatom selected from nitrogen, oxygen or sulfur.

16. The compound according to claim 1, wherein $R^8$ is lower heterocyclylalkyl and $R^9$ is hydrogen.

17. A pharmaceutical composition, comprising a therapeutically effective amount of a compound according to claim 1 as well as a pharmaceutically acceptable carrier and/or adjuvant.

* * * * *